(12) United States Patent
Lanza et al.

(10) Patent No.: US 11,141,379 B2
(45) Date of Patent: *Oct. 12, 2021

(54) PRODRUG COMPOSITIONS, PRODRUG NANOPARTICLES, AND METHODS OF USE THEREOF

(71) Applicant: Washington University, St. Louis, MO (US)

(72) Inventors: Gregory M. Lanza, St. Louis, MO (US); Dipanjan Pan, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/234,044

(22) Filed: Dec. 27, 2018

(65) Prior Publication Data

US 2019/0192436 A1    Jun. 27, 2019

Related U.S. Application Data

(60) Continuation of application No. 15/179,626, filed on Jun. 10, 2016, now Pat. No. 10,201,500, which is a
(Continued)

(51) Int. Cl.
*A61K 9/14* (2006.01)
*A61K 9/127* (2006.01)
(Continued)

(52) U.S. Cl.
CPC ............ *A61K 9/145* (2013.01); *A61K 9/0019* (2013.01); *A61K 9/1075* (2013.01); *A61K 9/1271* (2013.01); *A61K 31/336* (2013.01); *A61K 31/337* (2013.01); *A61K 33/24* (2013.01); *A61K 41/0071* (2013.01); *A61K 47/555* (2017.08); *A61K 9/08* (2013.01); *A61K 9/10* (2013.01); *A61K 47/6907* (2017.08); *Y10S 977/773* (2013.01); *Y10S 977/906* (2013.01)

(58) Field of Classification Search
CPC ..................................................... A61K 9/145
See application file for complete search history.

(56) References Cited

U.S. PATENT DOCUMENTS

| | | |
|---|---|---|
| 3,215,572 A | 11/1965 | Papell |
| 5,077,036 A | 12/1991 | Long, Jr. |

(Continued)

FOREIGN PATENT DOCUMENTS

| | | |
|---|---|---|
| WO | 1996020698 A2 | 7/1996 |
| WO | 2001074337 A1 | 10/2001 |

(Continued)

OTHER PUBLICATIONS

Hiroshima Metal & Machinery. http://www.hiroshimamm-chemtech.com/en/knowledge/detail02/ downloaded on Oct. 14, 2020, 5 printed pages. (Year: 2020).*

(Continued)

*Primary Examiner* — Isaac Shomer
(74) *Attorney, Agent, or Firm* — Polsinelli PC

(57) ABSTRACT

The present invention encompasses prodrug compositions, nanoparticles comprising one or more prodrugs, and methods of use thereof.

18 Claims, 40 Drawing Sheets

Specification includes a Sequence Listing.

Related U.S. Application Data division of application No. 13/641,252, filed as application No. PCT/US2011/032744 on Apr. 15, 2011, now Pat. No. 9,498,439.

(60) Provisional application No. 61/324,464, filed on Apr. 15, 2010.

(51) Int. Cl.

| | | |
|---|---|---|
| *A61K 31/336* | (2006.01) | |
| *A61K 9/107* | (2006.01) | |
| *A61K 31/337* | (2006.01) | |
| *A61K 9/00* | (2006.01) | |
| *A61K 33/24* | (2019.01) | |
| *A61K 41/00* | (2020.01) | |
| *A61K 47/54* | (2017.01) | |
| *A61K 9/08* | (2006.01) | |
| *A61K 9/10* | (2006.01) | |
| *A61K 47/69* | (2017.01) | |

(56) References Cited

U.S. PATENT DOCUMENTS

| | | |
|---|---|---|
| 5,114,703 A | 5/1992 | Wolf et al. |
| 5,171,755 A | 12/1992 | Kaufman et al. |
| 5,260,306 A | 11/1993 | Boardman et al. |
| 5,304,325 A | 4/1994 | Kaufman et al. |
| 5,350,571 A | 9/1994 | Kaufman et al. |
| 5,393,524 A | 2/1995 | Quay |
| 5,403,575 A | 4/1995 | Kaufman et al. |
| 5,534,499 A * | 7/1996 | Ansell .................. A61K 9/1271 514/25 |
| 5,690,907 A | 11/1997 | Lanza et al. |
| 5,780,010 A | 7/1998 | Lanza et al. |
| 5,820,848 A | 10/1998 | Boni et al. |
| 5,939,567 A | 8/1999 | Mayhew et al. |
| 5,958,371 A | 9/1999 | Lanza et al. |
| 5,989,520 A | 11/1999 | Lanza et al. |
| 6,350,458 B1 | 2/2002 | Modi |
| 6,368,586 B1 | 4/2002 | Jacob et al. |
| 6,413,544 B1 | 7/2002 | Smyth-Templeton et al. |
| 6,491,903 B1 | 12/2002 | Forster et al. |
| 6,579,846 B1 | 6/2003 | Zirnstein et al. |
| 7,022,313 B2 | 4/2006 | O'Connor et al. |
| 9,446,150 B2 | 9/2016 | Lanza et al. |
| 9,468,607 B2 | 10/2016 | Pan et al. |
| 9,498,439 B2 * | 11/2016 | Lanza ................. A61K 41/0071 |
| 9,764,043 B2 | 9/2017 | Myerson et al. |
| 10,201,500 B2 * | 2/2019 | Lanza .................... A61K 33/24 |
| 2002/0034536 A1 | 3/2002 | Perkins et al. |
| 2003/0157179 A1 | 8/2003 | Blum et al. |
| 2003/0185879 A1 | 10/2003 | Boulikas |
| 2004/0142474 A1 | 7/2004 | Mahato et al. |
| 2004/0229945 A1 | 11/2004 | Satchi-Fainaro et al. |
| 2005/0037050 A1 | 2/2005 | Weber |
| 2005/0079131 A1 | 4/2005 | Lanza et al. |
| 2005/0095267 A1 | 5/2005 | Campbell et al. |
| 2006/0008461 A1 | 1/2006 | Yatvin et al. |
| 2006/0015261 A1 | 1/2006 | Mann et al. |
| 2006/0159619 A1 | 7/2006 | Becker et al. |
| 2006/0228299 A1 | 10/2006 | Thorpe et al. |
| 2006/0264397 A1 | 11/2006 | Kucera et al. |
| 2006/0269479 A1 | 11/2006 | Colton et al. |
| 2007/0020308 A1 | 1/2007 | Richard et al. |
| 2007/0110777 A1 | 5/2007 | Joabsson et al. |
| 2007/0154539 A1 | 7/2007 | Fountain |
| 2008/0081074 A1 | 4/2008 | Gu et al. |
| 2008/0269875 A1 | 10/2008 | Zhao |
| 2008/0286321 A1 | 11/2008 | Reneker et al. |
| 2008/0286372 A1 | 11/2008 | Pacetti et al. |
| 2009/0148383 A1 | 6/2009 | Peter |
| 2009/0163437 A1 | 6/2009 | Rusconi |
| 2009/0202429 A1 | 8/2009 | Diacovo et al. |
| 2009/0208548 A1 | 8/2009 | Mason et al. |
| 2010/0028994 A1 | 2/2010 | DeSimone et al. |
| 2010/0297007 A1 | 11/2010 | Lanza et al. |
| 2010/0297019 A1 | 11/2010 | Lanza et al. |
| 2013/0064765 A1 | 3/2013 | Myerson et al. |
| 2013/0122100 A1 | 5/2013 | Lanza et al. |
| 2014/0023703 A1 * | 1/2014 | Alonso Fernandez ................ A61K 31/337 424/452 |
| 2016/0279060 A1 | 9/2016 | Lanza et al. |
| 2017/0231917 A1 * | 8/2017 | Wooster ............... A61K 9/2063 424/477 |

FOREIGN PATENT DOCUMENTS

| | | |
|---|---|---|
| WO | 2003015831 A1 | 2/2003 |
| WO | 2004017907 A2 | 3/2004 |
| WO | 2005014051 A1 | 2/2005 |
| WO | 2006072943 A2 | 7/2006 |
| WO | 2006117720 A2 | 11/2006 |
| WO | 2007034359 A2 | 3/2007 |
| WO | 2007106683 A2 | 9/2007 |
| WO | 2008063157 A2 | 5/2008 |
| WO | 2008109712 A2 | 9/2008 |
| WO | 2009049083 A1 | 4/2009 |
| WO | 2009049089 A1 | 4/2009 |
| WO | 2011084700 A1 | 7/2011 |
| WO | 2011130674 A1 | 10/2011 |

OTHER PUBLICATIONS

Rosensweig, "Magnetic Fluids: Tiny ferromagnetic particles suspended in an organic liquid form a new kind of fluid responsive to magnetic fields in queer but useful ways," International Science and Technology, 1966, pp. 48-56.

Rothwarf D. et al., "IKK-Gamma is an essential regulatory subunit of the IκB kinase complex," Nature, 1998, pp. 297-300, vol. 395.

Schwartz et al., "Microemboli and Microvascular Obstruction in Acute Coronary Thrombosis and Sudden Coronary Death," Journal of the American College of Cardiology, 2009, pp. 2167-2173, vol. 54, No. 23.

Sie et al., "Constitutional Heparin Co-Factor II Deficiency Associated with Recurrent Thrombosis," Lancet, 1985, pp. 414-416, vol. 2.

Smale, "Selective Transcription in Response to an Inflammatory Stimulus," Cell, 2010, pp. 833-844, vol. 140, No. 6.

Soman et al., "Molecularly targeted nanocarriers deliver the cytolytic peptide melittin specifically to tumor cells in mice, reducing tumor growth," The Journal of Clinical Investigation, 2009, pp. 2830-2842, vol. 119, No. 9.

Soman et al., "Synthesis and Characterization of Stable Fluorocarbon Nanostructures as Drug Delivery Vehicles for Cytolytic Peptides," Nano Lett., 2008, pp. 1131-1136, vol. 8, No. 4.

Srivastava et al., "Progress in the Design of Low Molecular Weight Thrombin Inhibitors," Medicinal Research Reviews, 2005, pp. 66-92, vol. 25, No. 1.

Su, "Assembly of polydiacetylene vesicles on solid substrates," J. Colloid and Interface Science, 2005, pp. 271-276, vol. 292.

Sun et al., "Persistent activation of NF-κB by the Tax transforming protein of HTLV-1: hijacking cellular IκB kinases," Oncogene, 1999, pp. 6948-6958, vol. 18.

Thorek et al., "Superparamagnetic Iron Oxide Nanoparticle Probes for Molecular Imaging," Annals of Biomedical Engineering, 2006, pp. 23-38, vol. 34, No. 1.

Torreri et al., "Biomolecular interactions by Surface Plasmon Resonance technology," Ann 1st Super Sanita, 2005, pp. 437-441, vol. 41, No. 4.

Tran et al., "Association of Hereditary Heparin Co-Factor II Deficiency With Thrombosis," Lancet, 1985, pp. 413-414, vol. 2.

Turpie, "The top 4 advances in antithrombotic care in the last year," Thrombosis Research, 2008, pp. S2-S6, vol. 123.

Verweij et al., "Paclitaxel (Taxol) and docetaxel (Taxotere): Not simply two of a kind," Annals of Oncology, 1994, pp. 495-505, vol. 5.

(56) References Cited

OTHER PUBLICATIONS

Vicente et al., "Antithrombotic activity of dermatan sulfate in heparin cofactor II-deficient mice," Blood, 2004, pp. 3965-3970, vol. 104, No. 13.
Vyavahare et al., "In vitro and in vivo evaluation of the site-specific administration of D-phenylalanyl-L-prolyl-L-arginyl chloromethyl ketone (PPACK): a powerful thrombin inhibitor," Journal of Controlled Release, 1993, pp. 165-173, vol. 27, No. 2.
Wallentin et al., "Ticagrelor versus Clopidogrel in Patients with Acute Coronary Syndromes," N. Engl. J. Med., 2009, pp. 1045-1057, vol. 361, No. 11.
Weissmann et al., "Effect of melittin upon cellular and lysosomal membranes," Biochemical Pharmacology, 1969, pp. 1771-1775, vol. 18.
Westrick et al., "Murine Models of Vascular Thrombosis," Arteriosclerosis, Thrombosis, and Vascular Biology, 2007, pp. 2079-2093, vol. 27.
Winter et al., "Emerging nanomedicine opportunities with perfluorocarbon nanoparticles," Expert Rev. Med. Devices, 2007, pp. 137-145, vol. 4, No. 2.
Winter et al., "Antiangiogenic Synergism of Integrin-Targeted Fumagillin Nanoparticles and Atorvastatin in Atherosclerosis," JACC: Cardiovascular Imaging, Sep. 2008, pp. 624-634, vol. 1, No. 5.
Winter et al., "Molecular Imaging of Angiogenesis in Early-Stage Atherosclerosis With $\alpha v \beta 3$-Integrin-Targeted Nanoparticles," Circulation, 2003, pp. 2270-2274, vol. 108.
Winter et al., "Molecular Imaging of Angiogenesis in Nascent Vx-2 Rabbit Tumors Using a Novel $\alpha v \beta 3$-targeted Nanoparticle and 1.5 Tesla Magnetic Resonance Imaging," Cancer Research, 2003, pp. 5838-5843, vol. 63.
Winter et al., "Molecular Imaging by MRI," Current Cardiology Reports, 2006, pp. 65-69, vol. 8.
Winter et al., "Endothelial alphaVbeta3 Integrin-Targeted Fumagillin Nanoparticles Inhibit Angiogenesis in Atherosclerosis," Arterioscler. Thromb. Vasc. Biol., Sep. 2006, pp. 2103-2109, vol. 26.
Xu et al., "Encapsulation of nanosized magnetic iron oxide by polyacrylamide via inverse miniemulsion polymerization," Journal of Magnetism and Magnetic Materials, 2004, pp. 136-143, vol. 277.
Yamaoka et al., "Complementation Cloning of NEMO, a Component of the IκB Kinase Complex Essential for NF-κB Activation," Cell, 1998, pp. 1231-1240, vol. 93.
Yang et al., "Preparation of poly e-caprolactone nanoparticles containing magnetite for magnetic drug carrier," International Journal of Pharmaceutics, 2006, pp. 185-190, vol. 324, No. 2.
Zhou et al. "Suppression of inflammation in a mouse model of rheumatoid arthritis using targeted lipase-labile fumagillin prodrug nanoparticles," Biomaterials, Nov. 1, 2012, pp. 8632-8640, vol. 33, No. 33.
Flaim, "Pharmacokinetics and Side Effects of Perfluorocarbon-Based Blood Substitutes," Artificial Cells, Blood Substitutes, and Immobilization Biotechnology, 1994, pp. 1043-1054, vol. 22, No. 4.
Forrest et al., "Partial Acetylation of Polyethylenimine Enhances In Vitro Gene Delivery," Pharmaceutical Research, 2004, pp. 365-371, vol. 21, No. 2.
Furie et al., "Mehanisms of Thrombus Formation," N. Engl. J. Med., 2008, pp. 938-949, vol. 359, No. 9.
Garg et al., "Nuclear transcription factor-κB as a target for cancer drug development," Leukemia, 2002, pp. 1053-1068, vol. 16.
Ghigliotti et al., "Prolonged Activation of Prothrombin on the Vascular Wall After Arterial Injury," Arteriosclerosis, Thrombosis, and Vascular Biology, 1998, pp. 250-257, vol. 18.
Gilchrist et al., "Selective Inductive Heating of Lymph Nodes," Annals of Surgery, 1957, pp. 596-606, vol. 146, No. 4.
Glagov et al., "Compensatory Enlargement of Human Atherosclerotic Coronary Arteries," N. Engl. J. Med., 1987, pp. 1371-1375, vol. 316, No. 22.
Gross et al., "New Antithrombotic Drugs," Clin. Pharmacol. Therapeut., 2009, pp. 139-146, vol. 86, No. 2.
Grossman et al., "Cytokine Expression and Tumorigenicity of Large Granular Lymphocytic Leukemia Cells From Mice Transgenic for the tax Gene of Human T-Cell Leukemia Virus Type I," Blood, 1997, pp. 783-794, vol. 90, No. 2.
Grossman et al., "Development of leukemia in mice transgenic for the tax gene of human T-cell leukemia virus type I," Proc. Natl. Acad. Sci. USA, 1995, pp. 1057-1061, vol. 92.
Hess et al., "Biological and Chemical Applications of Fluorescence Correlation Spectroscopy: A Review," Biochemistry, 2002, pp. 697-705, vol. 41, No. 3.
Hirano, "The Roles of Proteinase-Activated Receptors in the Vascular Physiology and Pathophysiology," Arteriosclerosis, Thrombosis, and Vascular Biology, 2007, pp. 27-36, vol. 27.
Hirsh et al., "Beyond Unfractionated Heparin and Warfarin: Current and Future Advances," Circulation, 2007, pp. 552-560, vol. 116.
Hofman et al., "Quantification of In-Plane Motion of the Coronary Arteries During the Cardiac Cycle: Implications for Acquisition Window Duration for MR Flow Quantification," Journal of Magnetic Resonance Imaging, 1998, pp. 568-576, vol. 8, No. 3.
Hu et al., "Imaging of Vx-2 rabbit tumors with $\alpha v \beta 3$-integrin-targeted 111In nanoparticles," International Journal of Cancer, 2007, pp. 1951-1957, vol. 120.
Intention to Grant dated Jan. 4, 2018 from related European Patent Application No. 10842655.2; 117 pgs.
Intention to Grant dated Apr. 18, 2018 from related European Patent Application No. 11769698.9; 8 pgs.
International Search Report and Written Opinion dated Dec. 15, 2008 from related International Application No. PCT/US2008/79414; 15 pgs.
International Search Report and Written Opinion dated Dec. 24, 2008 from related International Application No. PCT/US2008/79404; 8 pgs.
International Search Report and Written Opinion dated Apr. 6, 2011 from related International Application No. PCT/US2010/61103; 12 pgs.
International Search Report and Written Opinion dated Jul. 8, 2011 from related International Application No. PCT/US2011/32744; 10 pgs.
Ivey et al., "Thrombin regulates vascular smooth muscle cell proteoglycan synthesis via PAR-1 and multiple downstream signalling pathways," Thrombosis Research, 2008, pp. 288-297, vol. 123.
Kaiser et al., "Pharmacology of Synthetic Thrombin Inhibitors of the Tripeptide Type," Cardiovascular Drug Reviews, 1992, pp. 71-87, vol. 10, No. 1.
Kaneda et al., "Perfluorocarbon Nanoemulsions for Quantitative Molecular Imaging and Targeted Therapeutics," Ann Biomed Eng., 2009, pp. 1922-1933, vol. 37, No. 10.
Karin, "The Beginning of the End: IκB Kinase (IKK) and NF-κB Activation*," The Journal of Biological Chemistry, 1999, pp. 27339-27342, vol. 274, No. 39.
Karin et al., "NF-κB in Cancer: From Innocent Bystander to Major Culprit," Nature Reviews/Cancer, 2002, pp. 301-310, vol. 2.
Karin, "Nuclear factor-κB in cancer development and progression," Nature, 2006, pp. 431-436, vol. 441.
Kettner et al., "$_D$-Phe-Pro-ArgCH2C1-A Selective Affinity Label for Thrombin," Thrombosis Research, 1979, pp. 969-973, vol. 14, No. 6.
Kim et al., "Development of a novel dosage form for intramuscular injection of titrated extract of Centella asiatica in a mixed micellar system," International Journal of Pharmaceutics, 2001, pp. 141-147, vol. 220.
Klocek et al., "Thermodynamics of Melittin Binding to Lipid Bilayers. Aggregation and Pore Formation," Biochemistry, 2009, pp. 2586-2596, vol. 48, No. 12.
Kukreja et al., "The future of drug-eluting stents," Pharmacological Research, 2008, pp. 171-180, vol. 57.
Landfester et al., "Encapsulated magnetite particles for biomedical application," Journal of Physics: Condensed Matter, 2003, pp. S1345-S1361, vol. 15.
Lanza et al., "Targeted Antiproliferative Drug Delivery to Vascular Smooth Muscle Cells With a Magnetic Resonance Imaging Nanoparticle Contrast Agent: Implications for Rational Therapy of Restenosis," Circulation, 2002, pp. 2842-2847, vol. 106.

(56) References Cited

OTHER PUBLICATIONS

Lanza et al., "Molecular Imaging of Stretch-Induced Tissue Factor Expression in Carotid Arteries with Intravascular Ultrasound," Investigative Radiology, 2000, pp. 227-234, vol. 35, No. 4.
Lanza et al., "Nanomedicine opportunities for cardiovascular disease with perfluorocarbon nanoparticles," Nanomedicine, 2006, pp. 321-329, vol. 1, No. 3.
Lee, "Anticoagulants in Coronary Artery Disease," Clinical Cardiology, 2008, pp. 615-628, vol. 26.
Liu et al., "Preparation and characterization of biodegradable magnetic carriers by single emulsion-solvent evaporation," Journal of Magnetism and Magnetic Materials, 2007, pp. 84-87, vol. 311.
Liu et al., "Surface Modification and Characterization of Magnetic Polymer Nanospheres Prepared by Miniemulsion Polymerization," Langmuir, 2004, pp. 10278-10282, vol. 20, No. 23.
Lopez-Guerra et al., "NF-κB as a therapeutic target in chronic lymphocytic leukemia," Expert Opin. Ther. Targets, 2010, pp. 275-288, vol. 14, No. 3.
Mandal et al., "Encapsulation of Magnetic and Fluorescent Nanoparticles in Emulsion Droplets," Langmuir, 2005, pp. 4175-4179, vol. 21, No. 9.
Marsh et al., "Molecular imaging with targeted perfluorocarbon nanoparticles: Quantification of the concentration dependence of contrast enhancement for binding to sparse cellular epitopes," Ultrasound Med Biol., 2007, pp. 950-958, vol. 33, No. 6.
May et al., "Selective Inhibition of NF-κB Activation by a Peptide That Blocks the Interaction of NEMO with the IκB Kinase Complex," Science, 2000, pp. 1550-1554, vol. 289.
May et al., "Individualized antithrombotic therapy in high risk patients after coronary stenting. A double-edged sword between thrombosis and bleeding," Journal of Thrombosis and Haemostasis, 2008, pp. 487-493, vol. 99.
Montagne et al., "Preparation and characterization of narrow sized (o/w) magnetic emulsion," Journal of Magnetism and Magnetic Materials, 2002, pp. 302-312, vol. 250.
Moody et al., "Direct magnetic resonance imaging of carotid artery thrombus in acute stroke," The Lancet, 1999, pp. 122-123, vol. 353.
Morales et al., "Contrast agents for MRI based on iron oxide nanoparticles prepared by laser pyrolysis," Journal of Magnetism and Magnetic Materials, 2003, pp. 102-109, vol. 266.
Morawski et al., "Quantitative "Magnetic Resonance Immunohistochemistry" with Ligand-Targeted 19F Nanoparticles," Magnetic Resonance in Medicine, 2004, pp. 1255-1262, vol. 52.
Mulder et al., "Lipid-based nanoparticles for contrast-enhanced MRI and molecular imaging," NMR in Biomedicine, 2006, pp. 142-164, vol. 19.
Mulder et al., "MR molecular imaging and fluorescence microscopy for identification of activated tumor endothelium using a bimodal lipidic nanoparticle," The FASEB Journal, 2005, pp. 2008-2010, vol. 19.
Myerson et al., "'Thrombin sponge': A potent nanoparticle approach to inhibiting coagulation in acute thrombosis," The FASEB Journal, 2010, p. 574.2, vol. 24, No. 1.
Myerson et al., "Thrombin-inhibiting perfluorocarbon nanoparticles provide a novel strategy for treatment and magnetic resonance imaging of acute thrombosis," Journal of Thrombosis and Haemostasis, 2011, pp. 1292-1300, vol. 9, No. 7.
Myerson, J. et al., "Thrombin-Inhibiting Nanoparticles Rapidly Constitute Versatile and Detectable Anticlotting Surfaces," HHS Public Access Author Manuscript, Nanotechnology, Oct. 3, 2014, 21 pgs., vol. 25, No. 39.
Nelson, D. et al., Lehninger Principle of Biochemistry, 2000, Third Edition, Chapter 12, pp. 392-393, Worth Publishers, New York, New York.
Notice of Acceptance dated Apr. 20, 2016 from related Australian Patent Application No. 2010339809; 4 pgs.
Notice of Allowance dated Mar. 1, 2016 from related U.S. Appl. No. 12/682,098; 4 pgs.
Notice of Allowance dated Apr. 11, 2016 from related U.S. Appl. No. 13/641,252; 9 pgs.
Notice of Allowance dated Feb. 27, 2017 from related U.S. Appl. No. 13/516,528; 9 pgs.
Notice of Allowance dated Sep. 26, 2018 from related U.S. Appl. No. 15/179,626; 12 pgs.
Office Action dated Jun. 22, 2015 from related U.S. Appl. No. 12/682,098; 27 pgs.
Office Action dated May 9, 2013 from related U.S. Appl. No. 12/682,098; 17 pgs.
Office Action dated Jun. 11, 2012 from related U.S. Appl. No. 12/682,098; 15 pgs.
Office Action dated Jan. 14, 2013 from related U.S. Appl. No. 12/682,094; 16 pgs.
Office Action dated May 7, 2012 from related U.S. Appl. No. 12/682,094; 15 pgs.
Office Action dated Oct. 23, 2013 from related U.S. Appl. No. 13/516,528; 20 pgs.
Office Action dated May 27, 2014 from related U.S. Appl. No. 13/516,528; 7 pgs.
Office Action dated Dec. 9, 2014 from related U.S. Appl. No. 13/516,528; 6 pgs.
Office Action dated Sep. 14, 2015 from related U.S. Appl. No. 13/516,528; 11 pgs.
Office Action dated Apr. 8, 2016 from related U.S. Appl. No. 13/516,528; 10 pgs.
Office Action dated Nov. 3, 2016 from related U.S. Appl. No. 13/516,528; 13 pgs.
Office Action (Advisory) dated Feb. 23, 2015 from related U.S. Appl. No. 13/516,528; 3 pgs.
Office Action dated Sep. 30, 2015 from related U.S. Appl. No. 13/641,252; 20 pgs.
Office Action dated Jun. 26, 2015 from related U.S. Appl. No. 13/641,252; 11 pgs.
Office Action dated Dec. 10, 2015 from related Australian Patent Application No. 2010339809; 3 pgs.
Office Action dated Oct. 18, 2016 from related Canadian Patent Application No. 2,796,435; 3 pgs.
Office Action dated Jul. 20, 2011 from related Chinese Patent Application No. 200880117661.5; 11 pgs.
Office Action dated Jun. 4, 2012 from related Chinese Patent Application No. 200880117661.5; 17 pgs.
Office Action dated Jan. 7, 2013 from related Chinese Patent Application No. 200880117661.5; 13 pgs.
Office Action dated Jul. 25, 2013 from related Chinese Patent Application No. 200880117661.5; 13 pgs.
Office Action dated Dec. 4, 2013, from related Chinese Patent Application No. 201180029772.2; 13 pgs., with English translation.
Office Action dated Nov. 9, 2016 from related European Patent Application No. 10842655.2; 8 pgs.
Office Action dated Jun. 19, 2017 from related European Patent Application No. 10842655.2; 5 pgs.
Office Action dated Oct. 27, 2016 from related European Patent Application No. 11769698.9; 5 pgs.
Office Action dated Jan. 15, 2015 from related Japanese Patent Application No. 2013-505192; 2 pgs.
Office Action dated Jul. 10, 2017 from related U.S. Appl. No. 15/179,626; 22 pgs.
Office Action dated Sep. 12, 2017 from related Canadian Patent Application No. 2,796,435; 4 pgs.
Office Action dated Nov. 3, 2017 from related U.S. Appl. No. 15/179,626; 25 pgs.
Office Action dated Apr. 23, 2018 from related U.S. Appl. No. 15/179,626; 12 pgs.
Office Action dated Jun. 12, 2018 from related Canadian Patent Application No. 2,796,435; 3 pgs.
Pan, et al., "Water Soluble Nano-Bialys: Preparation of a Vascularly Constrained, Slow Releasing Nano-Carrier for Hydrophilic and Hydrophobic Drugs," American Chemical Society, Frontiers in Chemistry, Biopharmaceuticals & Biotechnology, Western Regional Meeting, Oct. 9-13, 2007, 1 pg.
Pan et al., "Lipid membrane editing with peptide cargo linkers in cells and synthetic nanostructures," FASEB J., Aug. 2010, pp. 2928-2937, vol. 24, No. 8.

(56) References Cited

OTHER PUBLICATIONS

Pan et al., "Anti-Angiogenesis Therapy in the Vx2 Rabbit Cancer Model with Lipase-cleavable Sn 2 Taxane Phospholipid Prodrug using [alpha]v[beta]3-Targeted Theranostic Nanoparticles," Theranostics, 2014, pp. 565-578, vol. 4, No. 6.
Partlow et al., "19F magnetic resonance imaging for stem/progenitor cell tracking with multiple unique perfluorocarbon nanobeacons," The FASEB Journal, 2007, pp. 1647-1654, vol. 21.
Pasparakis, "Regulation of tissue homeostasis by NF-κB signalling: implications for inflammatory diseases," Nature Reviews/Immunology, 2009, pp. 778-788, vol. 9.
Peters et al., "Targeting atherosclerosis by using modular, multifunctional micelles," PNAS, 2009, pp. 9815-9819, vol. 106, No. 24.
Petrasek et al., "Precise Measurement of Diffusion Coefficients using Scanning Fluorescence Correlation Spectroscopy," Biophysical Journal, 2008, pp. 1437-1448, vol. 94, No. 4.
Qiu et al., "Novel, Fluorescent, Magnetic, Polysaccharide-Based Microsphere for Orientation, Tracing, and Anticoagulation: Preparation and Characterization," Biomacromolecules, 2005, pp. 1041-1047, vol. 6, No. 2.
Raj et al., "Commercial Applications of Ferrofluids," Journal of Magnetism and Magnetic Materials, 1990, pp. 233-245, vol. 85.
Rhoades et al., "Quantification of α-Synuclein Binding to Lipid Vesicles Using Fluorescence Correlation Spectroscopy," Biophysical Journal, 2006, pp. 4692-4700, vol. 90, No. 12.
Roath, "Biological and biomedical aspects of magnetic fluid technology," Journal of Magnetism and Magnetic Materials, 1993, pp. 329-334, vol. 122.
Roger et al., "Some biomedical applications of ferrofluids," The European Physical Journal Applied Physics, 1999, pp. 321-325, vol. 5.
Acharyya, S. et al., "Interplay of IKK/NF-kB signaling in macrophages and myofibers promotes muscle degeneration in Duchenne muscular dystrophy," J. Clin. Invest., Apr. 2007, pp. 889-901, vol. 117, No. 4.
Ambrose, J. et al., "Angiographic Progression of Coronary Artery Disease and the Development of Myocardial Infarction," JACC, Jul. 1988, pp. 56-62, vol. 12, No. 1, American College of Cardiology.
Andersson, T. et al., "Heparin cofactor II activity in plasma: Application of an automated assay method to the study of a normal adult population," Scand. J. Haematol., 1986, pp. 96-102, vol. 36.
Angelova, M. et al., "Liposome Electroformation," Faraday Discuss. Chem. Soc., 1986, pp. 303-311, vol. 81.
Ansell, J. et al., "The Pharmacology and Management of the Vitamin K Antagonists," The Seventh ACCP Conference on Antithrombotic and Thrombolytic Therapy, Chest, Sep. 2004 Supplement, pp. 204S-233S, vol. 126, No. 3.
Bacia, K. et al., "Fluorescence Correlation Spectroscopy," Met. Mol. Biol., 2007, pp. 73-84, vol. 398, Humana Press Inc., Totowa, New Jersey.
Baud, V. et al., "Is NF-κB a good target for cancer therapy? Hopes and pitfalls," HAL Archives Ouvertes—France, Author Manuscript, pp. 1-17, Published in final edited form as: Nat. Rev. Drug Discov., Jan. 2009, pp. 33-40, vol. 8, No. 1.
Benson, R., "The Present Status of Coronary Arterial Disease," Archives of Pathology & Laboratory Medicine, 1926, pp. 876-916, vol. 2.
Bernal-Mizrachi, L. et al., "The role of NF-κB-1 and NF-κB-2-mediated resistance to apoptosis in lymphomas," PNAS, Jun. 13, 2006, pp. 9220-9225, vol. 103, No. 24.
Bertina, R. et al., "Hereditary Heparin Cofactor II Deficiency and the Risk of Development of Thrombosis," J. Thromb. Haemostasis, Jan. 8, 1987, pp. 196-200, vol. 57, No. 2, F.K. Schattauer Verlag GmbH (Stuttgart).
Bhoj, V. et al., "Ubiquitylation in innate and adaptive immunity," Nat., Mar. 26, 2009, pp. 430-437, vol. 458, Macmillan Publishers Limited.
Bibette, J., "Monodisperse ferrofluid emulsions," J. Magnetism and Magnetic Materials, 1993, pp. 37-41, vol. 122, Elsevier Science Publishers B.V.
Bidwell, G. III et al., "Therapeutic peptides for cancer therapy. Part I—peptide inhibitors of signal transduction cascades," Expert Opin. Drug Deliv., 2009, pp. 1033-1047, vol. 6, No. 10, Informa UK Ltd.
Bode, W. et al., "The refined 1.9 A crystal structure of human alpha-thrombin: interaction with D-Phe-Pro-Arg chloromethylketone and significance of the Tyr-Pro-Pro-Trp insertion segment," The EMBO J., Jun. 19, 1989, pp. 3467-3475, vol. 8, No. 11, IRL Press.
Bode, W. et al., "The refined 1.9-A X-ray crystal structure of D-Phe-Pro-Arg chloromethylketone-inhibited human alpha-thrombin: Structure analysis, overall structure, electrostatic properties, detailed active-site geometry, and structure-function relationships," Prot. Sci., 1992, pp. 426-471, vol. 1, Cambridge University Press, USA.
Bousser, "Antithrombotic Agents in the Prevention of Ischemic Stroke," Cerebrovascular Diseases, 2009, pp. 12-19, vol. 27 (Suppl. 3).
Bowen, "Particle Size Distribution Measurement from Millimeters to Nanometers and from Rods to Platelets," J. Disp. Sci. Technol., 2002, pp. 631-662, vol. 23, No. 5.
Boxus et al., "The HTLV-I Tax interactome," Retrovirology, 2008, pp. 76-99, vol. 5.
Bretschneider et al., "Evidence for functionally active protease-activated receptor-4 (PAR-4) in human vascular smooth muscle cells," British J. Pharmacol., 2001, pp. 1441-1446, vol. 132, No. 7.
Bretschneider et al., "Evidence for functionally active protease-activated receptor-3 (PAR-3) in human vascular smooth muscle cells," J. Thrombosis and Haemostasis, 2003, pp. 704-709, vol. 90.
Brown et al., "Incomplete lysis of thrombus in the moderate underlying atherosclerotic lesion during intracoronary infusion of streptokinase for acute myocardial infarction: quantitative angiographic observations," Circulation, 1986, pp. 653-661, vol. 73, No. 4.
Brownlie et al., "PEI-based vesicle-polymer hybrid gene delivery system with improved biocompatibility," Int. J. Pharmaceutics, 2004, pp. 41-52, vol. 274.
Caruthers et al., "Anti-angiogenic perfluorocarbon nanoparticles for diagnosis and treatment of atherosclerosis," WIREs Nanomedicine and Nanobiotechnology, 2009, pp. 311-323, vol. 1.
CAS Registry Record for Fumagillin (CAS # 23110-15-8). Entered STN Nov. 16, 1984, Accessed by Examiner on Mar. 8, 2016, 2 pgs.
CAS Registry Record for Fumagillol (CAS # 108102-51-8). Entered STN May 16, 1987, Accessed by Examiner on Mar. 8, 2016, 2 pgs.
Casscells et al., "Thermal detection of cellular infiltrates in living atherosclerotic plaques: possible implications for plaque rupture and thrombosis," Lancet, 1996, pp. 1447-1449, vol. 347.
Cerqueira, "Current Status of Radionuclide Tracer Imaging of Thrombi and Atheroma," Seminars in Nuclear Medicine, 1999, pp. 339-351, vol. 29, No. 4.
Charles, S., "Some Applications of Magnetic Fluids—Use as an Ink and in Microwave Systems," J. Magnetism and Magnetic Materials, 1987, pp. 350-358, vol. 65, Elsevier Science Publishers B.V., North-Holland, Amsterdam.
Cho et al., "Ability of Surfactant Micelles to Alter the Physical Location and Reactivity of Iron in Oil-in-Water Emulsion," Journal of Agricultural and Food Chemistry, 2002, pp. 5704-5710, vol. 50, No. 20.
Collen et al., "In vivo studies of a synthetic inhibitor of thrombin," J. Lab. Clin. Med., 1982, pp. 76-83, vol. 99, No. 1.
Connors, J., "Antidote for Factor Xa Anticoagulants," N. Engl. J. Med., Dec. 17, 2015, pp. 2471-2472, vol. 373, No. 25.
Constantinides, "Plaque Fissures in Human Coronary Thrombosis," Journal of Atherosclerosis Research, 1966, pp. 1-17, vol. 6.
Coughlin, "Thrombin signalling and protease-activated receptors," Nat., 2000, pp. 258-264, vol. 407.
Davies, "Anatomic Features in Victims of Sudden Coronary Death, Coronary Artery Pathology," Circulation, Supplement I, 1992, pp. I19-I24, vol. 85, No. 1.
Davies et al., "The effect of temperature and oleate adsorption on the growth of maghemite particles," Journal of Magnetism and Magnetic Materials, 1993, pp. 24-28, vol. 122.
De Korte et al., "Characterization of plaque components and vulnerability with intravascular ultrasound elastography," Phys. Med. Biol., 2000, pp. 1465-1475, vol. 45.

(56) References Cited

OTHER PUBLICATIONS

Deng et al., "Magnetic and conducting Fe3O4-cross-linked polyaniline nanoparticles with core-shell structure," Polymer, 2002, pp. 2179-2184, vol. 43.

Deng et al., "Preparation of magnetic polymeric particles via inverse microemulsion polymerization process," Journal of Magnetism and Magnetic Materials, 2003, pp. 69-78, vol. 257.

Di Cera, "Thrombin," Mol. Aspects Med., 2008, pp. 203-254, vol. 29, No. 4.

Dinisio, M. et al., "Drug Therapy—Direct Thrombin Inhibitors," N. Engl. J. Med., Sep. 8, 2005, pp. 1028-1040, vol. 353.

Dresco et al., "Preparation and Properties of Magnetite and Polymer Magnetite Nanoparticles," Langmuir, 1999, pp. 1945-1951, vol. 15, No. 6.

Dubertret et al., "In Vivo Imaging of Quantum Dots Encapsulated in Phospholipid Micelles," Science, 2002, pp. 1759-1762, vol. 298.

Duguid, "Thrombosis as a Factor in the Pathogenesis of Coronary Atherosclerosis," J Path Bact., 1946, pp. 207-212, vol. 58.

Duguid, "Thrombosis as a Factor in the Pathogenesis of Aortic Atherosclerosis," J Path Bact., 1948, pp. 57-61, vol. 60.

Extended European Search Report dated Jan. 2, 2014 from related European Patent Application No. EP 08837973.0; 9 pgs.

Extended European Search Report dated May 6, 2014 from related European Patent Application No. 11769698.9; 8 pgs.

Extended European Search Report dated May 27, 2015 from related European Patent Application No. 10842655; 12 pgs.

Fareed et al., "Changing trends in anti-coagulant therapies. Are heparins and oral anti-coagulants challenged?," International Journal of Angiology, 2008, pp. 176-192, vol. 27, No. 3.

Feltin et al., "New Technique for Synthesizing Iron Ferrite Magnetic Nanosized Particles," Langmuir, 1997, pp. 3927-3933, vol. 13, No. 15.

Flacke et al., "Novel MRI Contrast Agent for Molecular Imaging of Fibrin: Implications for Detecting Vulnerable Plaques," Circulation, 2001, pp. 1280-1285, vol. 104.

\* cited by examiner

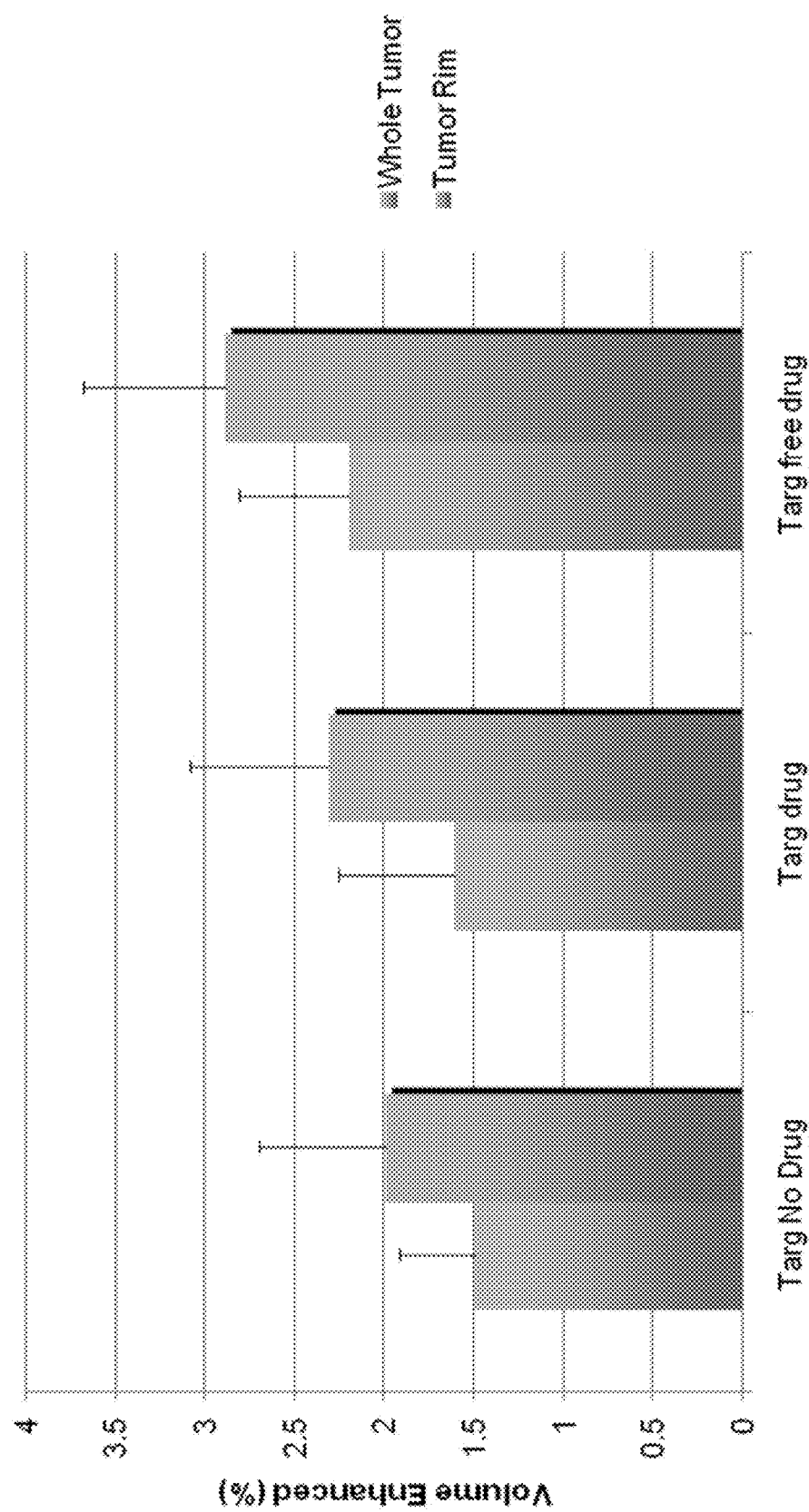

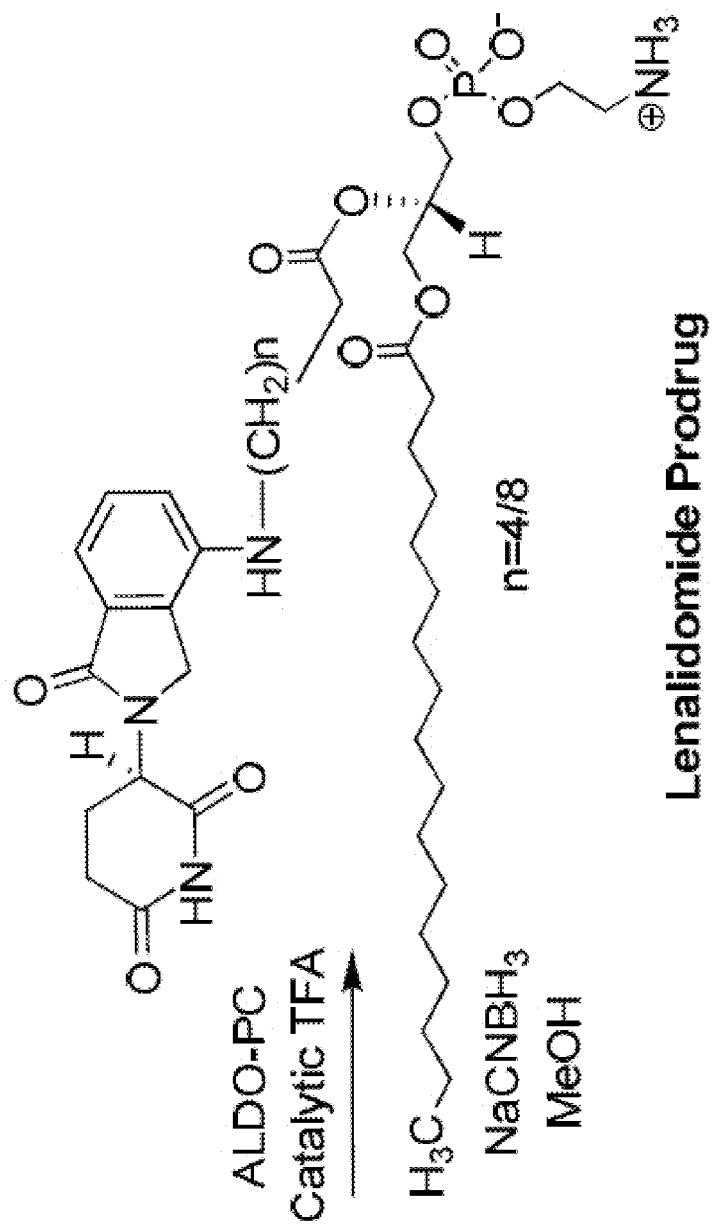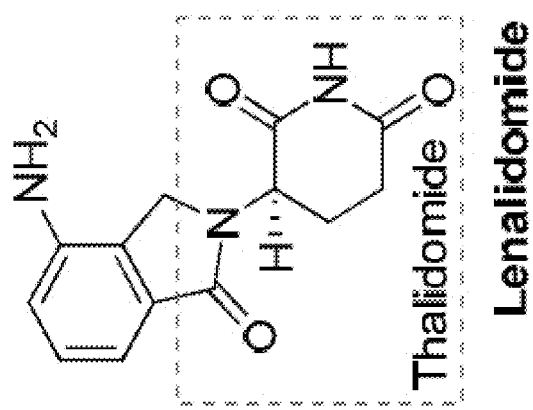
FIG. 15

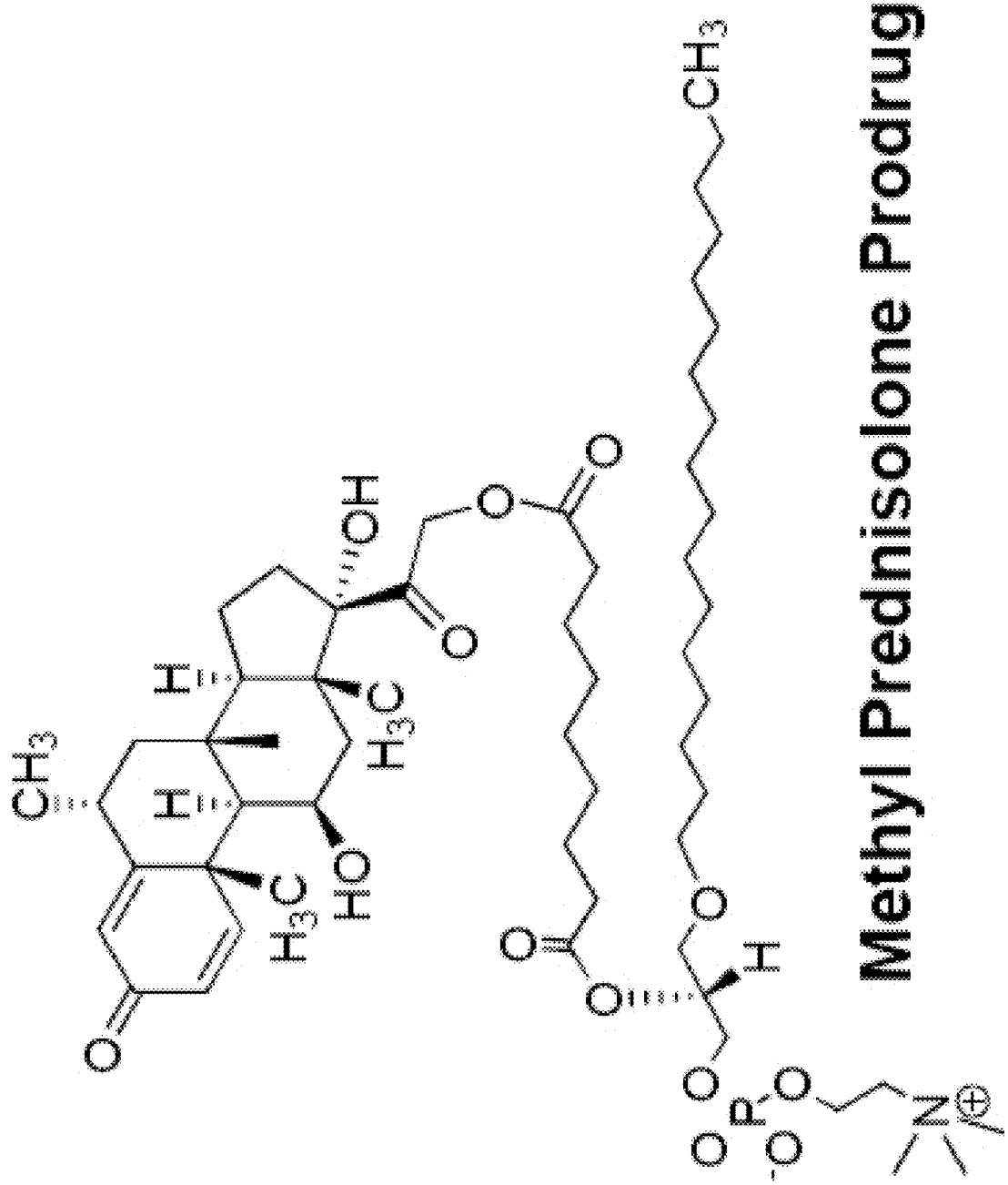
FIG. 31 Methyl Prednisolone Prodrug

Camptothecin Prodrug 1

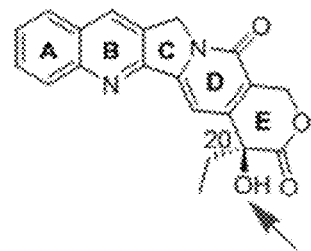
Camptothecin (CPT)
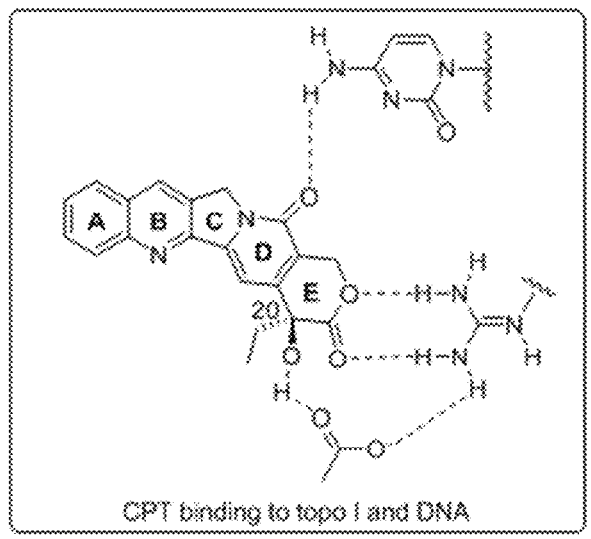
CPT binding to topo I and DNA
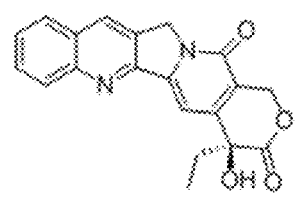
Camptothecin (CPT)
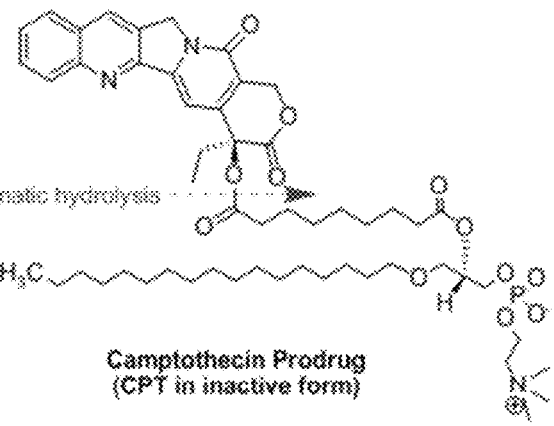
Camptothecin Prodrug
(CPT in inactive form)
FIG. 32B

PRODRUG COMPOSITIONS, PRODRUG NANOPARTICLES, AND METHODS OF USE THEREOF

CROSS REFERENCE TO RELATED APPLICATIONS

This application is a continuation of U.S. application Ser. No. 15/179,626, filed Jun. 10, 2016, which is a divisional of U.S. application Ser. No. 13/641,252, filed Jan. 29, 2013, which is a US National of PCT Application PCT/US2011/032744, which claims the priority of U.S. provisional Application No. 61/324,464, filed Apr. 15, 2010, each of which is hereby incorporated by reference in its entirety.

GOVERNMENTAL RIGHTS

This invention was made with government support under AR056468, HL094470, CA119342, CA100623 and CA216840 awarded by the National Institutes of Health. The government has certain rights in the invention.

FIELD OF THE INVENTION

The present invention encompasses prodrug compositions, nanoparticles comprising one or more prodrugs, and methods of use thereof.

REFERENCE TO SEQUENCE LISTING

A paper copy of the sequence listing and a computer readable form of the same sequence listing are appended below and herein incorporated by reference. The information recorded in computer readable form is identical to the written sequence listing, according to 37 C.F.R. 1.821(f).

BACKGROUND OF THE INVENTION

Known active compounds with in vitro activity may not be accessible for in vivo therapy because of difficulties in delivery of these compounds. For instance, the compound may have a short in vivo half-life, rendering the compound practically useless in vivo. Similarly, a compound may be unstable in vivo, converting to an inactive compound under physiological conditions. Or alternatively, a compound may be associated with significant toxicity, rendering its in vivo use difficult. There is a need, therefore, for a method of delivering these active compounds that both maintains the activity of the compound in vivo, and directs delivery to a desired target cell, avoiding potential toxicity.

SUMMARY OF THE INVENTION

One aspect of the present invention encompasses a composition for in vivo delivery of a compound to a target cell. The composition comprises a non-liposomal particle and at least one prodrug. The outer surface of the particle is a membrane comprised of the at least one prodrug, and is further comprised of about 100% to about 60% phospholipid, wherein the outer surface of the particle is capable of fusing to the outer leaflet of the target cell membrane in vivo, such fusion resulting in transfer of the prodrug from the particle to the outer leaflet of the target cell. The prodrug comprises a compound of less than about 3000 da linked to an acyl moiety of a phosphoglyceride, wherein the compound may be released from the phosphoglyceride backbone via enzyme cleavage. The prodrug substantially remains in the outer surface membrane of the particle until transfer of the prodrug to the outer leaflet of the target cell, and the prodrug is further transferred from the outer leaflet to the inner leaflet of the target cell membrane, resulting in release of the compound intracellularly via cleavage of the enzyme cleavable linkage.

Another aspect of the invention encompasses a method for in vivo delivery of a compound to a target cell. The method comprises administering a composition to a subject, the composition comprising a non-liposomal particle and at least one prodrug in a pharmaceutically acceptable carrier. The outer surface of the particle is a membrane comprised of the at least one prodrug, and is further comprised of about 100% to about 60% phospholipid, wherein the outer surface of the particle is capable of fusing to the outer leaflet of the target cell membrane in vivo, such fusion resulting in transfer of the prodrug from the particle to the outer leaflet of the target cell. The prodrug comprises a compound of less than about 3000 da linked to an acyl moiety of a phosphoglyceride, wherein the compound may be released from the phosphoglyceride backbone via enzyme cleavage. The prodrug substantially remains in the outer surface membrane of the particle until transfer of the prodrug to the outer leaflet of the target cell, and the prodrug is further transferred from the outer leaflet to the inner leaflet of the target cell membrane, resulting in release of the compound intracellularly via cleavage of the enzyme cleavable linkage.

Other aspects and iterations of the invention are discussed in more detail below.

BRIEF DESCRIPTION OF THE FIGURES

FIG. 4A-B depicts two micrographs. The micrographs illustrate (A) non-significant change in angiogenesis contrast enhancement at 1.5 T with non-prodrug paclitaxel, and (B) the angiogenic response to paclitaxel prodrugs incorporated into integrin targeted PFC nanoparticles in the vx2 tumor model (n=2/group) in rabbit.

FIG. 15 depicts the synthesis scheme of lenalidomide prodrugs.

FIG. 31 depicts a prodrug comprising methyl prednisolone.

FIG. 32A-B depicts a prodrug comprising camptothecin (A) and a scheme for synthesizing a campothecin prodrug (B).

DETAILED DESCRIPTION OF THE INVENTION

Figure 1A:
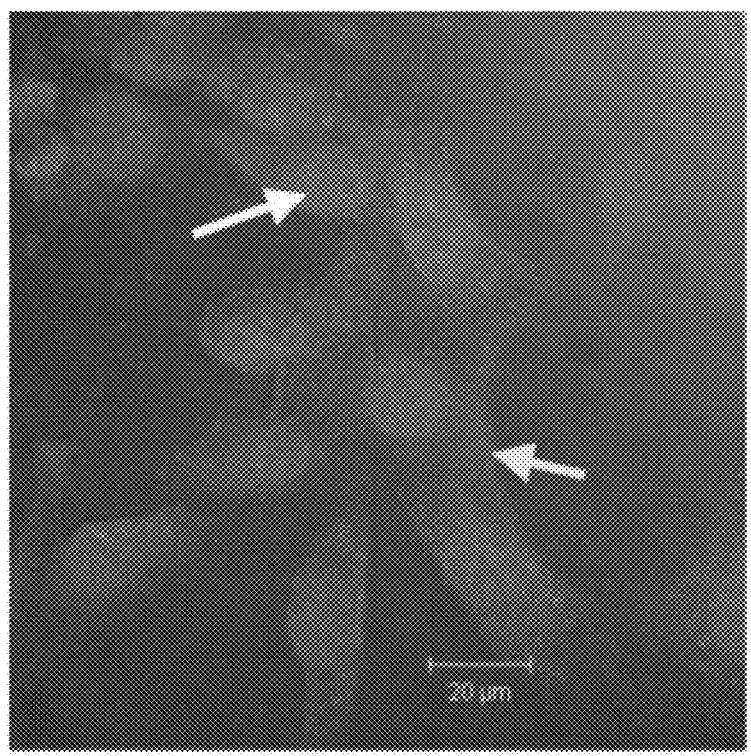
FIG. 1A-B depicts light microscopy images of cells. The cells are treated with (A) doxorubicin delivered by prodrugs and (B) free doxorubicin drug.

The present invention provides one or more prodrug compositions, particles comprising one or more prodrugs, and methods of use thereof. Advantageously, the invention provides compositions and methods for in vivo delivery of a compound to a target cell.

In one aspect, the present invention encompasses a drug delivery system that comprises a prodrug (described in section I below) embedded in a non-liposomal nanoparticle (described in Section II below). The nanoparticle may further optionally comprise a homing ligand as described herein. The drug delivery system allows intracellular delivery of the prodrug while protecting the prodrug from physiological conditions that may inactive the drug.

I. Prodrug Composition

Generally speaking, a prodrug of the invention encompasses a compound linked to an acyl moiety of a phosphoglyceride. Suitable phosphoglycerides may include phosphatidyl choline, phosphatidyl ethanolamine, phosphatidyl inositol, and phosphatidyl serine. A compound may be linked to either position in a phosphoglyceride. For instance, a compound may be linked to the sn1 position or the sn2 position of a phosphoglyceride. In a preferred embodiment, the compound is linked to the sn2 position.

(a) Suitable Compounds

Generally speaking a suitable compound of the invention is less than 3000 da. In one embodiment, a compound is less than about 3000, 2900, 2800, 2700, 2600, 2500, 2400, 2300, 2200, 2100, 2000, 1900, 1800, 1700, 1600, 1500, 1400, 1300, 1200, 1100, 1000, 900, 800, 700, 600, 500, 400, 300, 200, or 100 da. In another embodiment, a compound is between about 2500 da and about 200 da. In yet another embodiment, a compound is between about 2000 da and about 200 da. In some embodiments, a compound may be larger than 3000 da, as long as the prodrug comprising the compound maintains the ability to transfer from the outer leaflet of a cell membrane to the inner leaflet of a cell membrane.

Typically, a suitable compound comprises a reactive group outside the active site of the compound. This reactive site allows the linkage of the compound to the glyceride backbone as described below. A suitable compound of the invention may typically be selected from the group comprising a small molecule, a metal atom, an organometallic complex, a radioactive compound, an amino acid polymer (e.g. a protein, a peptide, etc.), a carbohydrate, a lipid, a nucleic acid polymer, or a combination thereof. Generally speaking, a suitable compound may be linked to a phosphoglyceride as described herein. Once the compound is cleaved from the glyceride backbone, the released form may be an active compound or a pre-active compound. A compound may be derivatized to enhance a desired property of the compound. Methods for derivatizing a compound are known in the art.

In some embodiments, for instance, a compound may be a drug, a therapeutic compound, a steroid, a nucleic acid based material, or derivatives, analogues, or combinations thereof, in their native form or derivatized with hydrophobic or charged moieties to enhance incorporation or adsorption to a nanoparticle. Such compounds may be water soluble or may be hydrophobic. Non-limiting examples of compounds may include immune-related agents, thyroid agents, respiratory products, antineoplastic agents, anti-helmintics, anti-malarials, mitotic inhibitors, hormones, anti-protozoans, anti-tuberculars, cardiovascular products, blood products, biological response modifiers, anti-fungal agents, vitamins, peptides, anti-allergic agents, anti-coagulation agents, circulatory drugs, metabolic potentiators, anti-virals, anti-anginals, antibiotics, anti-inflammatories, anti-rheumatics, narcotics, cardiac glycosides, neuromuscular blockers, sedatives, local anesthetics, general anesthetics, or radioactive atoms or ions. In certain embodiments, a compound is an aptamer, or a nucleic acid derivative, such as peptide nucleic acid (PNA) or locked nucleic acid (LNA).

In an exemplary embodiment, the compound may be doxorubicin, paclitaxel, taxol, lenalidomide, methotrexate, bortezomib, a myc-inhibitor, lenalidomide, cis platin, methyl prednisolone, fumagillin, camptothecin, a peptide nucleic acid, a PDT drug, or a derivative or analogue thereof that retains pharmaceutical activity. In one embodiment, the compound may be an analogue of fumagillin. In some embodiments, an analogue of fumagillin is selected from the analogues detailed in Example 12. In other embodiments, the compound may be a PDT drug, such as the prodrug of formula XI. Additional suitable PDT drugs are known in the art, and may include porfimer sodium, aminolevulinic acid, and methyl ester of aminolevulinic acid.

In other exemplary embodiments, the compound may be selected from a compound listed in Table A below.

TABLE A

Non-limiting Examples of Compounds

| Category of compound | Non-limiting examples |
| --- | --- |
| Immune-related agents | immune serums, antitoxins, antivenoms bacterial vaccines, viral vaccines, rabies prophylaxis products |
| thyroid agents | iodine products and anti-thyroid agents |
| respiratory products | xanthine derivatives theophylline and aminophylline |
| antineoplastic agents | platinum compounds (e.g., spiroplatin, cisplatin, and carboplatin), methotrexate, fluorouracil, adriamycin, mitomycin, ansamitocin, bleomycin, cytosine arabinoside, arabinosyl adenine, mercaptopolylysine, vincristine, busulfan, chlorambucil, melphalan (e.g., PAM, L-PAM or phenylalanine mustard), mercaptopurine, mitotane, procarbazine hydrochloride dactinomycin (actinomycin D), daunorubicin hydrochloride, doxorubicin hydrochloride, paclitaxel and other taxanes, rapamycin, manumycin A, TNP-470, plicamycin (mithramycin), aminoglutethimide, estramustine phosphate sodium, flutamide, leuprolide acetate, megestrol acetate, |

TABLE A-continued

Non-limiting Examples of Compounds

| Category of compound | Non-limiting examples |
| --- | --- |
| | tamoxifen citrate, testolactone, trilostane, amsacrine (m-AMSA), asparaginase (L-asparaginase) Erwina asparaginase, interferon α-2a, interferon α-2b, teniposide (VM-26), vinblastine sulfate (VLB), vincristine sulfate, bleomycin sulfate, hydroxyurea, procarbazine, and dacarbazine |
| anti-helmintics | pyrantel pamoate, piperazine, tetrachloroethylene, thiabendazole, niclosamide |
| antimalarials | Chloroquine, amodiaquine, antifolate drugs, proguanil (chloroguanide), mefloquine, quinine, halofantrine, artemesinin and derivaties, primaquine, doxycycline, tetracycline, and clindamycin |
| mitotic inhibitors | etoposide, colchicine, and the vinca alkaloids |
| hormones | androgens, progestins, estrogens and antiestrogens, growth hormone, melanocyte stimulating hormone, estradiol, beclomethasone dipropionate, betamethasone, betamethasone acetate and betamethasone sodium phosphate, vetamethasone disodium phosphate, vetamethasone sodium phosphate, cortisone acetate, dexamethasone, dexamethasone acetate, dexamethasone sodium phosphate, flunisolide, hydrocortisone, hydrocortisone acetate, hydrocortisone cypionate, hydrocortisone sodium phosphate, hydrocortisone sodium succinate, methylprednisolone, methylprednisolone acetate, methylprednisolone sodium succinate, paramethasone acetate, prednisolone, prednisolone acetate, prednisolone sodium phosphate, prednisolone tebutate, prednisone, triamcinolone, triamcinolone acetonide, triamcinolone diacetate, triamcinolone hexacetonide, fludrocortisone acetate, oxytocin, vassopressin, glucagon and their derivatives |
| antiprotozoans | chloroquine, hydroxychloroquine, metronidazole, quinine and meglumine antimonite |
| antituberculars | para-aminosalicylic acid, isoniazid, capreomycin sulfate cycloserine, ethambutol hydrochloride ethionamide, pyrazinamide, rifampin, and streptomycin sulfate |
| cardiovascular products | chelating agents and mercurial diuretics and cardiac glycosides |
| blood products | parenteral iron, hemin, hematoporphyrins and their derivatives |
| biological response modifiers | muramyldipeptide, muramyltripeptide, microbial cell wall components, lymphokines (e.g., bacterial endotoxin such as lipopolysaccharide, macrophage activation factor), sub-units of bacteria (such as Mycobacteria, Corynebacteria), the synthetic dipeptide N-acetyl-muramyl-L-alanyl-D-isoglutamine |
| anti-fungal agents | ketoconazole, nystatin, griseofulvin, flucytosine (5-fc), miconazole, amphotericin B, ricin, cyclosporins, and β-lactam antibiotics (e.g., sulfazecin) |
| vitamins | cyanocobalamin neinoic acid, retinoids and derivatives such as retinol palmitate, and α-tocopherol |
| peptides | manganese super oxide dismutase; enzymes such as alkaline phosphatase |
| anti-allergic agents | Amelexanox |
| anti-coagulation agents | phenprocoumon and heparin |
| circulatory drugs | Propranolol |
| metabolic potentiators | Glutathione |

TABLE A-continued

Non-limiting Examples of Compounds

| Category of compound | Non-limiting examples |
|---|---|
| antivirals | acyclovir, amantadine azidothymidine (AZT, DDI, Foscarnet, or Zidovudine), ribavirin and vidarabine monophydrate (adenine arabinoside, ara-A) |
| antianginals | diltiazem, nifedipine, verapamil, erythritol tetranitrate, isosorbide dinitrate, nitroglycerin (glyceryl trinitrate) and pentaerythritol tetranitrate |
| antibiotics | dapsone, chloramphenicol, neomycin, cefaclor, cefadroxil, cephalexin, cephradine erythromycin, clindamycin, lincomycin, amoxicillin, ampicillin, bacampicillin, carbenicillin, dicloxacillin, cyclacillin, picloxacillin, hetacillin, methicillin, nafcillin, oxacillin, penicillin including penicillin G and penicillin V, ticarcillin rifampin, aminoglycosides and tetracycline |
| antiinflammatories | diflunisal, ibuprofen, indomethacin, meclofenamate, mefenamic acid, naproxen, oxyphenbutazone, phenylbutazone, piroxicam, sulindac, tolmetin, aspirin and salicylates |
| antirheumatics | Adalimumab, azathioprine, chloroquine and hydroxychloroquine (antimalarials), cyclosporine (Cyclosporin A), D-penicillamine, etanercept, gold salts (sodium aurothiomalate, auranofin), infliximab, leflunomide, methotrexate, minocycline (a tetracycline antibiotic), sulfasalazine |
| narcotics | Paregoric, opiates, codeine, heroin, methadone, morphine and opium |
| cardiac glycosides | deslanoside, digitoxin, digoxin, digitalin and digitalis |
| neuromuscular blockers | atracurium mesylate, gallamine triethiodide, hexafluorenium bromide, metocurine iodide, pancuronium bromide, succinylcholine chloride (suxamethonium chloride), tubocurarine chloride and vecuronium bromide |
| sedatives (hypnotics) | amobarbital, amobarbital sodium, aprobarbital, butabarbital sodium, chloral hydrate, ethchlorvynol, ethinamate, flurazepam hydrochloride, glutethimide, methotrimeprazine hydrochloride, methyprylon, midazolam hydrochloride, paraldehyde, pentobarbital, pentobarbital sodium, phenobarbital sodium, secobarbital sodium, talbutal, temazepam and triazolam |
| local anesthetics | bupivacaine hydrochloride, chloroprocaine hydrochloride, etidocaine hydrochloride, lidocaine hydrochloride, mepivacaine hydrochloride, procaine hydrochloride and tetracaine hydrochloride |
| general anesthetics | droperidol, etomidate, fentanyl citrate with droperidol, ketamine hydrochloride, methohexital sodium and thiopental sodium |
| radioactive particles or ions | strontium, iodide rhenium, yttrium, and radiopharmaceuticals, such as radioactive iodine and phosphorus product |

(b) Linkage

A prodrug of the invention encompasses a compound, as defined in section I(a) above, linked to a phosphoglyceride. The linkage between the glyceride backbone and the compound may be any suitable linkage known in the art. In exemplary embodiments, suitable linkages may comprise carbon, oxygen, nitrogen, or a combination thereof.

The linkage may comprise at least one, two, three, four, five, six, seven, eight, nine, ten, eleven, twelve, thirteen, fourteen, fifteen, sixteen, seventeen, eighteen, nineteen, twenty, or more than twenty atoms, counted from the glyceride backbone. In an exemplary embodiment, the linkage comprises at least five atoms, counted from the glyceride backbone.

Generally speaking, the linkage is selected so that the sn2 position of the glyceride backbone is cleavable by an enzyme. Typically, such an enzyme may be found intracellularly.

In addition, the linkage itself may be enzyme cleavable. In an exemplary embodiment, the linkage may be cleaved by an intracellular enzyme. In several embodiments, either the glyceride sn2 position or the linkage may be cleaved by a lipase. For instance, in one embodiment the lipase may be a phospholipid $A_2$ lipase (also known as phospholipase $A_2$). In another embodiment, the lipase may be a phospholipid $A_1$ lipase (also known as phospholipase $A_1$). In yet another embodiment, the lipase may be a phospholipase B enzyme. In each of the above embodiments, the enzyme is capable of cleaving the linkage and thereby releasing the compound from the linkage.

(c) Released Form of a Compound

When a prodrug of the invention is cleaved from the glyceride backbone, a released form of a compound is created. The released form may either be an active compound or a pre-active compound. As used herein, an "active compound" is a compound that exerts a pharmaceutical effect on the cell. Such an active compound may comprise the linkage defined in section I(b) above, or a portion thereof. An "active compound" may also be a metabolite of the compound used to create the prodrug.

A pre-active compound, as used herein, is a compound that requires enzyme activation to become an active compound as defined above. For instance, a pre-active compound of the invention may comprise a compound defined in section I(a) above and a linkage defined in section I(b) above, or a portion thereof. The linkage may comprise an enzyme recognition site within the linkage, or between the linkage and the compound. Generally speaking, an enzyme binds to the enzyme recognition site and cleaves the linkage, such that the linkage, or a portion thereof, is removed from the pre-active compound to produce an active compound, as defined above. In an alternative embodiment, the active compound may be metabolite of the pre-active compound.

(d) Nanoparticle Comprising a Prodrug

In exemplary embodiments of the application, a prodrug is included in a nanoparticle. In such embodiments, the prodrug is substantially not released from the nanoparticle until after the fusion of the nanoparticle with the target cell membrane. In an exemplary embodiment, the prodrug is substantially not released from the nanoparticle until after the fusion of the nanoparticle with the outer leaflet of a target cell membrane. Such fusion is described in more detail below. Briefly, however, the fusion of a nanoparticle with a target cell membrane allows lipid transfer between the nanoparticle and the target cell membrane. For example, in some instances, the lipid membrane of a nanoparticle may fuse with the outer leaflet of the lipid membrane of a target cell membrane, allowing transfer of nanoparticle derived lipids and/or a prodrug to the target cell membrane.

After fusion and the subsequent transfer of the prodrug from the nanoparticle to the target cell, the prodrug may be cleaved, detaching the released form of the compound from the glyceride backbone. Generally speaking, this cleavage occurs after transfer of the prodrug from the outer leaflet of the target cell membrane to the inner leaflet. This results in the compound being substantially released intracellularly. The released compound may comprise the linkage or a portion thereof as described above. For more details, see section II below and the examples.

(e) Exemplary Examples

In an exemplary embodiment, a prodrug of the invention comprises a prodrug of formula I, II, III, IV, V, VI, VII, VIII, IX, X, XI, XII, XIII, XIV, XV, XVI, XVII, XVIII or XIX. In another exemplary embodiment, a prodrug of the invention comprises a prodrug consisting of formula I, II, III, IV, V, VI, VII, VIII, IX, X, XI, XII, XIII, XIV, XV, XVI, XVII, XVIII or XIX. In yet another exemplary embodiment, a prodrug of the invention comprises a prodrug of formula I, II, III, IV, V, VI, VII, VIII, IX, X, XI, XII, XIII, XIV, XV, XVI, XVII, XVIII or XIX, wherein the compound is further derivatized in a manner that does not significantly alter the function of the prodrug. In still another exemplary embodiment, a prodrug of the invention comprises a prodrug of formula I, II, III, IV, V, VI, VII, VIII, IX, X, XI, XII, XIII, XIV, XV, XVI, XVII, XVIII or XIX, wherein the phosphoglyceride backbone is further derivatized in a manner that does not significantly alter the function of the prodrug.

In each of the above exemplary embodiments, a prodrug of formula I, II, III, IV, V, VI, VII, VIII, IX, X, XI, XII, XIII, XIV, XV, XVI, XVII, XVIII or XIX may have a linkage between the glyceride backbone and the compound that may vary in the number of atoms represented in the formula. For instance, the linkage may be 1, 2, 3, 4, 5, 6, 7, or more than 7 atoms in length for formulas I, II, III, IV, V, VI, VII, VIII, IX, X, XI, XII, XIII, XIV, XV, XVI, XVII, XVIII or XIX.

TABLE B

Exemplary prodrugs

| Formula No. | Structure |
|---|---|
| I | 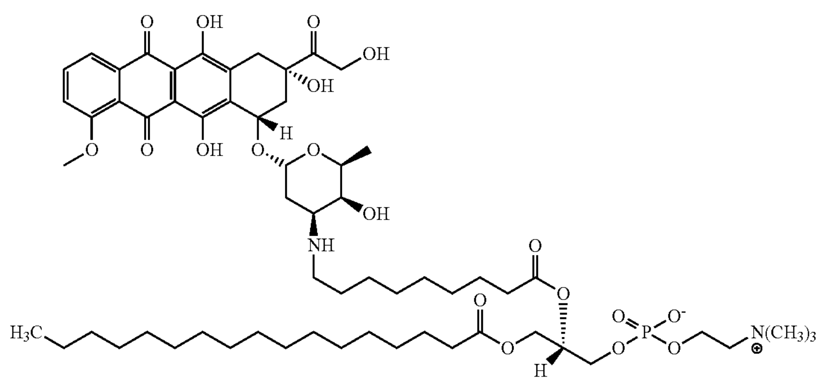 |
| II | 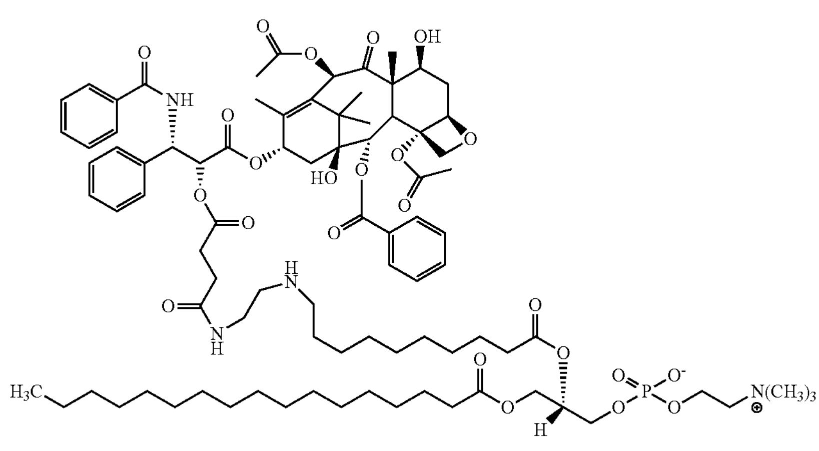 |

TABLE B-continued
Exemplary prodrugs
| Formula No. | Structure |
|---|---|
| III | 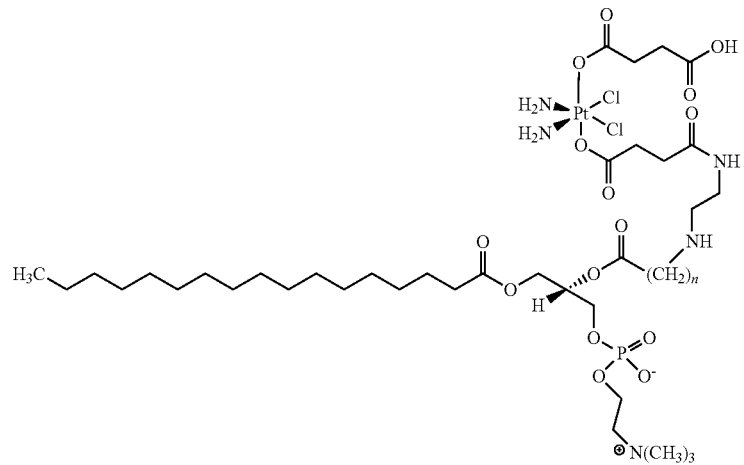 |
| IV | 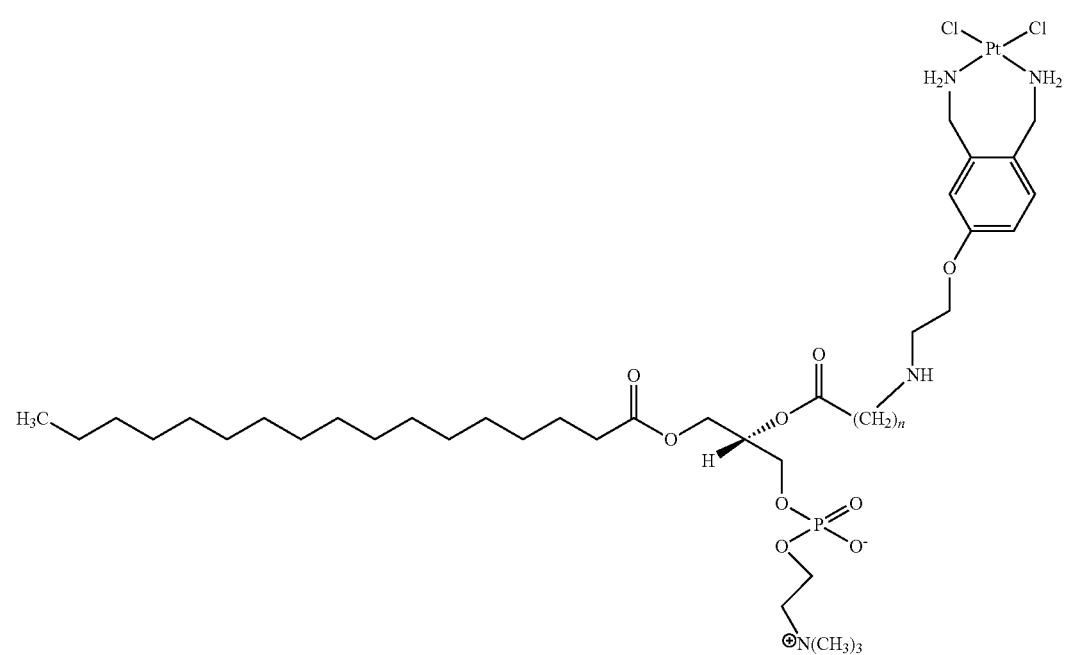 |

TABLE B-continued

Exemplary prodrugs

| Formula No. | Structure |
|---|---|
| V | (structure image) |
| VI | (structure image) |
| VII | (structure image) |

TABLE B-continued

Exemplary prodrugs

| Formula No. | Structure |
|---|---|
| VIII | 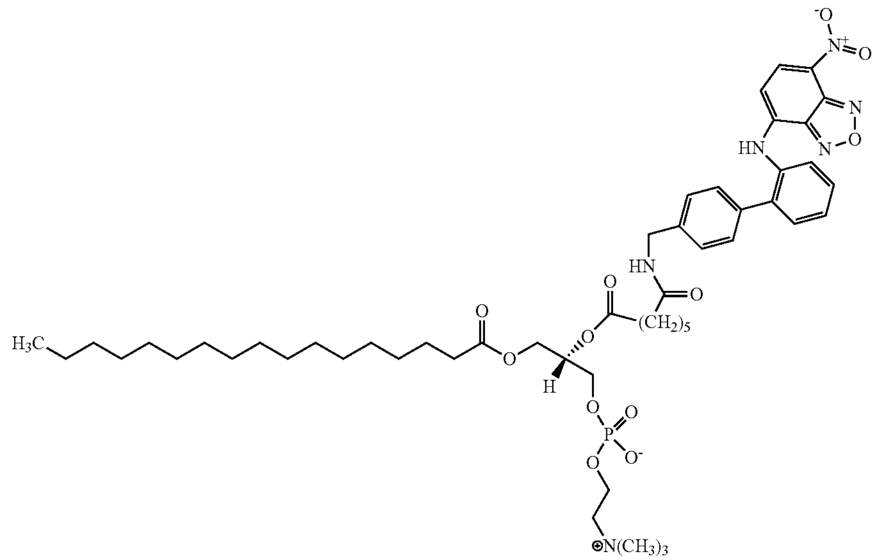 |
| IX | 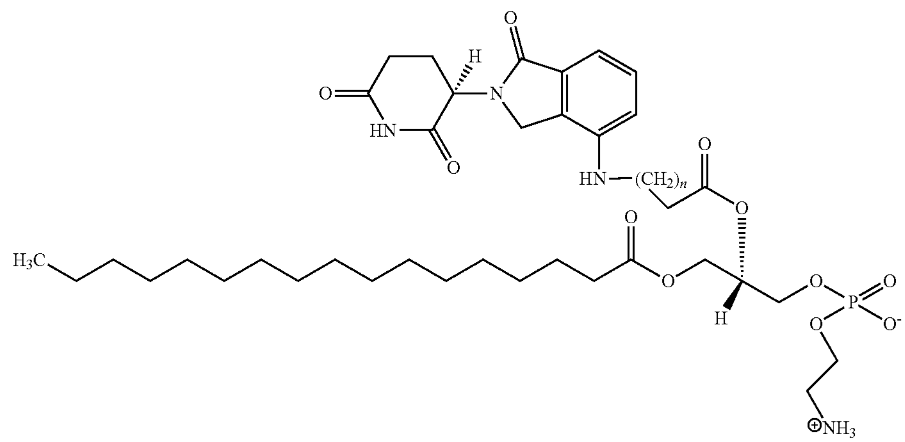 |
| X | 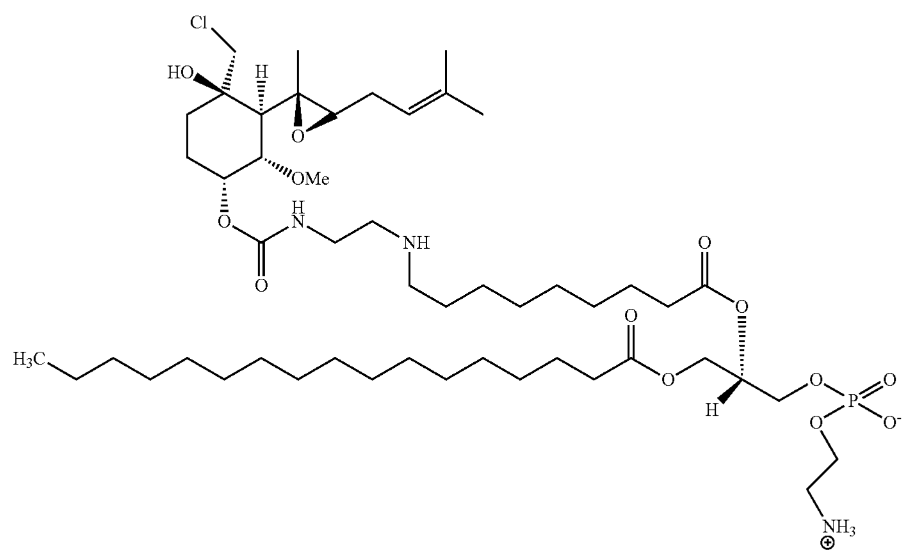 |

TABLE B-continued

Exemplary prodrugs

| Formula No. | Structure |
|---|---|
| XI | 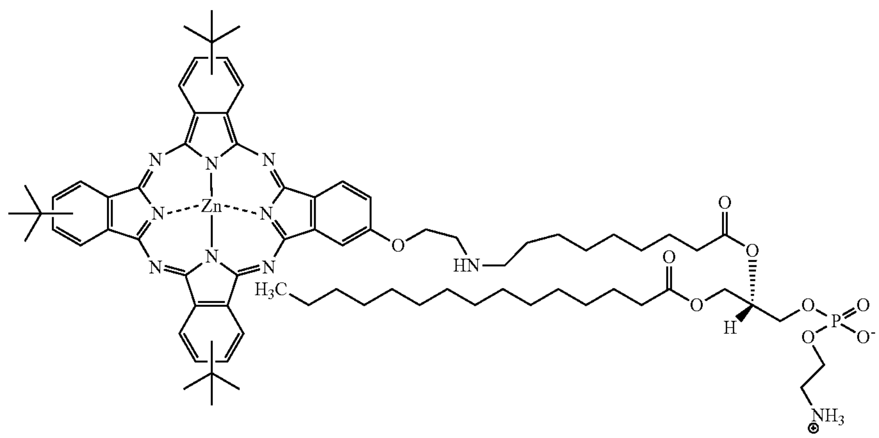 |
| XII | 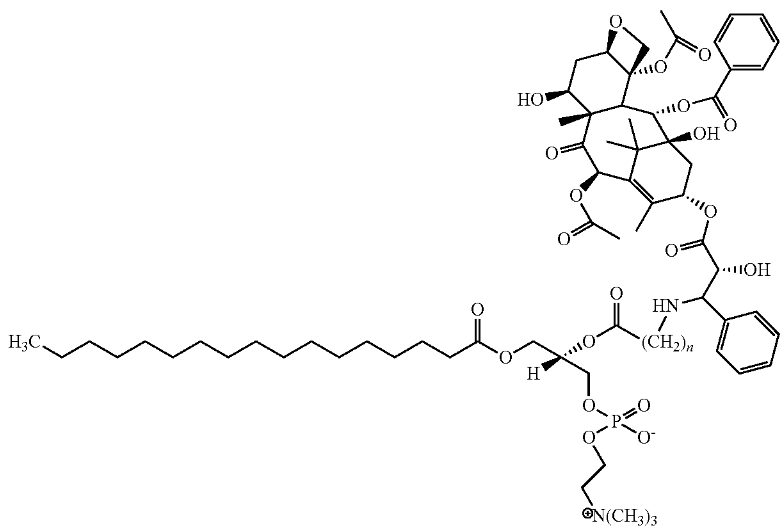 |
| XIII | 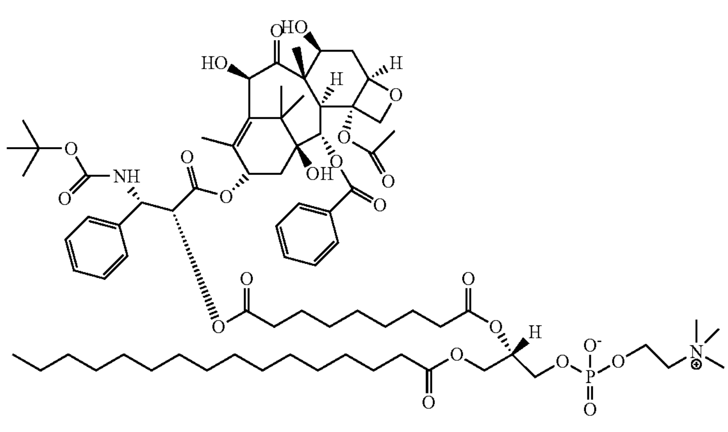 |

TABLE B-continued
Exemplary prodrugs
| Formula No. | Structure |
|---|---|
| XIV | 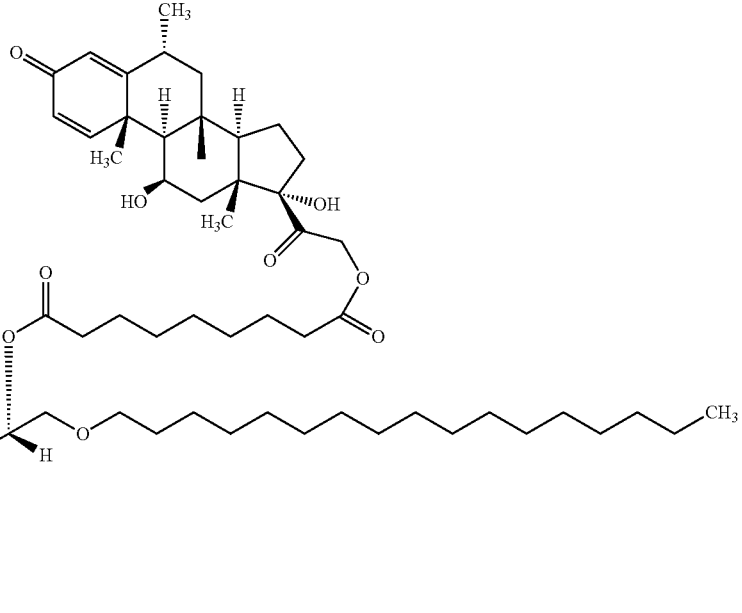 |
| XV | 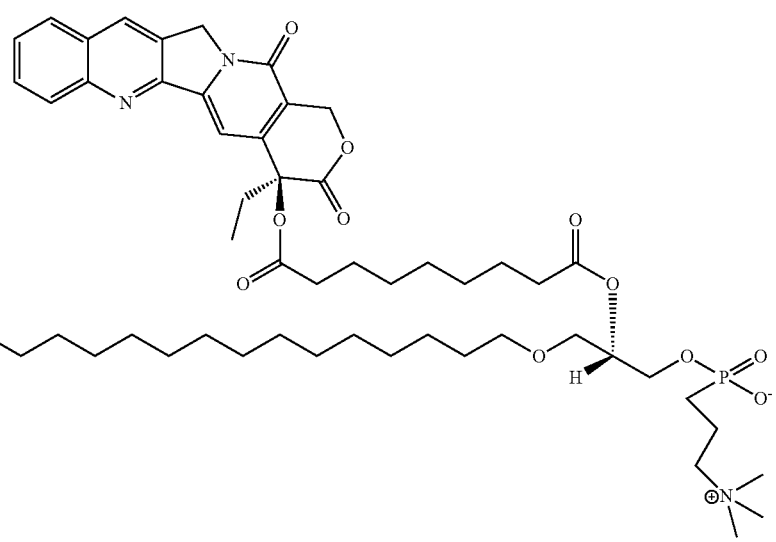 |
| XVI | 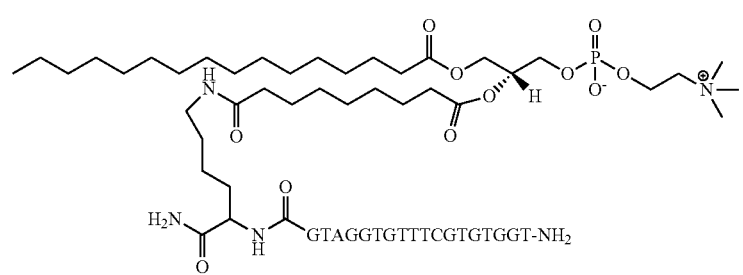 |

TABLE B-continued

Exemplary prodrugs

| Formula No. | Structure |
|---|---|
| XVII | [chemical structure showing a phospholipid conjugate with peptide sequence ACCACACGAAACACCTAC-HH₂] |
| XVIII | [chemical structure of an epoxide-containing natural product linked via diester to an ether phospholipid with phosphocholine headgroup] |
| XIX | [chemical structure of camptothecin derivative linked via carbamate and amide to an ether phospholipid with aminopropyl phosphate headgroup] |

II. Nanoparticle

A nanoparticle of the invention comprises a prodrug, as discussed in section I above, and an amphiphilic membrane. In some embodiments, the amphiphilic membrane comprises a prodrug. The membrane is stable in vivo for at least the time required for the particle to fuse with a target cell membrane, and transfer the prodrug to the target cell membrane.

Advantageously, a nanoparticle of the invention may protect a highly labile compound from in vivo inactivation.

This is due, in part, to the sequestration of the compound, in the form of a prodrug, in the amphiphilic membrane. The membrane protects the compound from hydrolysis and from inactivation due to physiological conditions, such as pH or enzyme cleavage. This allows the delivery of an active compound to a cell, extending the half-life of a compound in vivo, thereby enhancing the pharmacokinetic and pharmacodynamic properties of the compound. As a result, a compound with little previous in vivo efficacy may become a viable in vivo treatment option when formulated as a prodrug and incorporated in a nanoparticle described herein.

Usually, a nanoparticle of the invention may be about 10 nm to about 10 µm. In some embodiments, a nanoparticle may be about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 nm. In other embodiments, a nanoparticle may be about 1, 1.25, 1.5, 1.75, 2, 2.25, 2.5, 2.75, 3, 3.25, 3.5, 3.75, 4, 4.25, 4.5, 4.75, 5, 5.25, 5.5, 5.75, or 6 µm. In yet another embodiment, a nanoparticle of the invention may be less than 100 nm. In still another embodiment, a nanoparticle may be less than 200 nm.

(a) Nanoparticle Amphiphilic Membrane

A nanoparticle of the invention comprises an amphiphilic membrane. Generally speaking, the amphiphilic membrane may be comprised of between 100% and 50% of an amphiphilic lipid, e.g. a phospholipid. In some embodiments, the membrane is comprised of about 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, or 50% phospholipid.

The composition of the amphiphilic membrane can vary, but typically comprises between about 0.1% to about 75% of a prodrug discussed in section I above. In one embodiment, the lipid membrane of a nanoparticle comprises about 0.1, 0.2, 0.3, 0.4, 0.5, 0.6, 0.7, 0.8, 0.9, or 1% of a prodrug. In another embodiment, the lipid membrane of a nanoparticle comprises about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, or 75 percent of a prodrug. In some embodiments, the lipid membrane of a nanoparticle comprises about 10% to about 60% of a prodrug. In other embodiments, the lipid membrane of a nanoparticle comprises about 20% to about 50% of a prodrug. In yet another embodiment, the lipid membrane of a nanoparticle comprises about 30% to about 40% of a prodrug.

A nanoparticle lipid membrane may comprise one or more than one type of prodrug. For instance, a nanoparticle lipid membrane may comprise one, two, three, four, five, six, or more than six types of prodrug. In each instance, the total percent of the membrane that comprises prodrug will typically be about 0.1% to about 70%.

Typically, the stable membrane of a nanoparticle of the invention should be compatible with in vivo use. For example, the lipid membrane of a nanoparticle should not substantially initiate the complement pathway or hemolysis.

The composition of a stable membrane can vary so long as a prodrug is substantially not released from the particle until after the fusion of the particle with a target cell membrane, and the prodrug can be transferred from the nanoparticle lipid membrane to a target cell membrane. An amphiphilic membrane may comprise polymers or a combination of lipids and polymers. In one embodiment, the stable membrane comprises amphiphilic material. The phrase "amphiphilic material," as used herein, refers to a material that has both a hydrophobic and a hydrophilic portion, such as lipid material or amphiphilic polymers. The amphiphilic material may be natural, synthetic, or semisynthetic. As used herein, "natural" refers to a material that may be found in nature, "synthetic" refers to a material that may be created in a laboratory setting, and "semisynthetic" refers to a natural material that has been altered in a laboratory setting. In one embodiment, the amphiphilic material is lipid material. For instance, the outer layer may be a single lipid layer or may include a multi-lamellar lipid layer. Lipid material is used herein in its broadest sense, including but not limited to a derivatized, natural, or synthetic phospholipid, a fatty acid, cholesterol, lysolipid, lipid, sphingomyelin, tocopherol, glucolipid, sterylamine, cardiolipin, plasmalogen, lipid with ether or ester linked fatty acids, a polymerized lipid, lipoprotein, glycolipids, derivatized surfactants, drug functionalized lipids, targeted ligand functionalized lipids, contrast agents conjugated lipids, lipid polymers, surfactants, or a combination thereof.

The amphiphilic membrane may also include lipid-conjugated polyethylene glycol (PEG). Generally speaking, however, the membrane does not comprise more than 10% PEG. In some embodiments, the membrane comprises less than 10, 9, 8, 7, 6, 5, 4, 3, 2, or 1% of PEG.

Additionally, the stable membrane may comprise a surfactant. In some embodiments, preferred surfactants are phospholipids and cholesterol. Moreover, surfactants may include but are not limited to, 1,2-dipalmitoyl-sn glycerol-3-phosphoethanolamine-N-4-(p-maleimidophenyl)butyramide, amine-$PEG_{2000}$-phosphatidylethanolamine, phosphatidylethanolamine, acacia, cholesterol, diethanolamine, glyceryl monostearate, lanolin alcohols, lecithin, including egg-yolk lecithin, mono- and di-glycerides, mono-ethanolamine, oleic acid, oleyl alcohol, poloxamer, peanut oil, palmitic acid, polyoxyethylene 50 stearate, polyoxyl 35 castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan mono-laurate, sorbitan monooleate, sorbitan mono-palmitate, sorbitan monostearate, stearic acid, trolamine, and emulsifying wax. The above surfactants may be used alone or in combination to assist in stabilizing the nanoparticles.

In one embodiment, the amphiphilic membrane of the particle may comprise polysorbate. For instance, the membrane may comprise between about 1 and about 50% polysorbate. In certain embodiments, the membrane may comprise about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50% polysorbate.

Moreover, suspending and/or viscosity-increasing agents that may be used include, but are not limited to, acacia, agar, alginic acid, aluminum mono-stearate, bentonite, magma, carbomer 934P, carboxymethylcellulose, calcium and sodium and sodium 12, carrageenan, cellulose, dextrin, gelatin, guar gum, hydroxyethyl cellulose, hydroxypropyl methylcellulose, magnesium aluminum silicate, methylcellulose, pectin, polyethylene oxide, polyvinyl alcohol, povidone, propylene glycol alginate, silicon dioxide, sodium alginate, tragacanth, and xanthum gum.

In various embodiments, the amphiphilic material of the lipid membrane may be cross-linked to stabilize the nanoparticle. Such cross-linking, however, should still allow adequate lipid mobility to facilitate transfer of a prodrug from a nanoparticle to a target cell membrane. In some embodiments, the particles may be cross-linked on the surface of the outer layer. In other embodiments, the particles may be cross-linked within the outer layer. The cross-linking may be chemical cross-linking or photochemical cross-linking. Briefly, suitable cross-linkers will react with one or more active groups of the outer layer. Cross-linkers may be homobifunctional or heterobifunctional. Suitable chemical cross-linkers may include glutaraldehyde, bis-carboxylic acid spacers, or bis-carboxylic acid-active esters. Additionally, the outer layer may be chemically cross-linked using a bis-linker amine/acid by carbodiimide coupling protocol. Alternatively, the particle may be cross-linked using a click chemistry protocol. In still other embodiments, carbodiimde-coupling chemistry, acylation, active ester coupling, or alkylation may be used to cross-link the outer layer. In an exemplary embodiment, the cross-linking is carbodiimide mediated. In some embodiments, EDC (also EDAC or EDCI, 1-ethyl-3-(3-dimethylaminopropyl) carbodiimide hydrochloride), a highly water soluble carbodiimide, is employed in the 4.0-6.0 pH range to activate carboxyl groups for the coupling of primary amines to yield amide bonds. To enhance the coupling efficiencies, EDC may be used in combination with N-hydroxysuccinimide (NHS) or sulfo-NHS. One of ordinary skill in the art would recognize that a suitable cross-linker can and will vary depending on the composition of the particle and the intended use.

(b) Fusion

A nanoparticle of the invention may fuse with a target cell membrane. As used herein, "fuse" refers to an aligning of the lipid membrane of a nanoparticle with the lipid membrane of a target cell, such that interaction between the two membranes may occur. In an exemplary embodiment, "fuse" refers to hemifusion of the particle membrane with the outer leaflet of the target cell membrane. (Lanza, et al. Circulation 2002; 106:2842; Partlow et al. Biomaterials 2008; 29: 3367; Soman, et al. Nano Letters 2008; 8:1131-1136) In one embodiment, a nanoparticle of the invention comprises a lipid membrane that is stable, in vivo, for at least the time required for the nanoparticle to fuse with a target cell membrane and transfer the prodrug to the target cell membrane. Stated another way, a nanoparticle of the invention substantially retains the prodrug within the lipid membrane of the nanoparticle unless and until the nanoparticle fuses with a target cell membrane and transfers the prodrug from the nanoparticle to the target cell membrane. In another embodiment, a nanoparticle of the invention comprises a lipid membrane that is stable, in vivo, for at least the time required for the nanoparticle to fuse with a target cell membrane to enable endocytosis of the nanoparticle.

The length of time required for a nanoparticle to fuse with a target cell membrane can and will vary depending on the nanoparticle (e.g. whether it comprises a homing ligand), the size of the nanoparticle, the location of the intended target cell, and the prodrug utilized, among other factors. One of skill in the art would be able to perform assays known in the art to determine the ideal length of time required for a particle nanoparticle/prodrug/target cell combination.

In some embodiments, the length of time is 1, 2, 3, 4, 5, 6, 7, 8, 9, 10, 11, 12, 13, 14, 15, 16, 17, 18, 19, or 20 minutes. In other embodiments, the length of time is 20, 21, 22, 23, 24, 25, 26, 27, 28, 29, 30, or more than 30 minutes. For instance, the length of time may be about 30, 35, 40, 45, 50, 55, 60, 65, 70, 75, 80, 85, 90, 95, 100, or more than 100 minutes. In an exemplary embodiment, the length of time is approximately 20 minutes.

(c) Transfer of the Prodrug

As briefly mentioned above, a prodrug of the invention may be transferred from the lipid membrane of a nanoparticle to the lipid membrane of a cell. In certain embodiments, to enable transfer of the prodrug, the lipid membrane of the nanoparticle must be mobile. Furthermore, in certain embodiments, the lipids of the nanoparticle lipid membrane must be free to exchange with the target cell lipid membrane. Stated another way, in these embodiments, a nanoparticle lipid membrane should not have substantial surface barriers or energy barriers to lipid exchange with a target cell membrane. This may, for instance, impact the lipid composition of the nanoparticle lipid membrane. Lipid compositions may be tested using methods known in the art to ensure adequate lipid mobility to transfer the prodrug from a nanoparticle to a target cell membrane. In an exemplary embodiment, as shown in the examples, the membrane of the particle forms a hemifusion structure with the outer leaflet of the target cell membrane. Such a fusion event may be visualized, as illustrated in the examples. Hence, one of skill in the art would be able to determine if a particular membrane, formed using the guidelines detailed above, forms a hemifusion structure with a target cell membrane.

The amount of time required for transfer of a prodrug from the membrane of a nanoparticle to the lipid membrane of a target cell can and will vary depending on several factors, including the nanoparticle (e.g. whether it comprises a homing ligand), the size of the nanoparticle, the location of the intended target cell, and the prodrug utilized, among other factors. In some embodiments, the length of time is 1, 2, 3, 4, 5, 6, 7, 8, 9, 10, 11, 12, 13, 14, 15, 16, 17, 18, 19, or 20 minutes. In other embodiments, the length of time is 20, 21, 22, 23, 24, 25, 26, 27, 28, 29, 30, or more than 30 minutes. For instance, the length of time may be about 30, 35, 40, 45, 50, 55, 60, 65, 70, 75, 80, 85, 90, 95, 100, or more than 100 minutes.

(d) Homing Ligand

In some embodiments, a nanoparticle of the invention may comprise a homing ligand. As used herein, "homing ligand" refers to a biomolecule that aids the fusion of the nanoparticle with the target cell membrane.

Homing ligands may include, but are not limited to, antibodies, antibody fragments, proteins, peptides, carbohydrates, lipids, small molecules, polysaccharides, nucleic acids, aptamers, peptidomimetics, other mimetics and drugs alone or in combination. Additionally, homing ligands may include microbes, such as phage or viruses. A homing ligand may also be an engineered analogue or derivative of each of the above. Homing ligands may be may be attached directly or indirectly to the nanoparticle.

Direct conjugation of a homing ligand to a nanoparticle refers to the preparation of a homing ligand-particle complex wherein the homing ligand is either adsorbed through ionic, electrostatic, hydrophobic or other noncovalent means to the nanoparticle surface (e.g. acylated-antibody, or hybridization between complementary nucleic acid sequences), or chemically linked to the surface through covalent bonds to a component of the lipid surface, or intrinsically incorporated into the lipid membrane as a component of the membrane (e.g. a lipid derivatized to a peptidomimetic agent).

Indirect conjugation refers to forming the complex between the nanoparticle and the homing ligand in vivo in two or more steps. Indirect conjugation utilizes a chemical linking system to produce the close and specific fusion of the particle to a targeted cell or tissue surface. A non-limiting example of an indirect homing system is avidin-biotin.

Avidin-biotin interactions are useful noncovalent homing systems that have been incorporated into many biological and analytical systems and selected in vivo applications. Avidin has a high affinity for biotin ($10^{-15}$ M) facilitating rapid and stable binding under physiological conditions. Homing systems utilizing this approach are administered in two or three steps, depending on the formulation. Typically, a biotinylated ligand, such as a monoclonal antibody, is administered first and is "pre-homed" to a unique molecular epitope. Next, avidin is administered, which binds to the biotin moiety of the "pre-homed" ligand. Finally, the biotinylated particle is added and binds to the unoccupied biotin-binding sites remaining on the avidin thereby completing the biotinylated ligand-avidin-particle "sandwich". The avidin-biotin approach can avoid accelerated, premature clearance of homed particles by the mononuclear phagocyte system (MPS) secondary to the presence of surface antibody. Additionally, avidin, with four independent biotin-binding sites provides signal amplification and improves detection sensitivity.

Homing ligands may be chemically attached to the surface of particles by a variety of methods depending upon the nature of the homing ligand and composition of the particle surface. Direct chemical conjugation of homing ligands to proteinaceous particles often take advantage of numerous amino-groups (e.g. lysine) inherently present within the surface. Alternatively, functionally active chemical groups such as pyridyldithiopropionate, maleimide or aldehyde may be incorporated into the surface as chemical "hooks" for homing ligand conjugation after the particles are formed. Another common post-processing approach is to activate surface carboxylates with carbodiimide prior to homing ligand addition.

The selected covalent linking strategy is primarily determined by the chemical nature of the homing ligand. For instance, monoclonal antibodies and other large proteins may denature under harsh processing conditions whereas the bioactivity of carbohydrates, short peptides, aptamers, drugs or peptidomimetics often can be preserved under these conditions.

To ensure high homing ligand binding integrity and maximize nanoparticle avidity, flexible spacer arms, e.g. polyethylene glycol, amino acids, long or short chain hydrocarbons, sugars (e.g. polydextrose), nucleic acids, aptamers, or simple caproate bridges, can be inserted between an activated surface functional group and the homing ligand. These extensions may be 2 nm or longer.

The homing ligand may be immobilized within the lipid material by using a "primer material". A "primer material" is any surfactant compatible compound incorporated in the particle to chemically couple with or adsorb a specific binding or homing ligand i.e. any constituent or derivatized constituent incorporated into the lipid membrane that could be chemically utilized to form a covalent bond between the particle and homing ligand or a component of the homing ligand (if it has subunits). The homing ligand may be covalently bonded to "primer material" with coupling agents using methods that are known in the art. One type of coupling agent may use a carbodiimide such as 1-ethyl-3-(3-N,N dimethylaminopropyl)carbodiimide hydrochloride or 1-cyclohexyl-3-(2-morpholinoethyl)carbodiimide methyl-p-toluenesulfonate. The primer material may be amine-PEG$_{2000}$-phosphatidylethanolamine, phosphatidylethanolamine, N-caproylamine phosphatidylethanolamine, N-dodecanylamine phosphatidylethanolamine, phosphotidylthioethanol, 1,2-diacyl-sn-glycerol-3-phosphoethanolamine-N-[4-p-maleimidephenyl)-butyl] amide, N-succinyl-phosphatidylethanolamine, N-glutaryl-phosphatidylethanolamine, N-dodecanyl-phosphatidylethanolamine, N-biotinyl-phosphatidylethanolamine, N-biotinylcaproyl-phosphatidylethanolamine, and phosphatidylethylene glycol. Other suitable coupling agents may include aldehyde coupling agents having either ethylenic unsaturation such as acrolein, methacrolein, or 2-butenal, or having a plurality of aldehyde groups such as glutaraldehyde, propanedial or butanedial. Other coupling agents may include 2-iminothiolane hydrochloride and bifunctional N-hydroxysuccinimide esters such as disuccinimidyl subsrate, disuccinimidyl tartrate, bis[2-(succinimidooxycarbonyloxy)ethyl]sulfone, disuccinimidyl propionate, and ethylene glycolbis(succinimidyl succinate). Non-limiting examples of heterobifunctional reagents may include N-(5-azido-2-nitrobenzoyloxy) succinimide, p-azidophenylbromide, p-azidophenylglyoxal, 4-fluoro-3-nitrophenylazide, N-hydroxysuccinimidyl-4-azidobenzoate, m-maleimidobenzoyl N-hydroxysuccinimide ester, methyl-4-azidophenylglyoxal, 4-fluoro-3-nitrophenyl azide, N-hydroxysuccinimidyl-4-azidobenzoate hydrochloride, p-nitrophenyl 2-diazo-3,3,3-trifluoropropionate, N-succinimidyl-6-(4'-azido-2'-nitrophenylamino) hexanoate, succinimidyl 4-(N-maleimidomethyl)cyclohexane-1-carboxylate, succinimidyl 4-(p-maleimidophenyl) butyrate, N-succinimidyl(4-azidophenyldithio)propionate, N-succinimidyl 3-(2-pyridyldithio)propionate, and N-(4-azidophenylthio)phthalamide. Non-limiting examples of homobifunctional reagents may include 1,5-difluoro-2,4-dinitrobenzene, 4,4'-difluoro-3,3'-dinitrodiphenylsulfone, 4,4'-diisothiocyano-2,2'-disulfonic acid stilbene, p-phenylenediisothiocyanate, carbonylbis(L-methionine p-nitrophenyl ester), 4,4'-dithiobisphenylazide, erythritolbiscarbonate and bifunctional imidoesters such as dimethyl adipimidate hydrochloride, dimethyl suberimidate, dimethyl 3,3'-dithiobispropionimidate hydrochloride and the like. Covalent bonding of a specific binding species to the "primer material" can be carried out with the above reagents by conventional, well-known reactions, for example, in the aqueous solutions at a neutral pH and at temperatures of less than 25° C. for 1 hour to overnight.

A particle membrane may generally comprise between 0% and about 3% of a homing ligand. For instance, in one embodiment, a membrane may comprise up to 1% of a homing ligand, up to 2% of a homing ligand, or up to 3% of a homing ligand.

(e) Passive Homing

As an alternative to a nanoparticle of the invention comprising a homing ligand, a nanoparticle may use "passive homing." As used herein, "passive homing" refers to the natural tendency of nanoparticles to accumulate in, and therefore fuse with, target cell membranes of certain tissues. For instance, passive homing may refer to charge interactions between a lipid membrane of a nanoparticle and the lipid membrane of a target cell. Or, in other embodiments, passive homing may refer to the enhanced permeability effect found in tumor tissue.

(f) Nanoparticle Core

The core of a nanoparticle of the invention can and will vary without impacting the necessary features of the lipid membrane. Generally speaking, however, the core should allow adequate lipid transfer between the nanoparticle and the target cell membrane.

(g) Imaging/Tracking Agents

A nanoparticle of the invention may also include other imaging/tracking agents. For instance, a nanoparticle may include imaging/tracking agents that may be used for microscopy, e.g. fluorescent microscopy, confocal microscopy, or electron microscopy, magnetic resonance imaging, tomography, gamma (SPECT/CT, planar) and positron emission tomography (PET/CT), radiography, computed tomography (CT), spectral CT, photoacoustic tomography (PAT) or ultrasound. Imaging/tracking agents may be detectable in situ, in vivo, ex vivo, and in vitro. Microscopy imaging/tracking agents are well known in the art, and may include fluorescent molecules such as FITC, rhodamine, and Alexafluor cyan dyes. Similarly, magnetic resonance imaging molecules, such as paramagnetic and superparamagnetic agents, radiography imaging molecules, near infrared (NIR) optical agents and ultrasound molecules are well known in the art, and an appropriate imaging molecule may be selected by one of skill in the art after consideration of the composition of the particle and the intended use of the particle. In certain embodiments, the outer layer may also comprise chelators for radiometals to be detected by nuclear imaging methods, such as PET, SPECT, and related methodologies.

(h) Pharmaceutical Composition

The present invention further comprises a pharmaceutical composition comprising a nanoparticle, or a plurality of nanoparticles, of the invention. A pharmaceutical composition may be a solution, a mixture, or a suspension of nanoparticles. In one embodiment, the pharmaceutical composition may be a solution. In another embodiment, the pharmaceutical composition may be a mixture. In another embodiment, the pharmaceutical composition may be a suspension. A non-limiting example of a suspension is a colloid.

In some embodiments, the pharmaceutical composition may be a colloid. Generally speaking a colloid is a suspension of fine particles that do not readily settle out of the suspension. A colloid may be formed by microfluidization.

A pharmaceutical composition of the particles of the invention may be administered to a subject to enable imaging and/or treatment of biological tissue. Suitable subjects may include, but are not limited to, mammals, amphibians, reptiles, birds, fish, and insects. Non-limiting examples of mammals include humans, non-human primates, and rodents.

The pharmaceutical composition may be formulated and administered to a subject by several different means that will deliver an effective dose for treatment and/or imaging. Such compositions may generally be administered parenteraly, intraperitoneally, intravascularly, or intrapulmonarily in dosage unit formulations containing conventional nontoxic pharmaceutically acceptable carriers, adjuvants, excipients, and vehicles as desired. The term parenteral as used herein includes topical, subcutaneous, intravenous, intramuscular, intraperitoneal, intracystic, intrauterine, intraauricular, intranasal, ocular, intraocular, intrapulmonary, oral, intrapharyngeal, transrectal, intra or transurethral, intrauterine, intravaginal, or intrasternal injection or infusion. Additionally, the term parenteral includes spraying or aerosol administration techniques. In one embodiment, the composition may be administered in a bolus. In a preferred embodiment, the composition may be administered intravenously. Formulation of pharmaceutical compositions is discussed in, for example, Hoover, John E., Remington's Pharmaceutical Sciences, Mack Publishing Co., Easton, Pa. (1975), and Liberman, H. A. and Lachman, L., Eds., Pharmaceutical Dosage Forms, Marcel Decker, New York, N.Y. (1980).

Injectable preparations, for example, sterile injectable aqueous or oleaginous suspensions, may be formulated according to the known art using suitable dispersing or wetting agents and suspending agents. The sterile injectable preparation may also be a sterile injectable solution or suspension in a nontoxic parenterally acceptable diluent or solvent. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed, including synthetic mono- or diglycerides. In addition, fatty acids such as oleic acid are useful in the preparation of injectables. Dimethyl acetamide, surfactants including ionic and non-ionic detergents, and polyethylene glycols can be used. Mixtures of solvents and wetting agents such as those discussed above are also useful. For imaging purposes, formulations for parenteral administration may be in the form of biocompatible solutions or suspensions. Other adjuvants and modes of administration are well and widely known in the pharmaceutical art.

One of skill in the art will recognize that the amount and concentration of a pharmaceutical composition administered to a subject for treatment and/or imaging will depend in part on the subject and the tissue to be treated and/or imaged. Methods for determining optimal amounts are known in the art, and more details may be found in the Examples.

A pharmaceutical composition of the invention may further comprise an additional pharmaceutically active compound known in the art.

III. Methods

Another aspect of the present invention encompasses methods of use for a prodrug or nanoparticle of the invention. Methods of the invention may generally be used in vitro, in vivo, or ex vivo.

In one embodiment, the present invention provides a method for delivering a compound to a cell. The method comprises administering a prodrug of the invention to the cell. In an exemplary embodiment, the method comprises administering a nanoparticle comprising a prodrug of the invention to the cell. In a further exemplary embodiment, the method comprises administering a targeted nanoparticle comprising a prodrug of the invention to the cell. Generally speaking, a suitable cell is any eukaryotic cell, where the outer leaflet of the cell membrane is capable of forming a hemifusion structure with the membrane of the particle.

In another embodiment, the present invention provides a method for increasing the half-life of a compound in the blood of a subject. The method comprises administering a prodrug of the invention to a subject. In an exemplary embodiment, the method comprises administering a nanoparticle comprising a prodrug of the invention. Generally speaking, a suitable subject is a mammal. In one embodiment, a suitable subject may be a rodent. In another embodiment, a suitable subject may be an agricultural animal, e.g. a horse, cow, pig, chicken, etc. In yet another embodiment, a suitable subject is a non-human primate. In still yet another embodiment, a suitable subject is a human.

In yet another embodiment, the present invention provides a method for decreasing the effective dose of a compound in a subject. The method comprises administering a prodrug of the invention to the subject. In an exemplary embodiment, the method comprises administering a nanoparticle comprising a prodrug of the invention to the subject. Suitable subjects are as defined above.

In still another embodiment, the present invention provides a method for controlling the release of a compound in a cell. The method comprises administering a prodrug of the invention to the cell. In an exemplary embodiment, the method comprises administering a nanoparticle comprising a prodrug of the invention to the cell. Suitable cells are as defined above.

In a further embodiment, the present invention provides a method for inhibiting angiogenesis in a subject, the method comprising administering a prodrug of the invention to a subject, wherein the prodrug comprises an antiangiogenic compound. In an exemplary embodiment, the method comprises administering a nanoparticle comprising a prodrug comprising an antiangiogenic compound to a subject.

In an exemplary embodiment, the invention encompasses a method of administering a prodrug of formula I, II, III, IV, V, VI, VII, VIII, IX, X, XI, XII, XIII, XIV, XV, XVI, XVII, XVIII, or XIX to a cell. The method comprises administering a nanoparticle comprising a prodrug of formula I, II, III, IV, V, VI, VII, VIII, IX, X, XI, XII, XIII, XIV, XV, XVI, XVII, XVIII, or XIX to the cell.

The following examples are included to demonstrate preferred embodiments of the invention. It should be appreciated by those of skill in the art that the techniques disclosed in the examples that follow represent techniques discovered by the inventors to function well in the practice of the invention. Those of skill in the art should, however, in light of the present disclosure, appreciate that may changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

The following examples illustrate various iterations of the invention.

Example 1. Targeting and Efficacy of Doxorubicin Prodrug

Figure 1B:
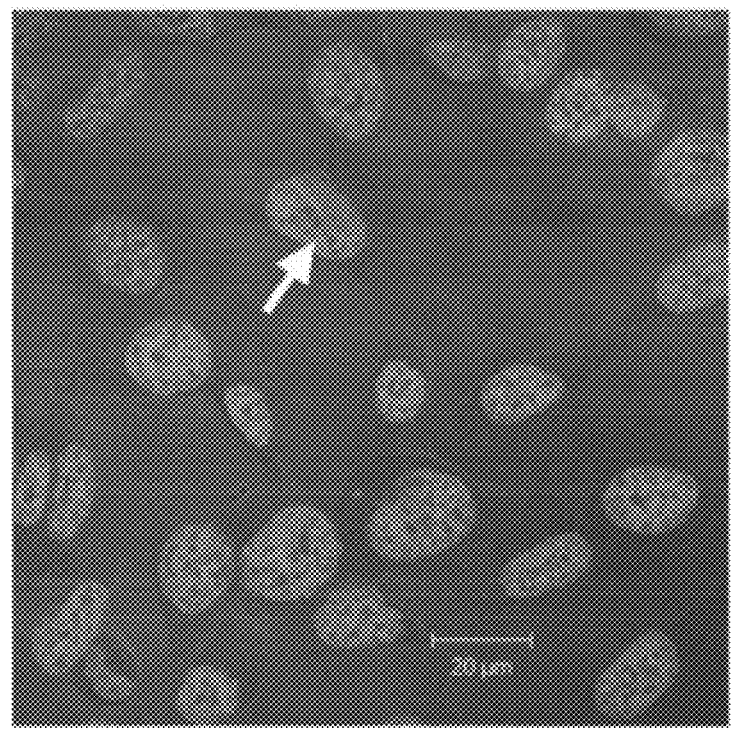
Figure 2:
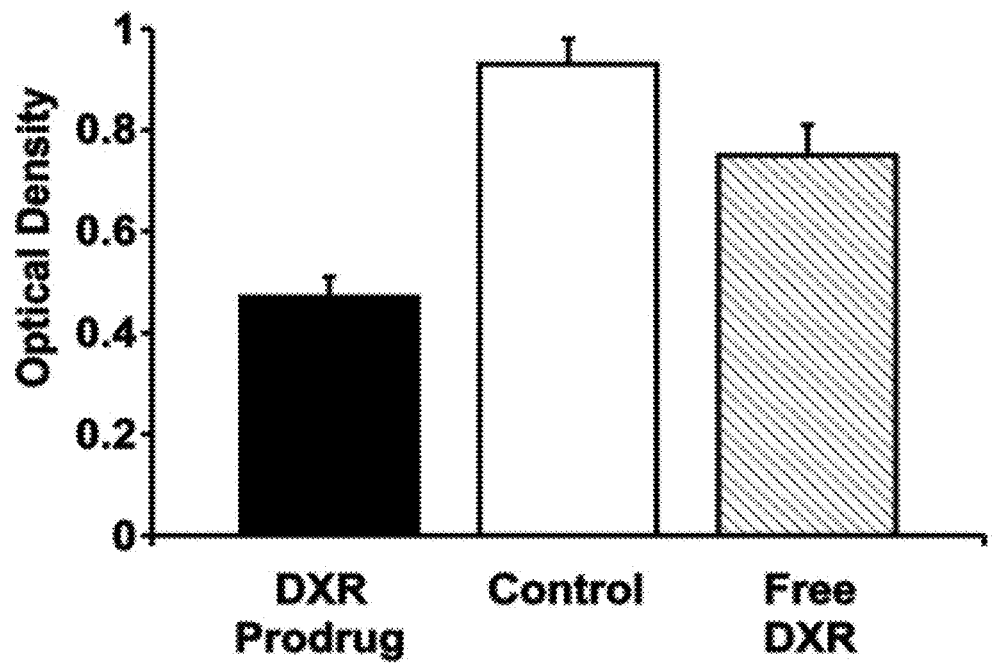
FIG. 2 is a graph depicting the effect of free doxorubicin drug and prodrug doxorubicin on cell proliferation compared to no treatment control.

Two examples of prodrug candidates using paclitaxel or doxorubicin, coupled to a phosphatidylcholine backbone with a 5-carbon sn-2 acyl spacer were synthesized (See Examples below). The structures of the compounds produced were characterized by 1H NMR (400 MHz) spectroscopy. The effect of the $\alpha_v\beta_3$ integrin-targeted doxorubicin prodrug was tested in 2F2B mouse endothelial cells induced to express integrin. Doxorubicin prodrug transfer to the targeted cell and intracellular distribution was confirmed using light microscopy (FIG. 1). Targeted doxorubicin prodrug was distributed in the lipid membrane, throughout the cell membranes and in the nucleus, whereas free doxorubicin drug was only seen in the nucleus. Doxorubicin distribution in the cell membrane acts as a reservoir for doxorubicin transfer to the nucleus for a more effective treatment. The enzymatically released drug also elicited a marked inhibition of endothelial cell proliferation at a level greater than that elicited by free doxorubicin (FIG. 2).

Example 2. In Vivo Activity of Doxorubicin and Paclitaxel Prodrugs

Figure 3:
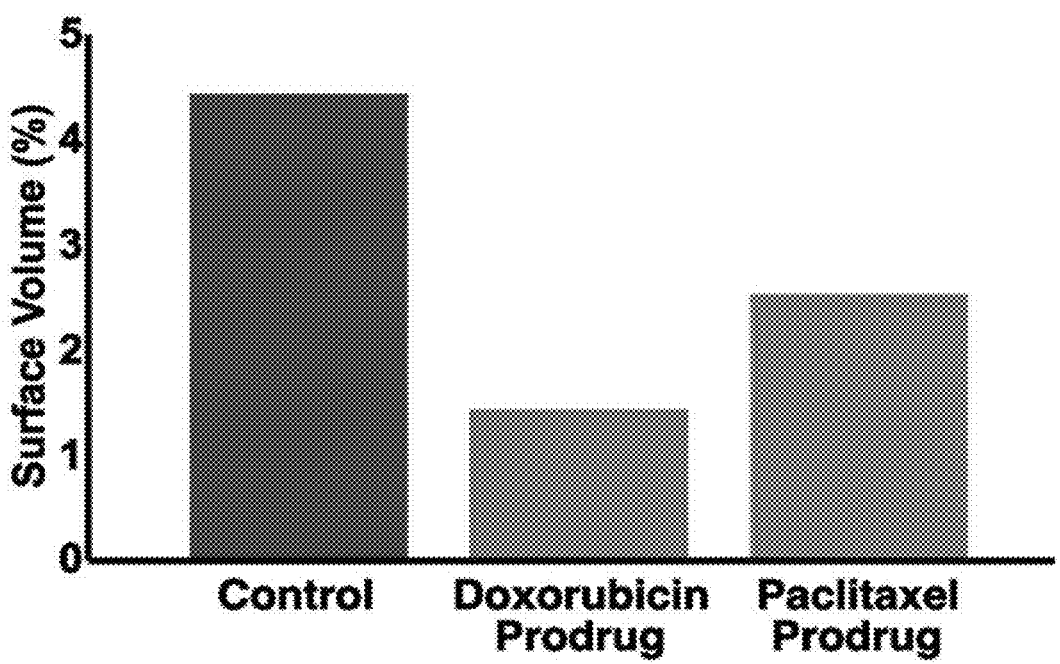
FIG. 3 is a graph depicting the angiogenic response to doxorubicin and paclitaxel prodrugs incorporated into integrin-targeted PFC nanoparticles in the rat matrigel plug model (n=2/group).
Figure 4B:
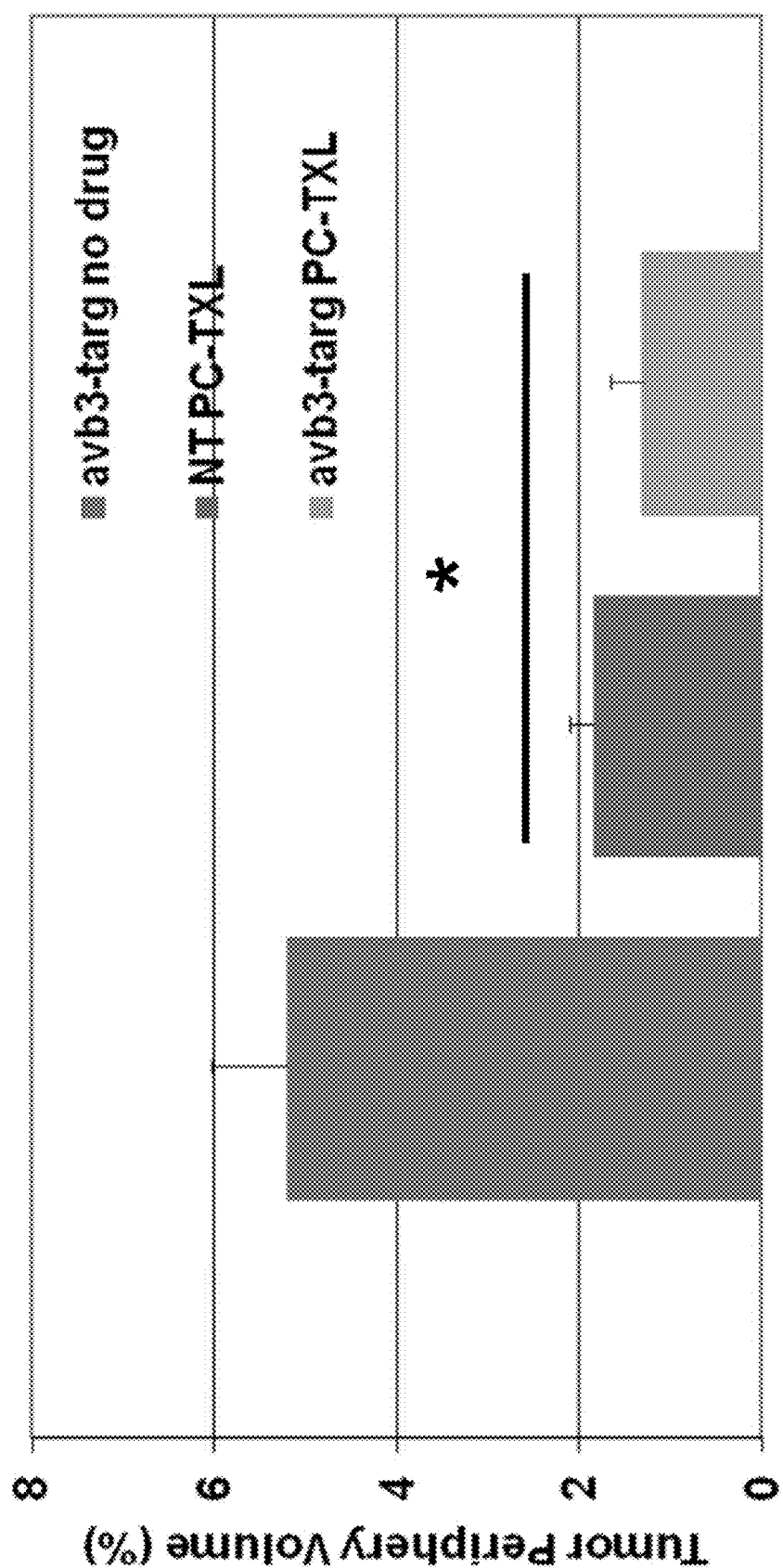

Anti-angiogenesis treatment with integrin-targeted doxorubicin prodrug and paclitaxel prodrug PFC nanoparticles was demonstrated using an in vivo Matrigel plug model in rats. The therapeutic response was assessed using MRI neovascular mapping at 3 T with $\alpha_v\beta_3$ integrin-targeted paramagnetic PFC nanoparticles (FIG. 3). Angiogenesis was decreased by both treatment formulations relative to control. Similar results were obtained in vivo with the Vx2 tumor model in rabbits using paclitaxel prodrug (FIG. 4). Therefore, in contradistinction to prior research that showed loss of paclitaxel or doxorubicin during in vitro dissolution, the phospholipid prodrug forms were retained in circulation, delivered to the target cell, released enzymatically and exerted the intended antiproliferative effects.

Example 3. Synthesis of Sn-2 Doxorubicin Prodrug

Figure 5:
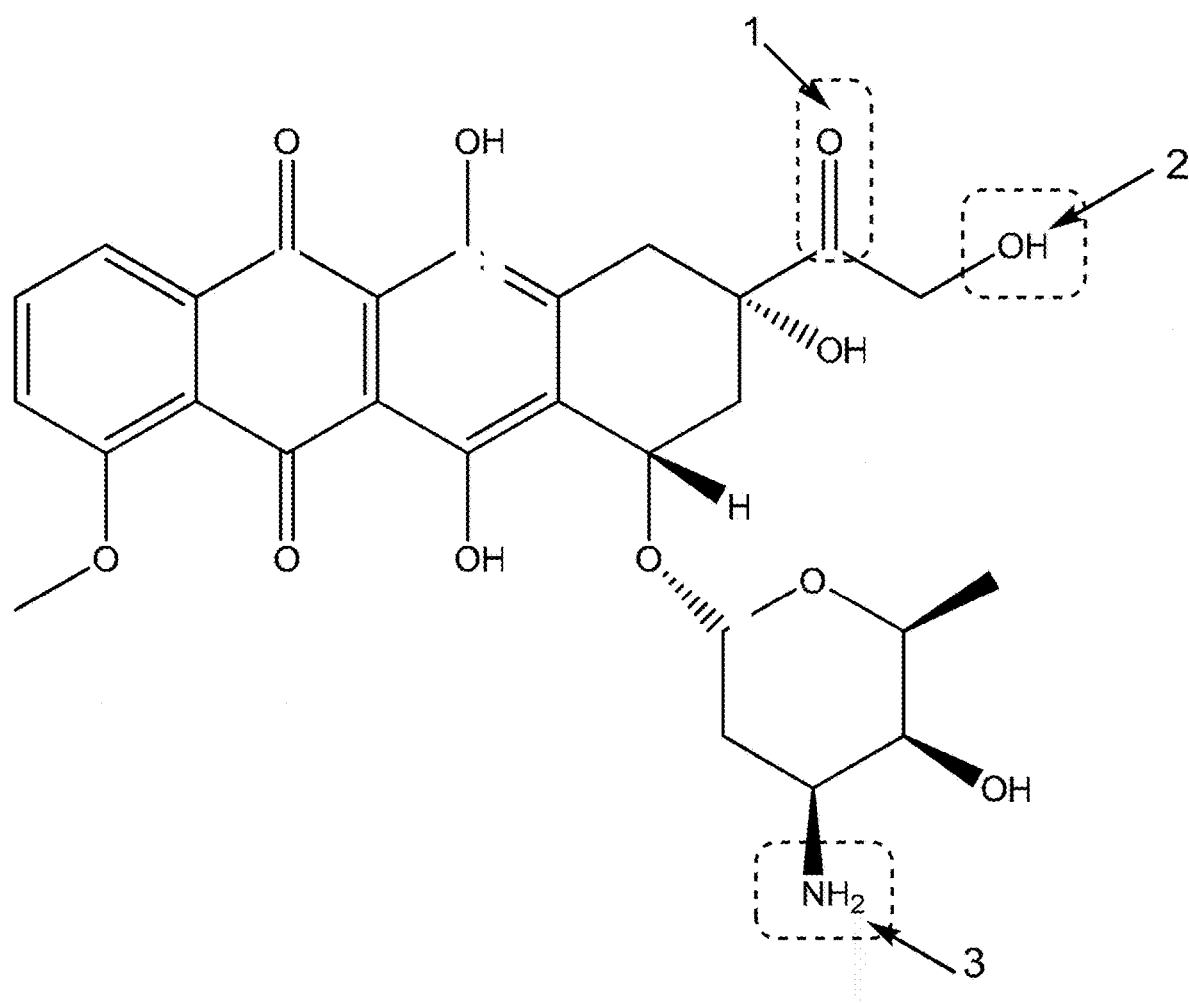
FIG. 5 depicts doxorubicin and available sites for functional modification.
Figure 6:
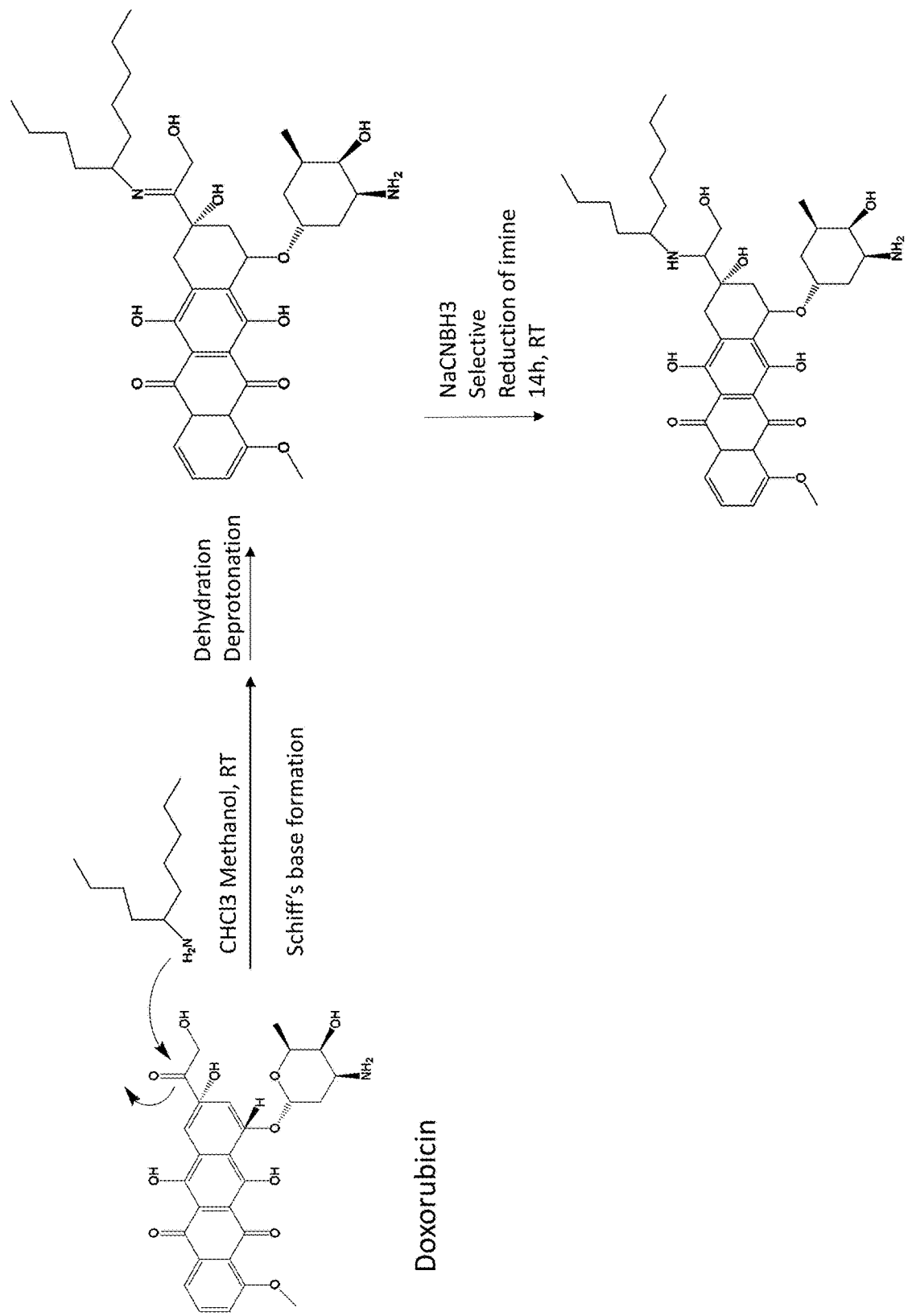
FIG. 6 depicts the synthesis scheme of PC-doxorubicin conjugate 1.

More than three sites are available for functional modification of doxorubicin (FIG. 5): the side chain carbonyl group (site 1), the side chain alcoholic group (site 2) and the amine functionality in the sugar moiety (site 3). In this example, site-3 was used for the modifications described below.

Figure 7:
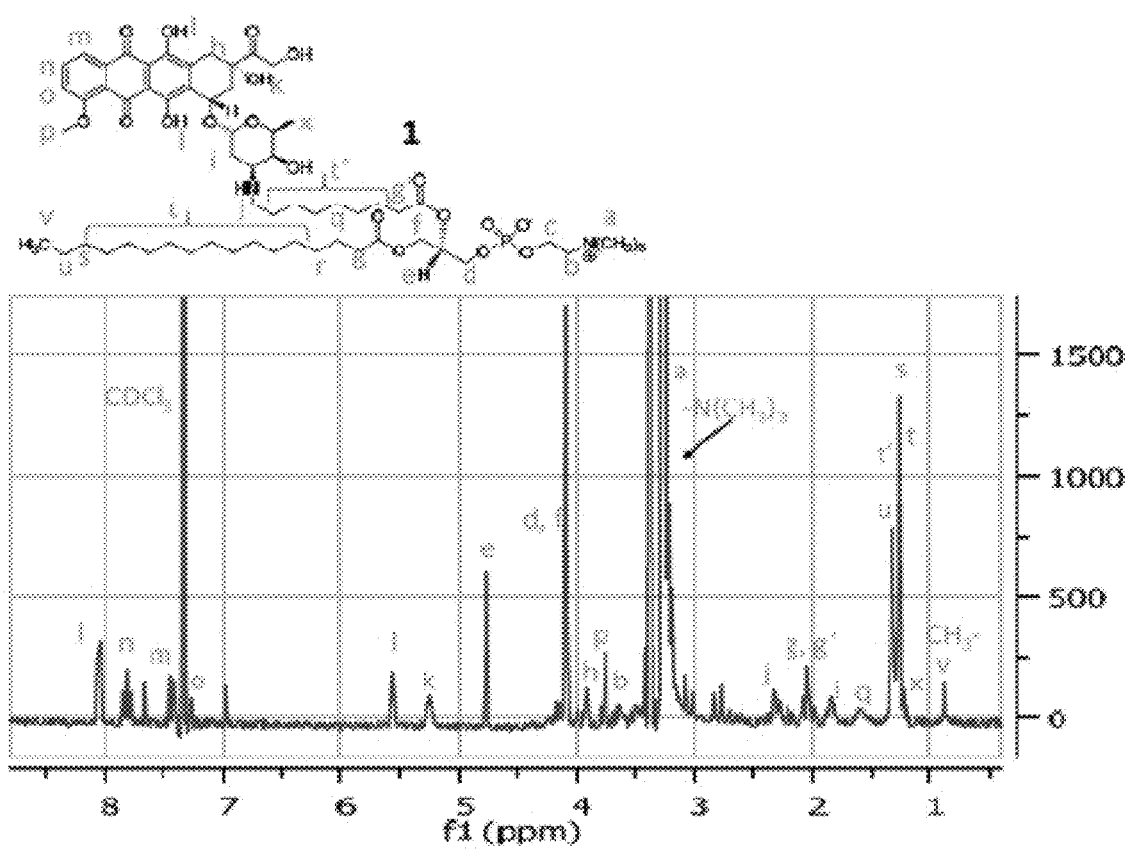
FIG. 7 depicts the PC-doxorubicin (PC-DXR) candidate-1 prodrug, and the 1H NMR (400 MHZ) spectroscopy of that prodrug.

PC-doxorubicin (PC-DXR) conjugate 1 was synthesized by reacting doxorubicin with 16:0-09:0 ALDO(PC) (1-palmitoyl-2-(9'-oxo-nonanoyl)-sn-glycero-3-phosphocholine) in methanol (anhydrous) in the presence of TFA. The subsequent formation of imine was reduced by sodium cyanoborohydride to produce the final product. The structure of the compound was characterized by 1H NMR (400 MHz) spectroscopy (FIG. 7). The conceptual proof of this prodrug approach was demonstrated microscopically by the intracellular distribution doxorubicin, and the marked inhibition of endothelial cell proliferation produced by the enzymatically released drug described in Example 1 above.

Example 4. Synthesis of the Paclitaxel Prodrug

Figure 8:
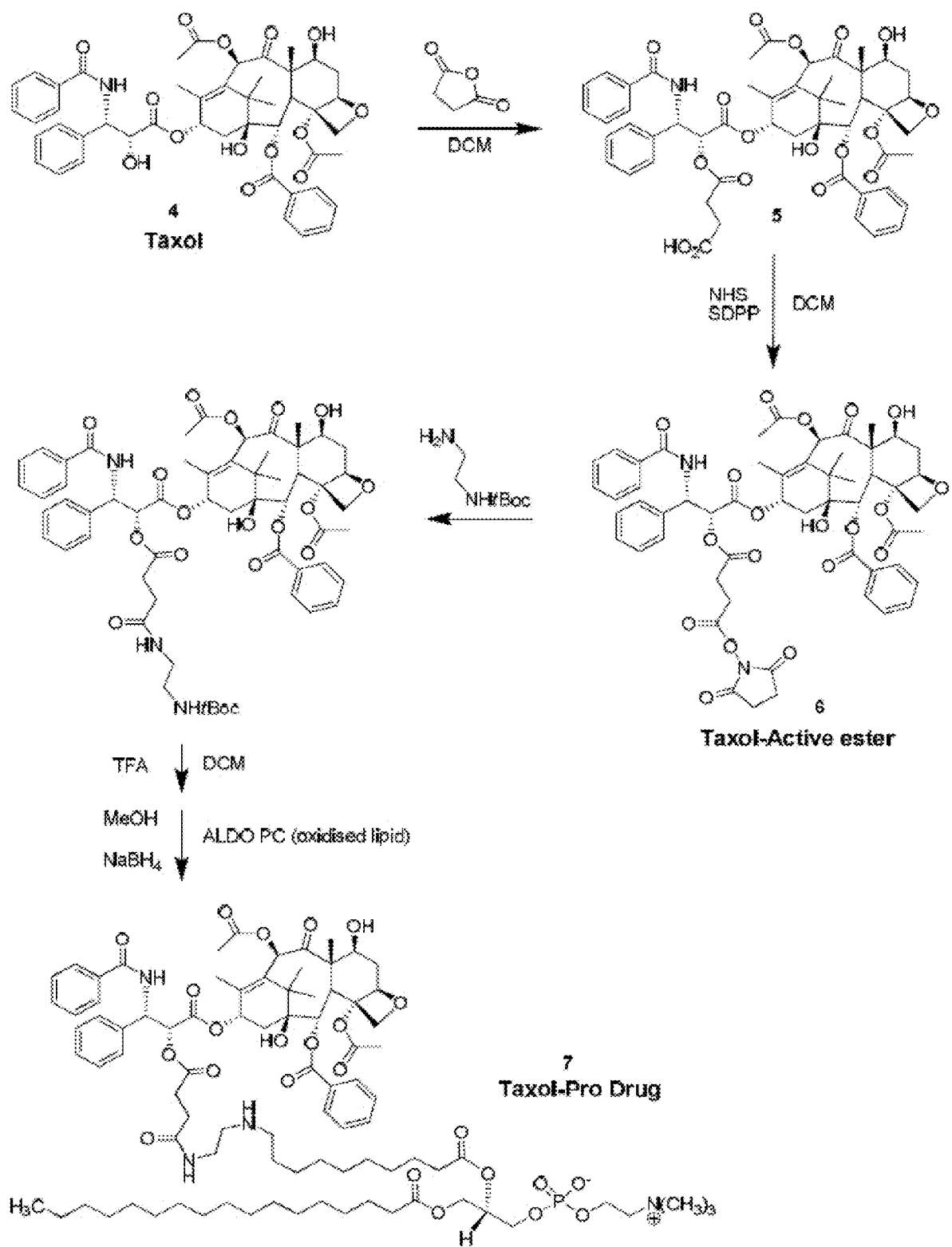
FIG. 8 depicts the synthesis scheme of taxol prodrugs.

Paclitaxel prodrug was synthesized following a five-step synthesis process and purified by column chromatography (FIG. 8). Briefly, commercially available paclitaxel (Avachem Scientific, Inc.) was treated with succinic anhydride in the presence of pyridine to give 2'-succinyl paclitaxel. NHS ester (6) of this intermediate may be obtained by reaction with N-succinimidyl diphenylphosphate (SDPP). The ester was treated with an excess of mono-Boc-ethylene diamine at low temperature followed by deprotection of the tert-Boc. A flexible, linear diamine (1,3-diamino propane) was chosen to reduce the steric hindrance. Finally, the paclitaxel amine was subjected to reductive amination with ALDO PC (or PE) to produce paclitaxel prodrugs (7).

Example 5. Testing of Sn-2 Paclitaxel Prodrug

Figure 9:
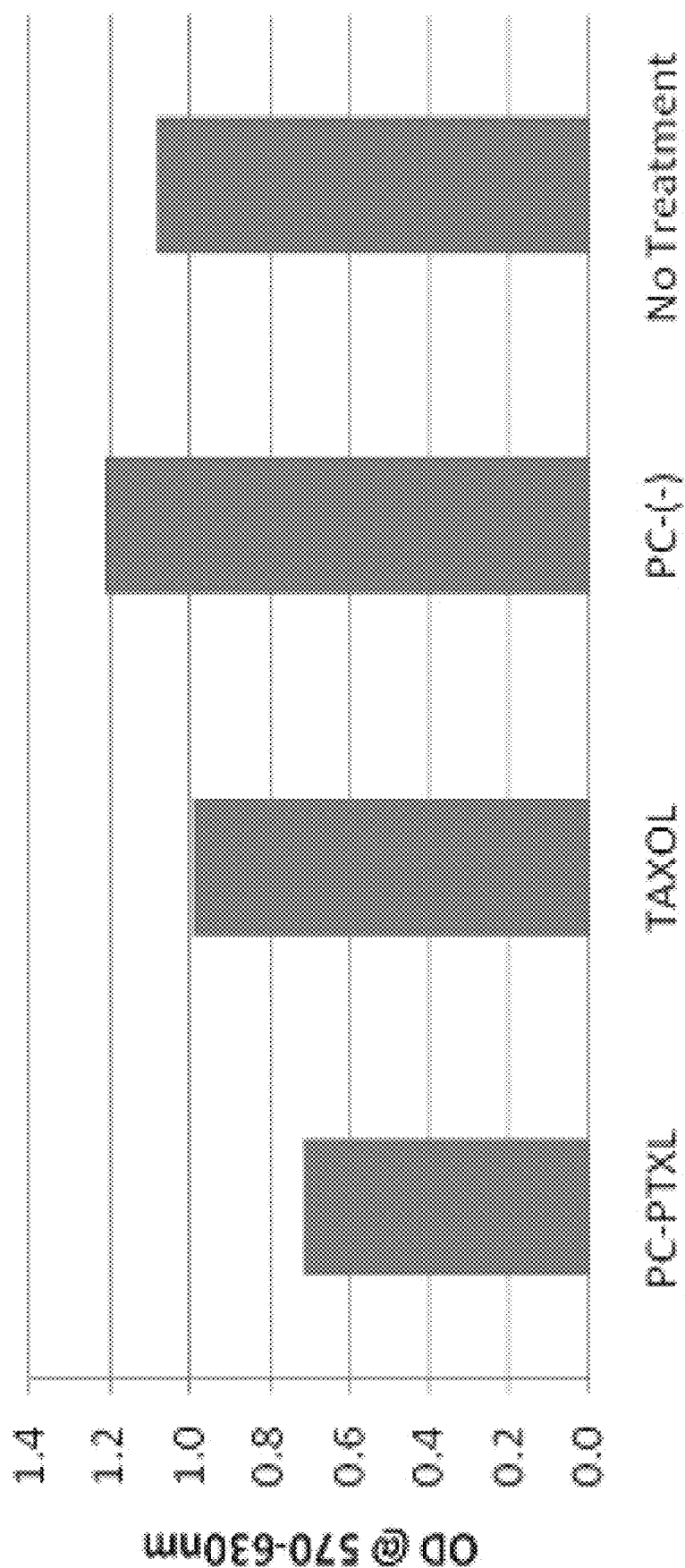
FIG. 9 is a graph depicting the antiproliferative effect of PC-paclitaxel (PC-PXTL) prodrug on 2F2B endothelial cells.

2F2B mouse endothelial cells (ATCC, Manassas, Va., USA) were incubated for 2 days in media, upregulated with 10 nM nicotine or 10 µM angiotensin II to express $\alpha_v\beta_3$ integrin. The cells may then be exposed to integrin-targeted versus nontargeted paclitaxel-GNB nanoparticle treatments with varying drug loads (0.5 to 5 mole %). The cells were also exposed to equivalent amounts of free drug for 30 minutes as a control. Unbound nanoparticles or unabsorbed drug was washed from wells, and cultures were grown for 6 days, and attached viable cell numbers were counted. The number of cells was significantly decreased when treated with paclitaxel-PC prodrug nanoparticles (PC-PTXL), versus equivalent amounts of free Taxol, $\alpha_v\beta_3$ integrin-targeted nanoparticles alone, or saline (FIG. 9).

Example 6. Synthesis of Cis-Platinum Prodrugs

Figure 10:
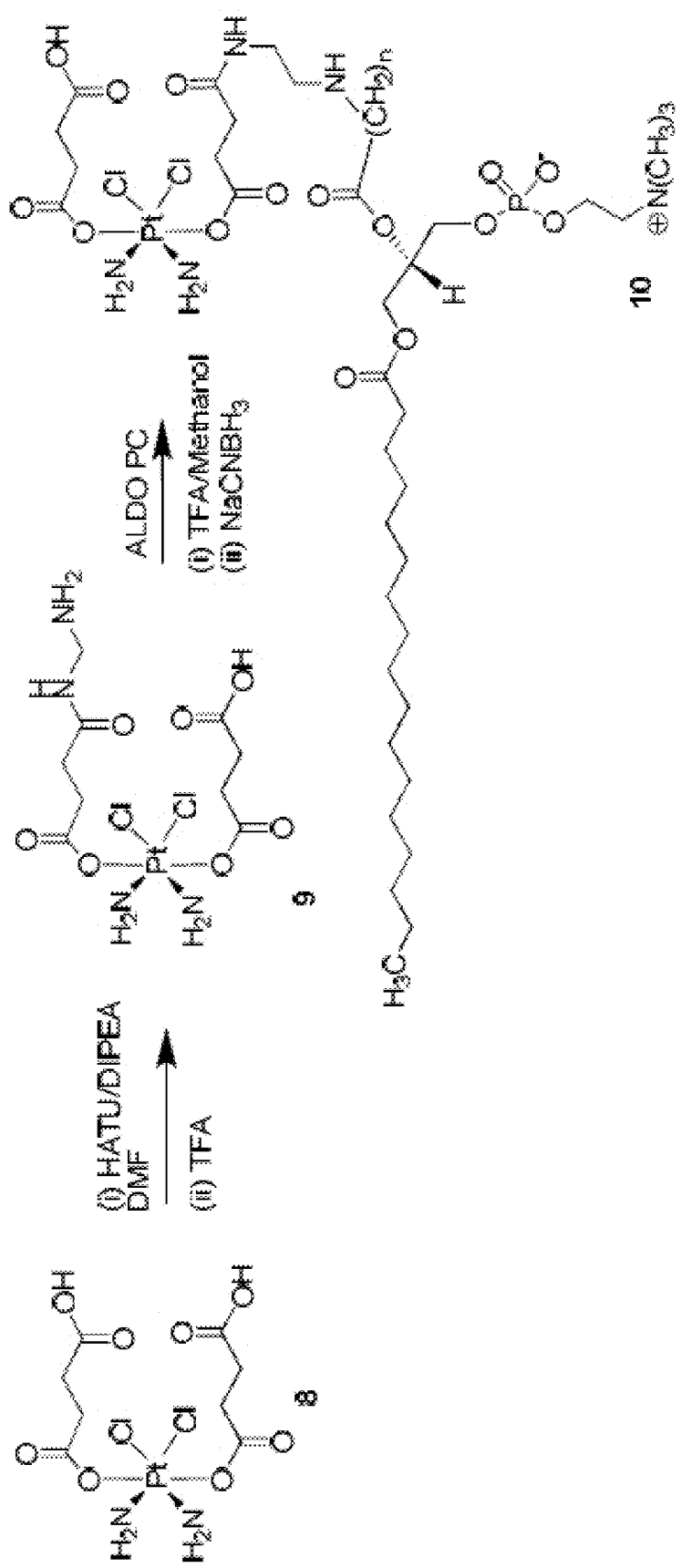
FIG. 10 depicts the synthesis scheme of cis-platin prodrugs-1.

For the synthesis of platinum based anti cancer prodrugs, two approaches may be followed. The first approach (FIG. 10) may involve the preparation of an amine terminated cis platin (9) followed by conjugation with oxidized lipids. The coupling intermediate produced from the amidation reaction of compound 8 with mono Boc-ethylenediamine in presence of HATU/DIPEA, may be subjected to deprotection to produce compound 9. Compound 9 may undergo reductive amination with ALDO PC in methanol to generate cis platin prodrug-1 (10).

Figure 11:
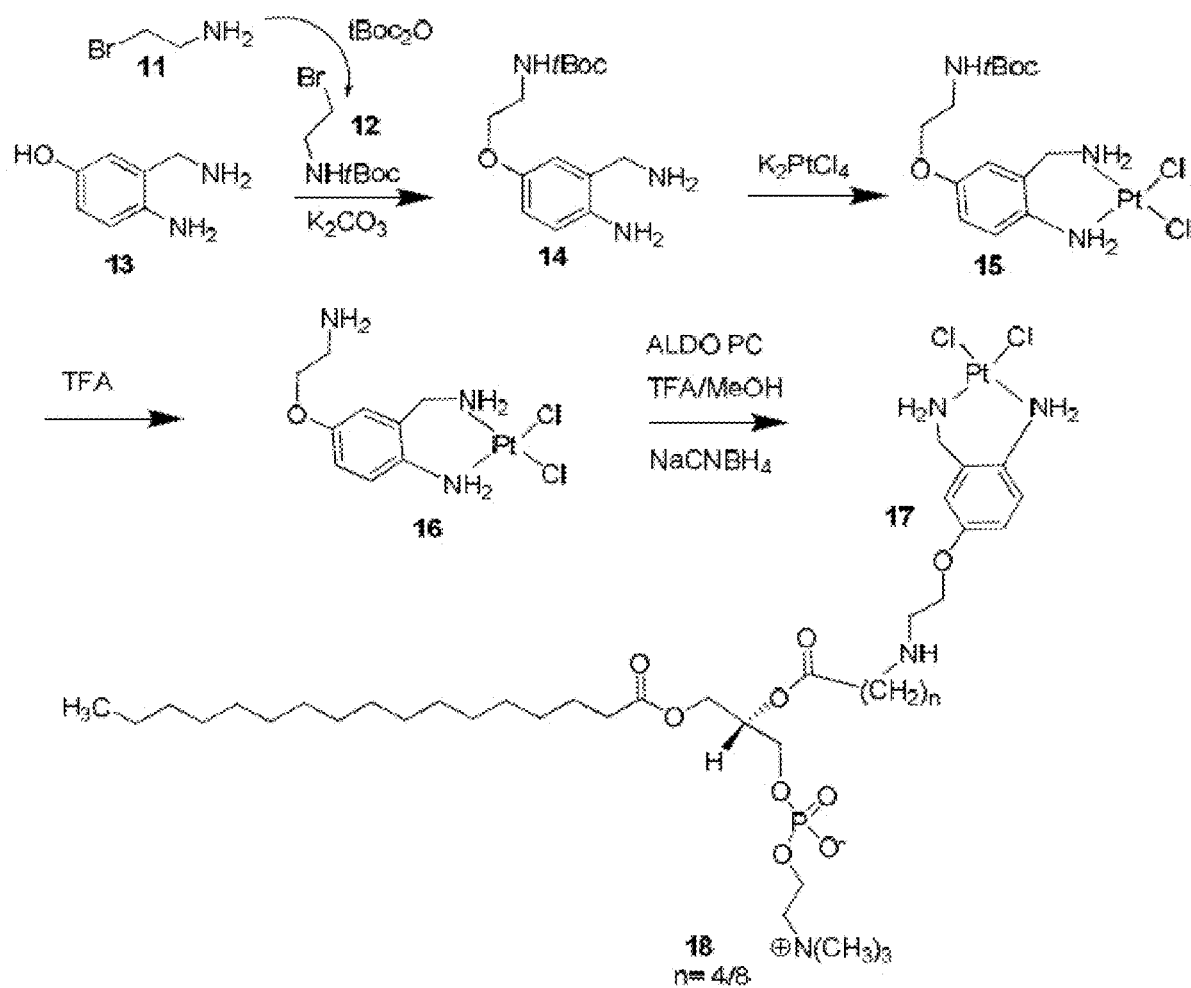
FIG. 11 depicts the synthesis scheme of cis-platin prodrugs-2.

A second approach (FIG. 11) may involve the synthesis of an analogue bearing hydrophobically modified chelating diamines. Cis-platin intermediate 16 may be obtained in three steps from compound 13. Intermediate 16 may be subjected to complexation with $K_2PtCl_4$ by maintaining the pH of the resulting solution at pH 6-7. Finally, compound 13 may undergo reductive amination with ALDO (PC) or (PE) to produce cis platin prodrug-2 (18).

Example 7. Synthesis of Methotrexate Prodrugs

Figure 12:
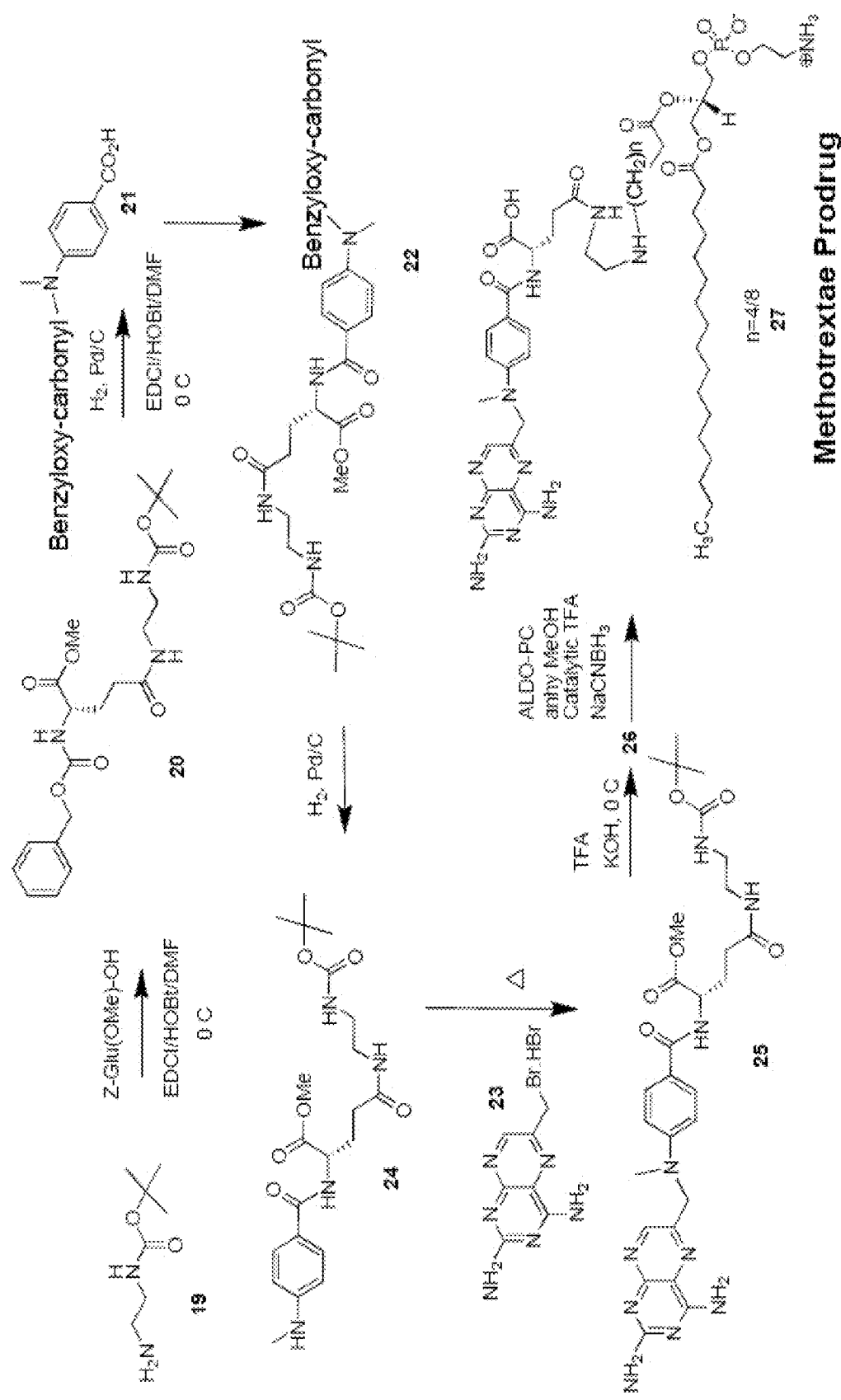
FIG. 12 depicts the synthesis scheme of methotrexate prodrugs.

The synthesis of the methotrexate conjugates is described in (FIG. 12). A short ethylene diamine spacer may be introduced between methotrexate and the oxidized lipid. 6-Bromomethyl-pteridine-2,4-diamine trihydrobromide (BPT.HBr, 23) may be purchased from Ube Industries and coupled with intermediate 24 to produce 25. Compound 25 may be deprotected from tert-Boc followed by ester hydrolysis to produce amine terminated methotrexate (26). Reductive amination of 26 with ALDO (PE) or (PC) may be performed as described earlier to produce methotrexate prodrugs (27).

Example 8. Synthesis of Bortezomib Prodrug

Figure 13:
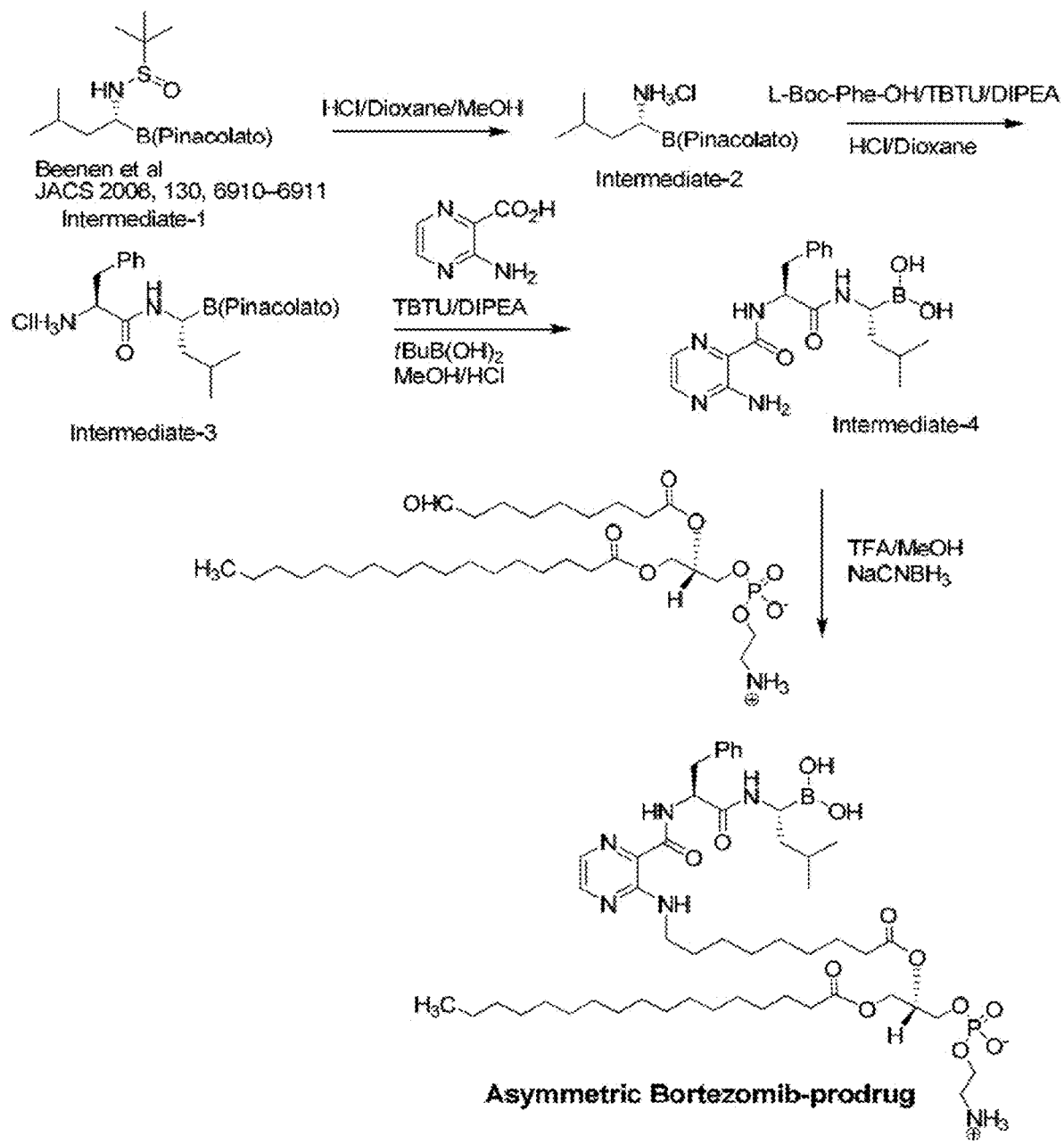
FIG. 13 depicts the synthesis scheme of brotezomib prodrugs.

The asymmetric synthesis of bortezomib-prodrug (FIG. 13) may involve the preparation of intermediate-1 (N-sulfinyl α-amino boron pinacolato complex) by following published methods. Selective removal of the N-sufinyl group under mild acidic conditions may produce the amine hydrochloride (intermediate 2), which may then be coupled with N-Boc-L-phenylalanine by a TBTU/DIPEA mediated reaction protocol. Intermediate-3 (amine hydrochloride) may then undergo coupling with the commercially available 3-aminopyrazine-2-carboxylic acid to produce the pinacol boronate of bortezomib. This may subsequently be hydrolyzed under biphasic conditions utilizing iso-butylboronic acid as a pinacol sequestering agent. Finally the intermediate-4 may undergo a sodium cyanoborohydride mediated reductive amination with ALDO (PC) in presence of catalytic amounts of TFA to produce bortezomib prodrug.

Example 9. Synthesis and of MYC-Inhibitor Prodrugs

Figure 14A:
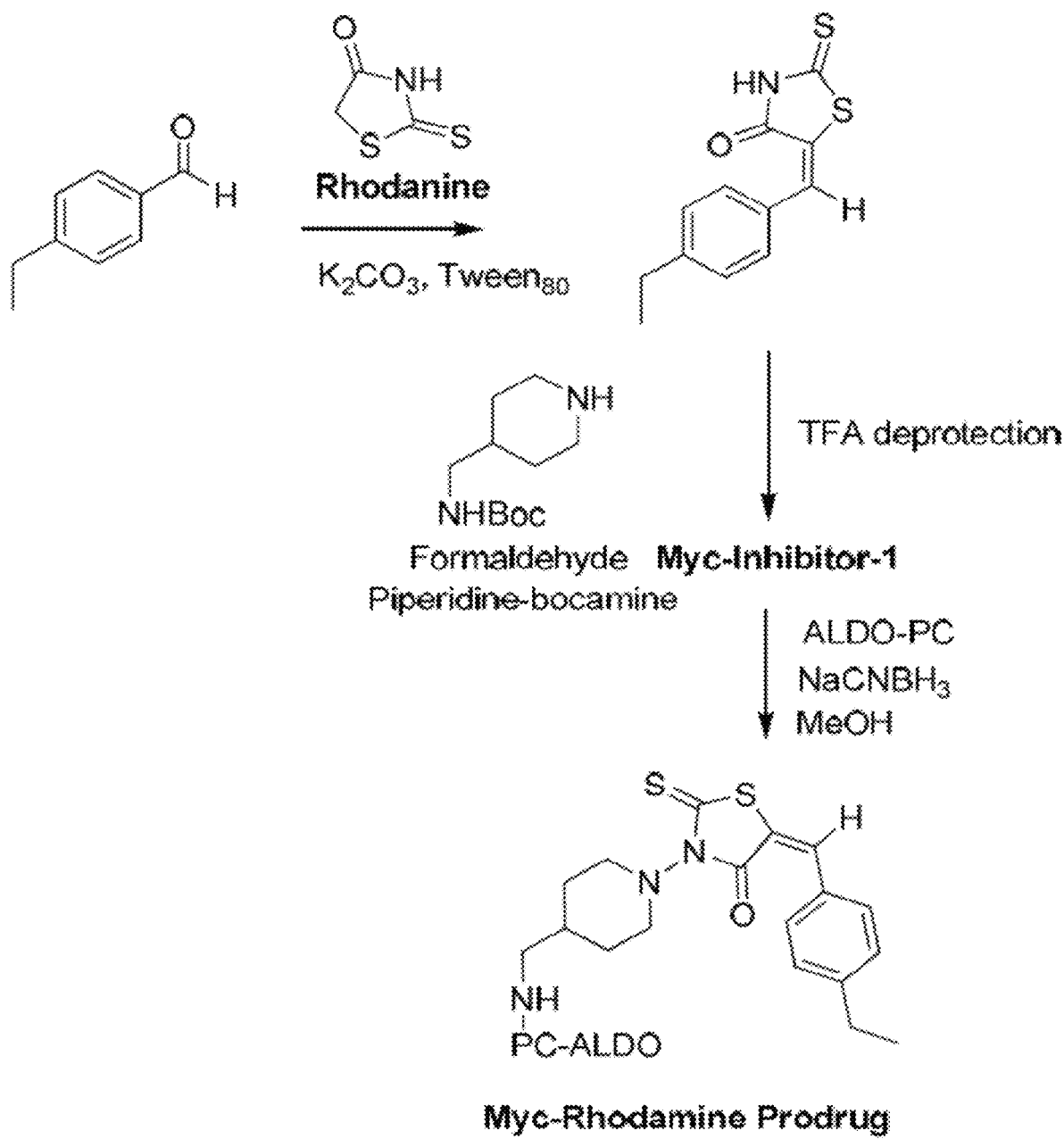
FIG. 14A-B depicts two synthesis schemes, specifically, the synthesis scheme of a myc-inhibitor prodrug (A) and an alternative variant (B).
Figure 14B:
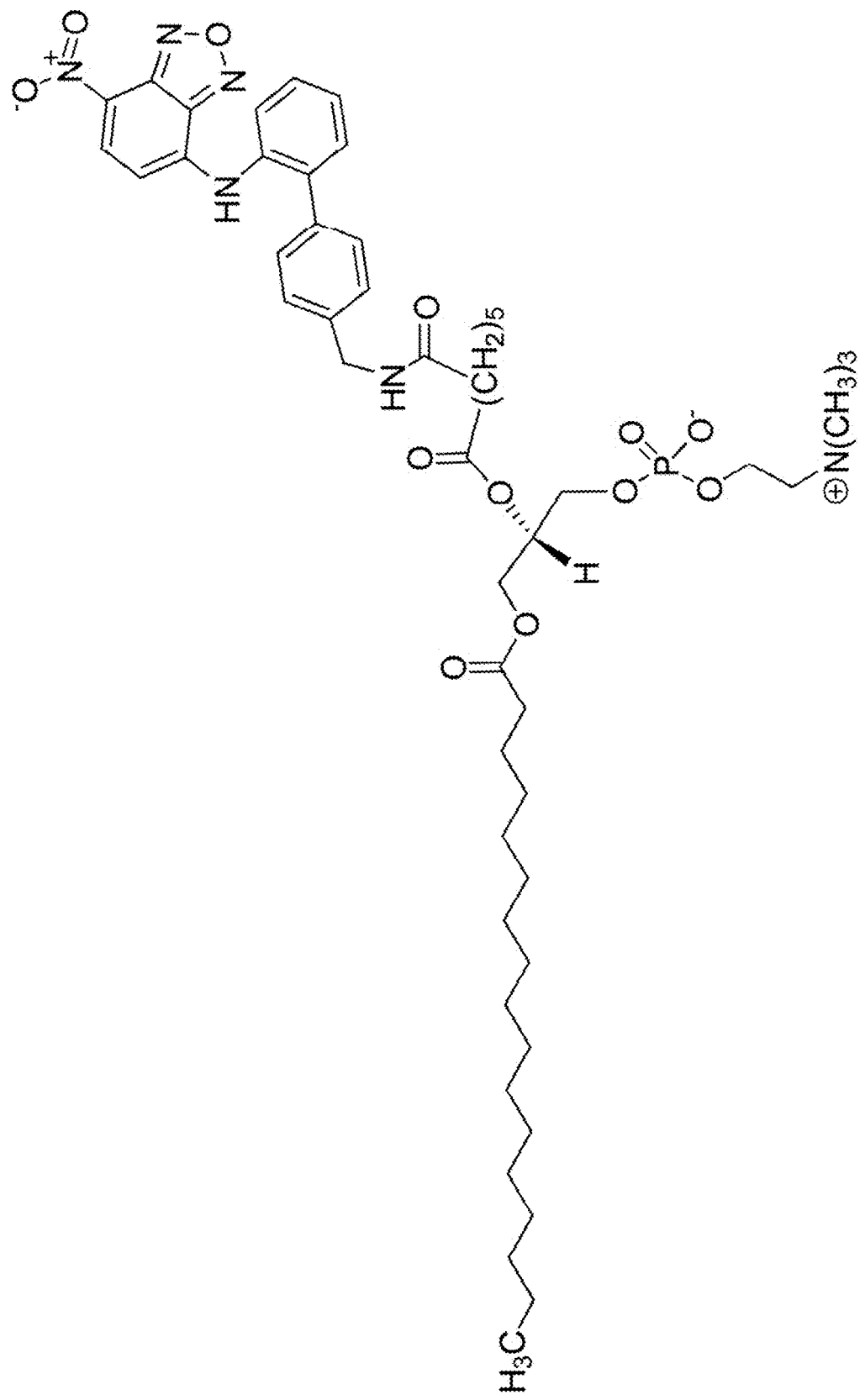
Figure 16:
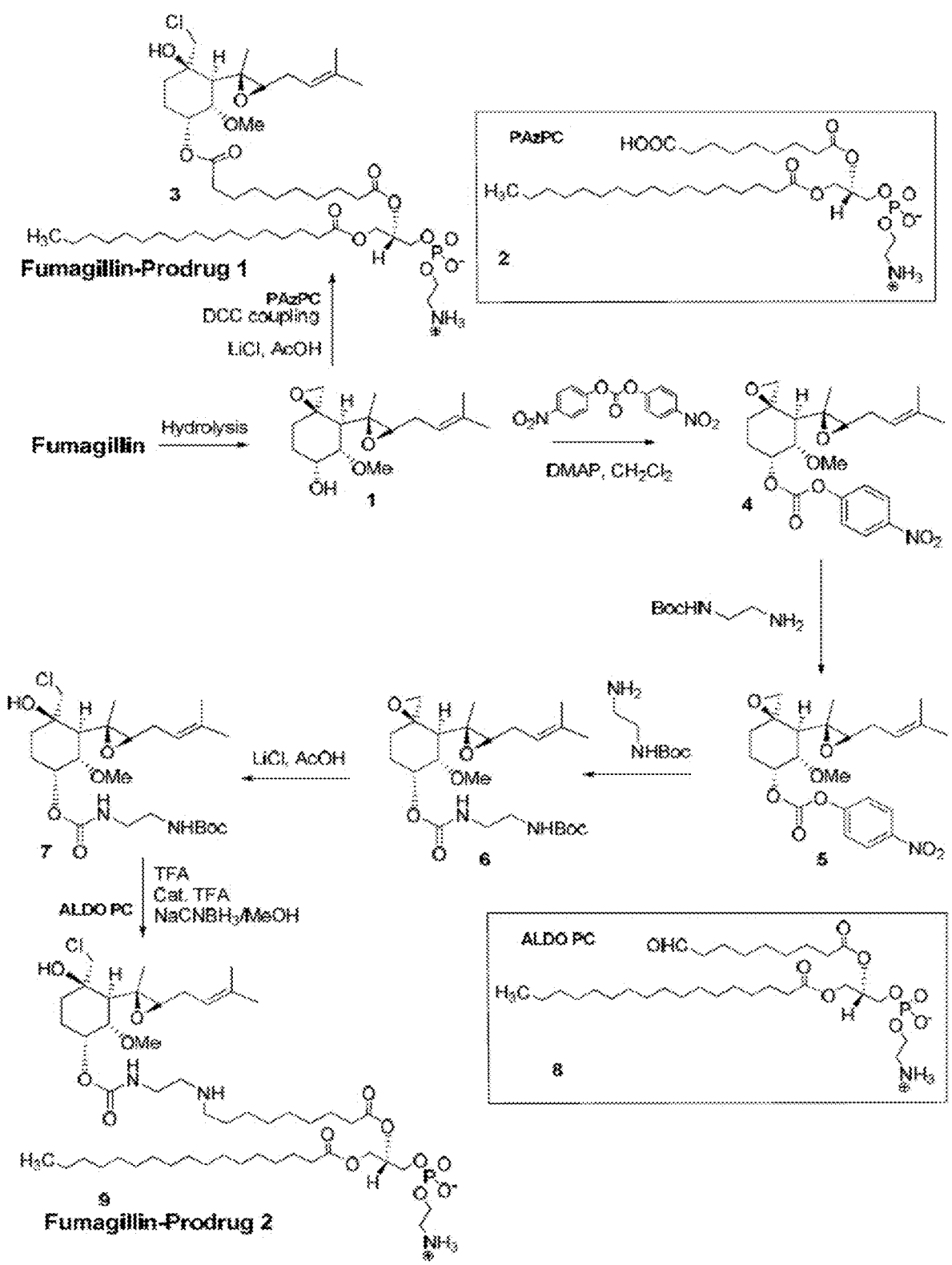
FIG. 16 depicts the synthesis scheme of fumagillin prodrugs 1(top) and fumagillin prodrugs 2 (bottom).
Figure 17:
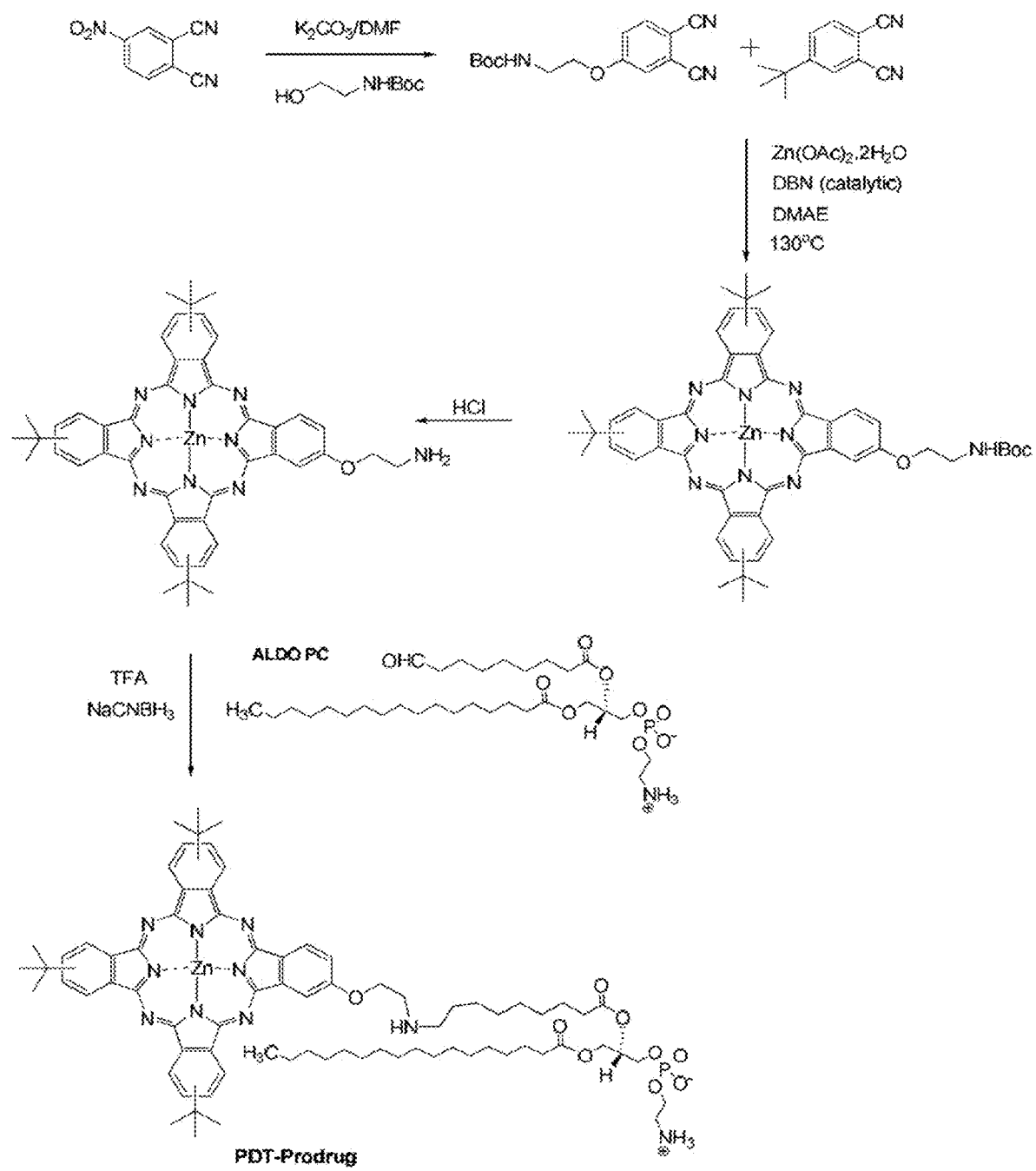
FIG. 17 depicts the synthesis scheme of photodynamic therapy (PDT) prodrugs.

Myc-inhibitor-1 may be synthesized (FIG. 14) by reacting 4-ethyl benzaldehyde with rhodanine in the presence of a catalytic amount of Tween-80 in potassium carbonate solution at ambient temperature. The mixture may be neutralized with 5% HCl and the precipitant may be treated with saturated $NaHSO_3$ and re-crystallized with aqueous ethanol. This rhodanine derivative may be reacted to piperidine-mono-tert Boc and formaldehyde. Deprotection of the tert Boc in presence of TFA may produce the Myc-inhibitor-1. Finally Myc-inhibitor-1 may undergo sodium cyano borohydride mediated reductive amination with ALDO (PC) in presence of catalytic amounts of TFA to produce the Myc-rhodanine prodrug.

Example 10: Myc-Inhibitor Prodrug in Restenosis

Myc encodes a helix-loop-helix transcription factor upregulated in 50-80% of human cancers and is associated with 100,000 US cancer deaths per year. Myc heterodimerizes with its partner Max to control target gene transcription and is deeply integrated into the regulatory and control mechanisms governing cell viability and proliferation. A recent estimate suggests that Myc binds to approximately 25,000 regions in the human genome. The loss of Myc proteins inhibits cell proliferation and growth, accelerates differentiation, increases cell adhesion, and accentuates the response to DNA damage.

We believe that Myc is an ideal target for anti-cancer therapeutics, particularly MM in which it is highly overexpressed by selective disruptive interference of Myc-Max dimerization while permitting Myc-Mad interactions.

Figure 28:
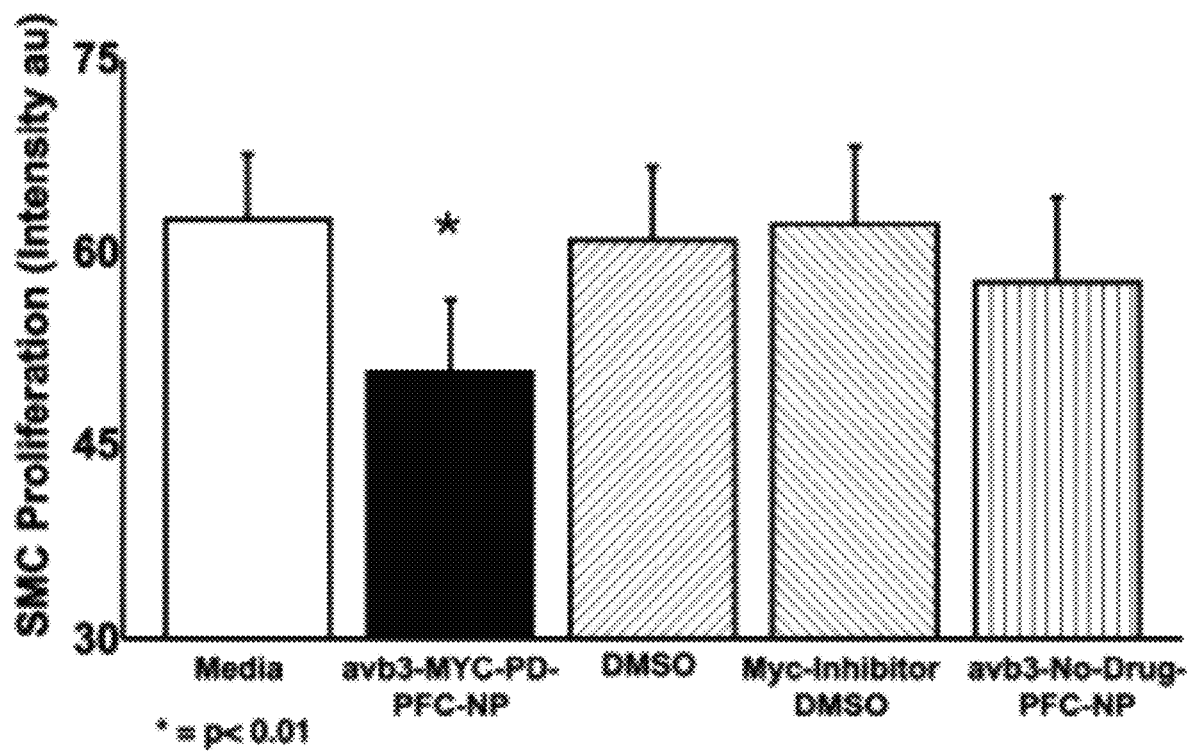
FIG. 28 depicts a graph illustrating that $\alpha v\beta 3$ targeted myc-prodrug PFC nanoparticles reduces SMC proliferation at 48 hours.
Figure 29:
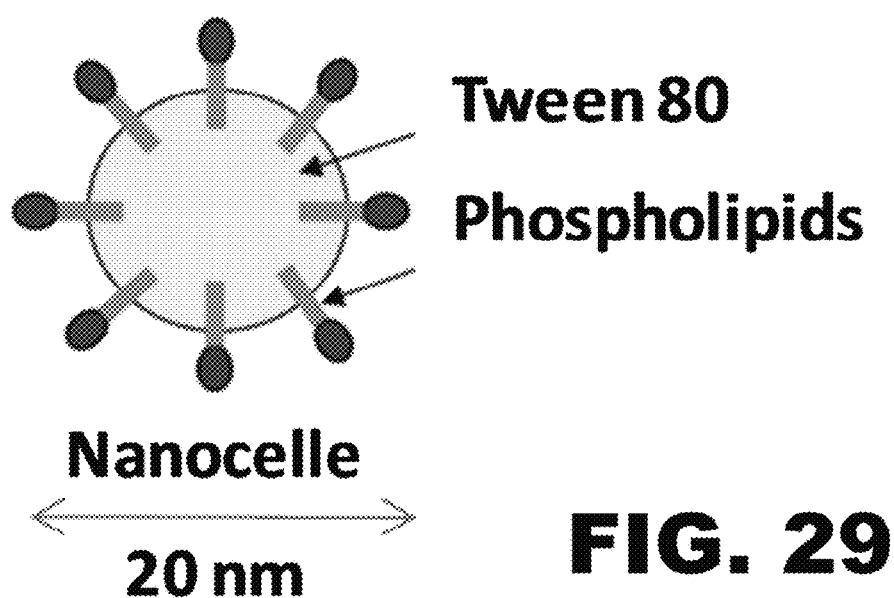
FIG. 29 depicts an illustration of a polysorbate micelle.

FIG. 28 illustrates that an αvβ3 targeted particle comprising a myc prodrug reduces SMC proliferation. Human coronary smooth muscle cells were plated on cover slips (2500 cells) and incubated 2 hours. Each treatment was replicated 6 times. The intramural delivery of an αvβ3 targeted particle comprising a myc prodrug, alone or with stents, offers an attractive new approach to restenosis.

Example 11. Synthesis of Lenalidomide Prodrugs

Lenalidomide is subjected to reductive amination in the presence of ALDO (PE) or (PC) in methanol (anhydrous) in the presence of catalytic amounts of TFA, followed by a one-pot reduction with $NaCNBH_3$ to produce lenalidomide-prodrug (FIG. 15).

Example 12. Synthesis of Fumagillin Prodrugs

Synthesis of the initial prodrug (fumagillin prodrug 1) was accomplished in a straightforward way by saponifying fumagillin to fumagillol dicyclohexylamine salt, which was then activated using DCC/DMAP mediated carbodiimide coupling protocol and then derivatized with oxidized lipid.

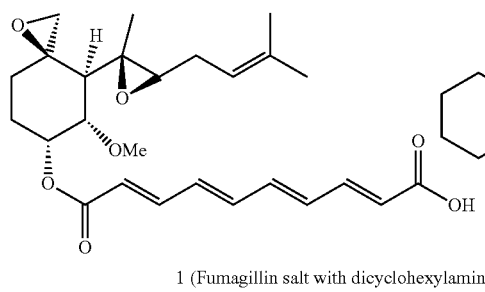
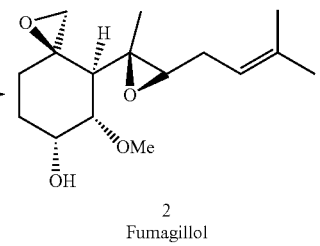

1 (Fumagillin salt with dicyclohexylamine)

2
Fumagillol

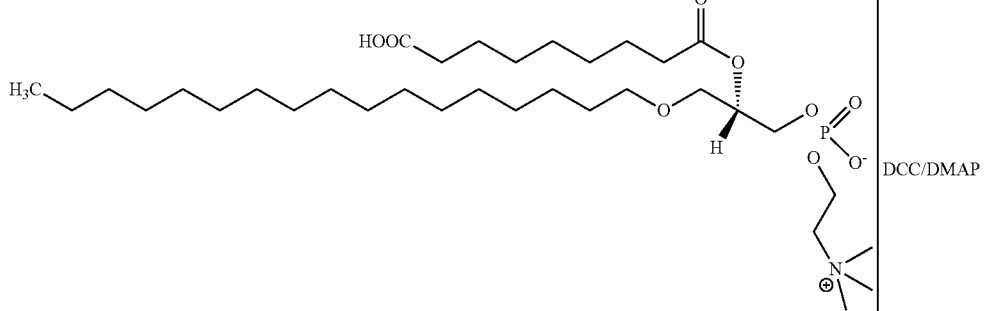

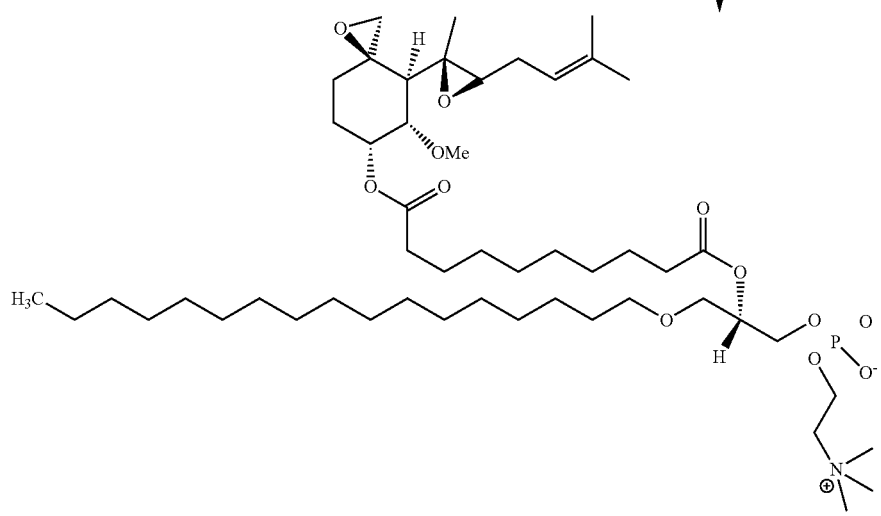

3
Fumagillin-Prodrug 1

(3R,4S,5S,6R)-5-Methoxy-4-((2R,3R)-2-methyl-3-(3-methylbut-2-enyl)oxiran-2-yl)-1-oxaspiro[2.5]octan-6-ol, (fumagillol, 2)

Fumagillin dicyclohexylamine salt (0.2 g, 0.31 mmol) was suspended in 2 mL of 1:1 methanol:water and treated with 0.07 mL of 35% NaOH solution (0.62 mmol). The dark-brown mixture was stirred in an ice bath for 2 h, then warmed to room temperature and treated with another equivalent of NaOH solution. The mixture was stirred until starting material was not detected by TLC (□4 h); the methanol was evaporated and the residue extracted into ethyl acetate. The mixture was then extracted with 5% citric acid, brine, bicarbonate, and brine again, then dried with $MgSO_4$ and concentrated in vacuo. The crude product was further purified by treatment with activated charcoal in acetonitrile and filtration through a celite pad. Concentration yielded a colorless solid, 59 mg (70%). HRMS found: MH+ (283.3).

General Procedure for the Preparation of Fumagillin Prodrug 1

A solution of C16-09:0 (COOH) PC 1-hexadecyl-2-azelaoyl-sn-glycero-3-phosphocholine (3.2 mmol) followed by DMAP (44 mg, 3.2 mmol) and DCC (46 mg, 3.2 mmol) were added to a solution of fumagillol (11 mg, 0.4 mmol) in dry dichloromethane (1 ml). The reaction mixture was stirred for overnight at room temperature then the mixture was passed over a short pad of silica gel using EtOAc/n-hexane (1:2, v/v) and the filtered solvent was removed in vacuo to leave an oil residue that was purified by column chromatography on SiO2 with EtOAc/n-hexane (1:4, v/v) as elution solvent to give the fumagillin prodrug 1 compound as a pale yellowish solid. HR-MS found: 991.5475 (M+2K-2H).

Other Strategies and Specific Examples

Figure 34:
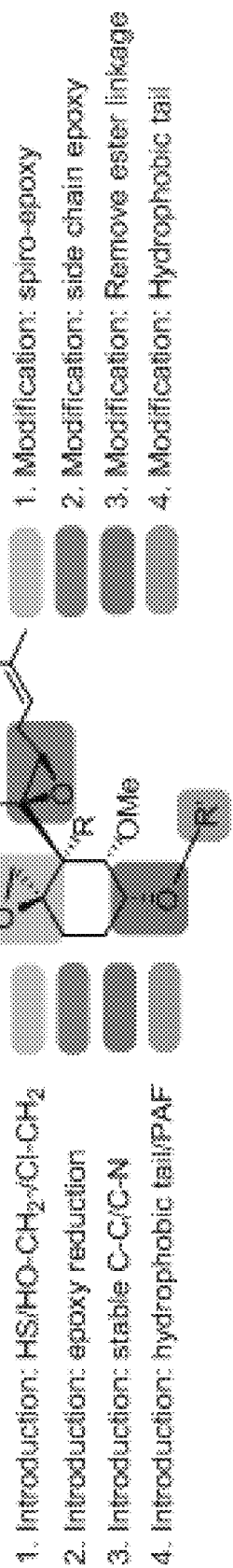
FIG. 34 depicts a scheme for creating fumagillin analogues.

The challenge of this step will be to develop photo and chemically robust analogs of fumagillin and its related candidates with improved membrane retention properties. One of the strategies would follow the removal of unstable and pharmacologically inactive (and irrelevant) functionalities from their structures and introduce hydrophobically similar moieties to the whole system. In the present invention, we design to substitute the all trans-decatetraenedioate with photostable, non-conjugated unsaturated chains. We will synthesize fumagillin analogs in which each of the potentially reactive epoxide groups will be substituted either individually or in combination. The ester linkage will be replaced by the incorporation of stable covalent bonds. A parallel strategy would allow the incorporation of moieties that would provide membrane adherence properties for these analogs. The decatetraenedioic tail will be substituted with hydrophobically comparable moieties. Synthetic methodologies for making fumagillin analogs have been explored by several groups and disclosed in the literature. We will develop efficient synthetic methodologies for the proposed analogs poised for further studies on detailed examination of its biological activity with significant therapeutic potential. (See FIG. 34.)

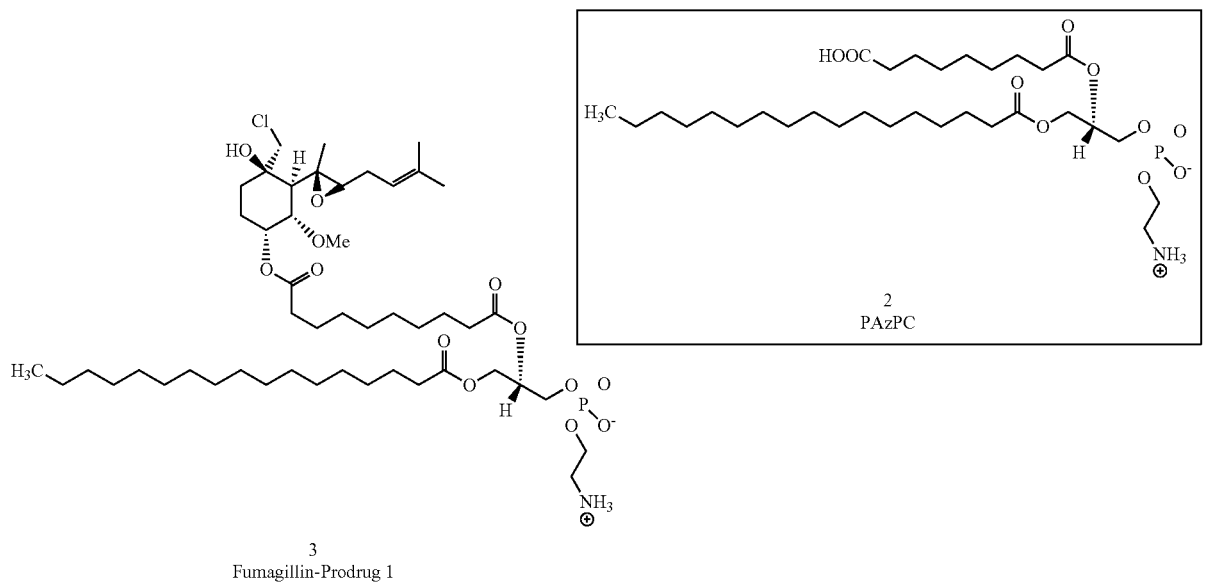

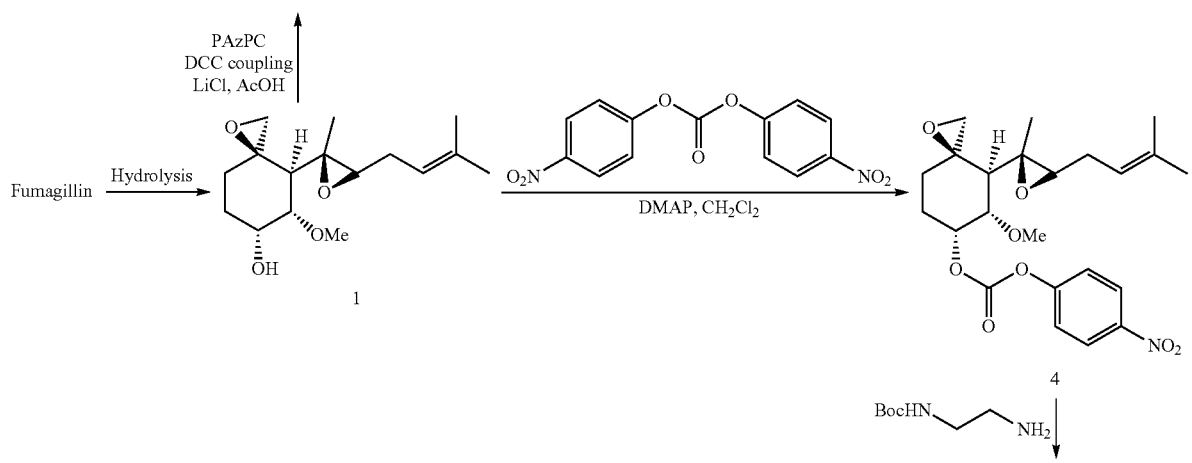

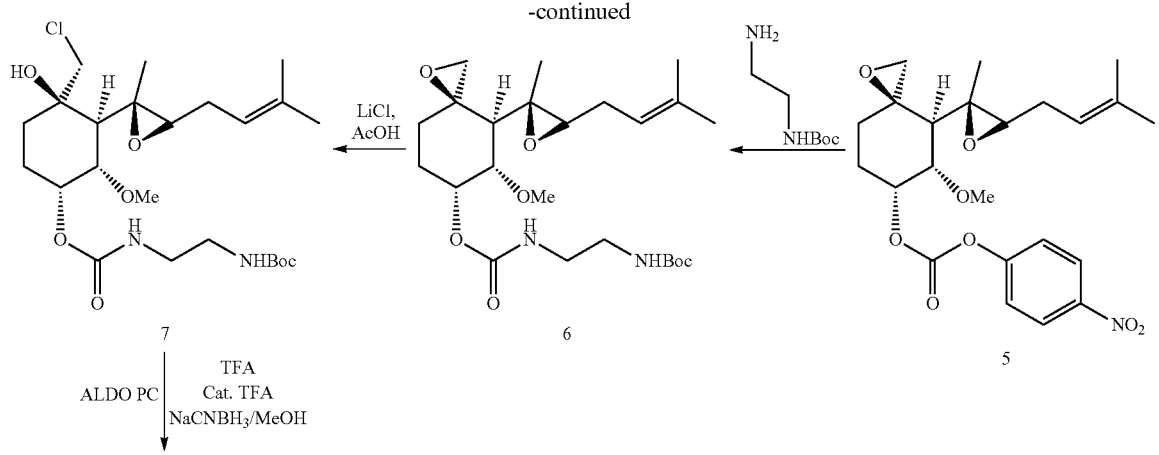

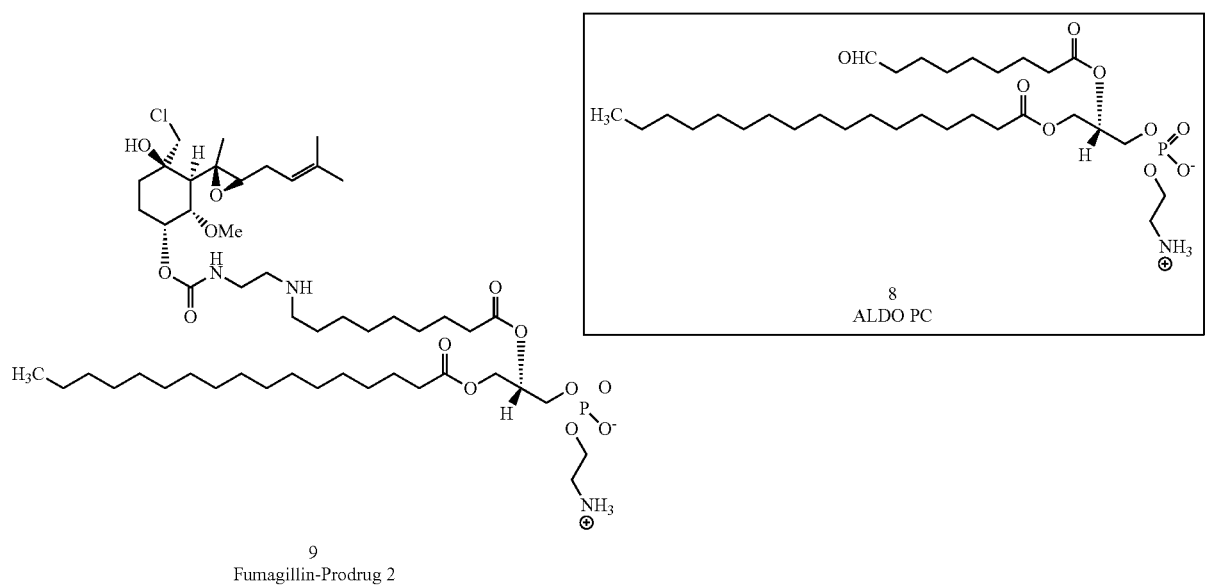

Synthesis of Stable Fumagillin Prodrug

Fumagillin Prodrug 1:

Fumagillol (1) will be produced by the hydrolysis of fumagillin and subjected to a DCC mediated coupling with commercially available PAzPC (16:0-9:0 COOH PC). The product will be recovered and immediately be subjected to reaction with LiCl in presence of acetic acid to open the spiro epoxide with chloro methyl functionality.

Fumagillin Prodrug 2:

Fumagillol will be activated with bis(4-nitrophenyl) carbonate followed by reacting with monoboc-ethylendimine to produce 6. In a typical experimental procedure, under a $N_2$ atmosphere, a mixture of fumagillol, bis(4-nitrophenyl) carbonate and DMAP in dry $CH_2Cl_2$ will be stirred for 7 h. The reaction mixture will be diluted with $CH_2Cl_2$ and washed with $H_2O$. The organic layer will be dried ($Na_2SO_4$) and concentrated. Flash chromatography (EtOAc-hexane) will be used to yield the activated fumagillol. Monoboc-protected ethylendiamine will then be coupled to prepare intermediate-6. The product will be recovered and immediately be reacted with LiCl in presence of acetic acid to open the spiro epoxide with chloro methyl functionality. The boc will be deprotected with TFA and the product will be subjected to sodium cyano borohydride mediated reductive amination in presence of the ALDO PC.

Synthesis of the Precursor Compounds:

Ovalicin (4) will be synthesized following a literature procedure by Takahashi et al.[40a] A commercially available 2, 3:5, 6-di-O-isopropylidene-R-D mannofuranose will be used as a starting material to produce optically pure ovalicin in 10% overall yield. Fumagillol will be purchased from Sinova, Inc. and used as received.

Fumagillol will be subjected to oxidation using pyridinum chlorochromate (PCC)/pyridine to produce Fumaginone (3). In a typical experimental procedure, a mixture of fumagillol (1 equiv.), pyridinium chlorochromate (PCC, 8 equiv.) and pyridine (5 equiv.) in anhydrous $CH_2Cl_2$ is allowed to stir for 10 h at ambient temperature and the completion of the reaction is monitored by thin layer chromatography. The reaction mixture is purified by silica gel column chromatography (EtOAc—$CH_2Cl_2$) to give fumaginone as clear oil.

Scheme 1. Synthesis of analog 1-2 from ovalicin and fumaginone precursorssors

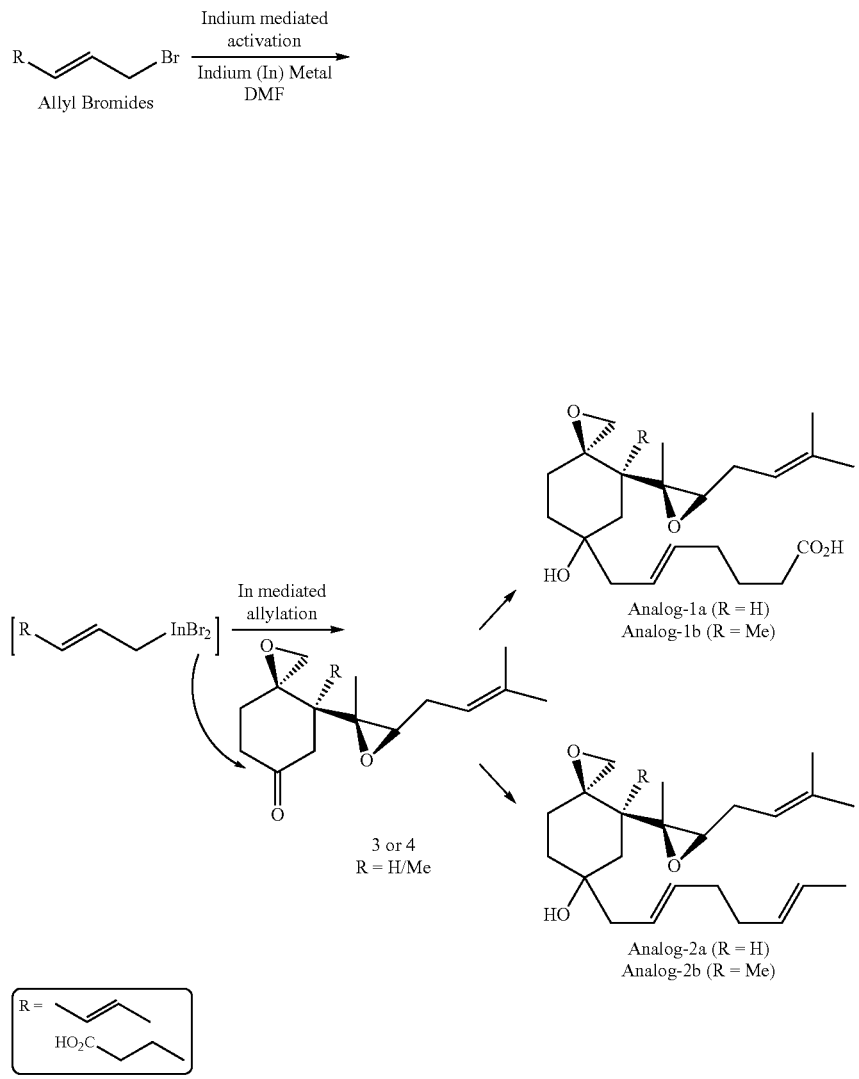

Synthetic Analogs 1-2

As briefly discussed above, in the present invention, we design to substitute the all trans-decatetraenedioate with photo stable, non-conjugated unsaturated chains (analog 1-2). Thus, analogs 1-2 bearing a variety of non-conjugated substituent at the hydrophobic tail will be prepared with either hydrogen (fumagillin series) or hydroxyl group (ovalicin series). Briefly, the precursor compounds will be subjected to indium mediated organometallic allylation with respective substituted allyl bromides.

Scheme 2. Synthesis of analog 3-6 from ovalicin and fumaginone precursors.

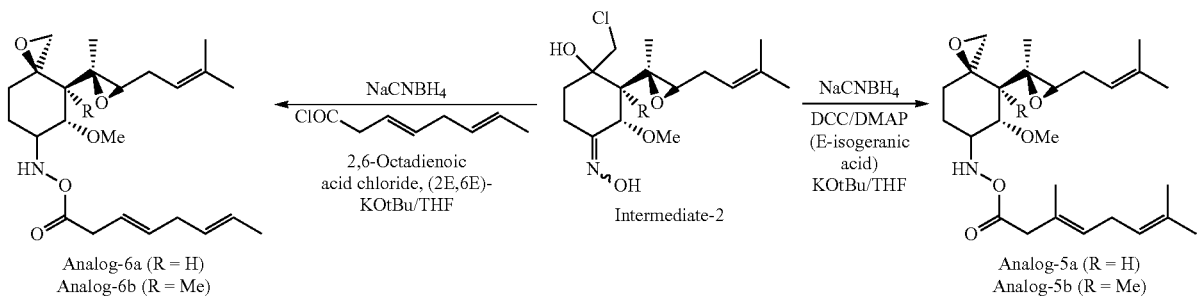

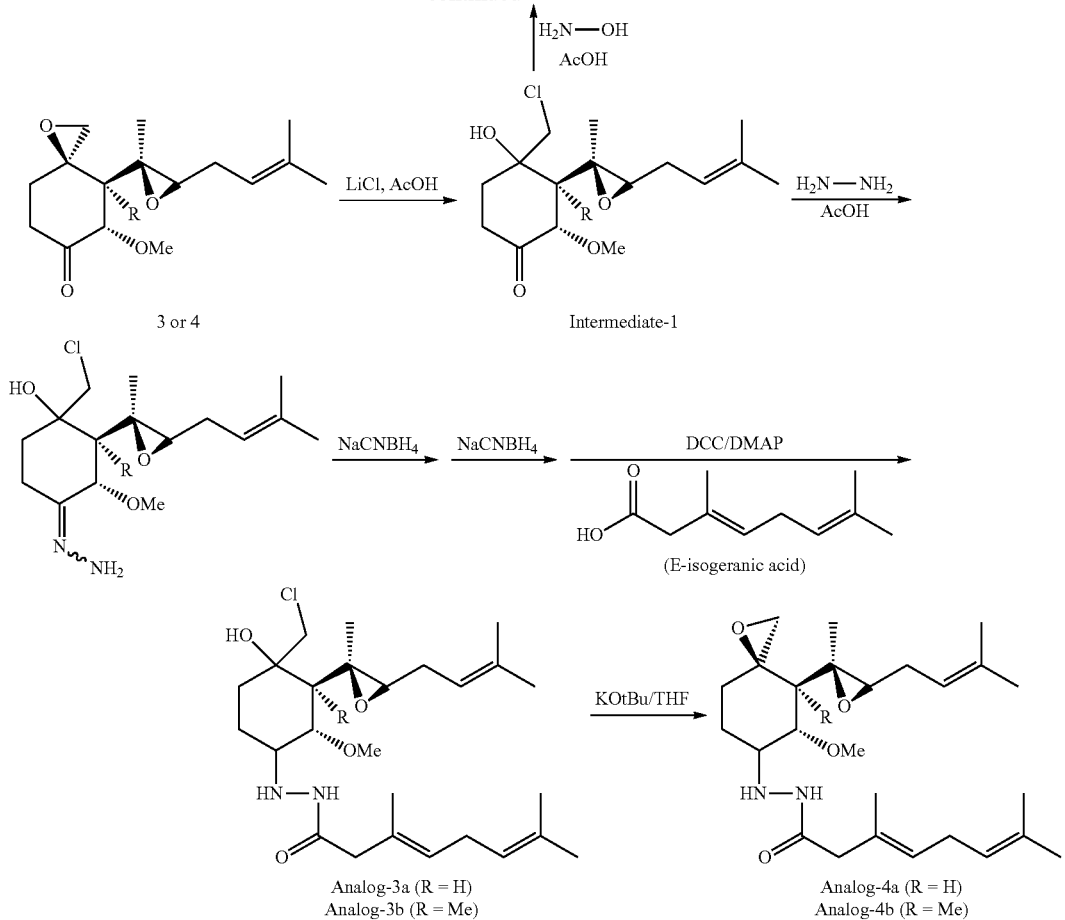

Analogs 3-6

Analog-3 can be synthesized from ovalicin-hydrazone. Briefly, ovalicin (or fumaginone) will be treated with LiCl in presence of acetic acid to open the spiro epoxide with chloro methyl functionality. A solution of ovalicin in THF is stirred with LiCl and Acetic acid for 36 h and worked up by removal of THF, followed by addition of chloroform. The organic layer is washed with $H_2O$, sodium bicarbonate, dried and purified by silica chromatography (30% EtOAc-hexane).

This intermediate will be treated next with hydrazine under mild acidic condition (acetic acid) to afford the the corresponding hydrazone. Hydrazone will then be subjected to selective reduction with sodium cyano borohydride followed by DCC/DMAP mediated amidation in presence of the respective acid (E-isogeranic acid)[40e] (Scheme 2). In the final step, spiro epoxide functionality will be optionally reformed. Analog 3 will be treated with KOtBu in THF at 0° C. to afford analog-4 containing reformed spiro epoxide moiety.

In a separate pathway, intermediate-1 will be treated with hydroxyl amine in presence of a mild acid to afford the corresponding oxime derivative. The oxime derivative will be reduced, followed by a DCC-mediated esterification with E-isogeranic acid will produce analog 5. 2,6-Octadienoic acid chloride may be also be used to esterify the oxime (analog 6).

E-isogeranic acid will be synthesized from E-isogeraniol by following a literature report by Eustache and coworkers.[40e] E-isogeraniol will be subjected to a chromium trioxide mediated oxidation in presence of sulfuric acid in water and acetone mixture to afford the desired E-isogeranic acid. The acid will be obtained in the pure enantioselective E-form and separated from byproducts by passing through a silica column. In a straightforward way, 2,6-Octadienoic acid, (2E,6E)—will be converted to acid chloride by treating it with $PCl_5$.[41]

Scheme 3: Synthesis of analog 7-9 from ovalicin and fumaginone precursors.

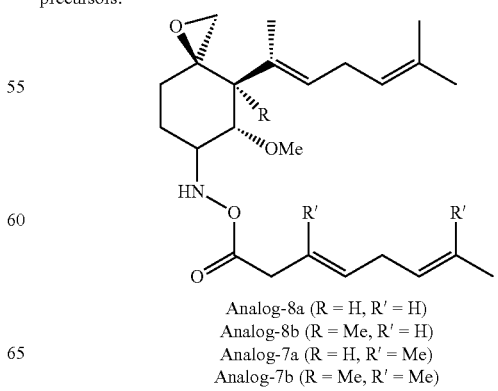

Analog-8a (R = H, R' = H)
Analog-8b (R = Me, R' = H)
Analog-7a (R = H, R' = Me)
Analog-7b (R = Me, R' = Me)

-continued

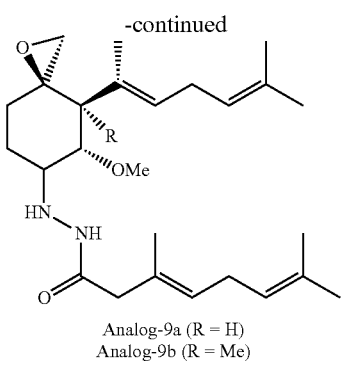

Analog-9a (R = H)
Analog-9b (R = Me)

Analog 7-9

Based on a previous report by Liu et al,[42] compounds carrying a rotatable single bond between C10 and C20 carbons on the C4 side chain exhibited a reduced activity against MetAP-2 in comparison to analogs with rigid epoxide and diene side chains. Also a crystallographic data indicated that that there was significant space within the pocket for further optimization.[42] All together, we decided to replace the acid labile side chain epoxide with a diene moiety.

In a typical experimental procedure, analog-5 will be treated with $WCl_6$ in presence of n-BuLi at −78° C. followed by a KOtBu in THF at 0° C. to afford analogs 7 (scheme 3). Under argon atmosphere, n-BuLi is added dropwise to a solution of $WCl_6$ in THF at −78° C. followed and allowed to stir for ½ h. A solution of analog-5 is added and allowed to react for 2 h. NaOH is added to the reaction mixture and the product is extracted with ether. The extracts were washed with NaOH, and water. The residue was purified by column chromatography (ethyl acetate-hexane) to yield analog-7. Analogs 8-9 will be synthesized from analogs-4 and 6 respectively by following the routes described above for the synthesis of analog-7.

Scheme 4. Synthesis of analog 10-11 from ovalicin and fumaginone precursors.

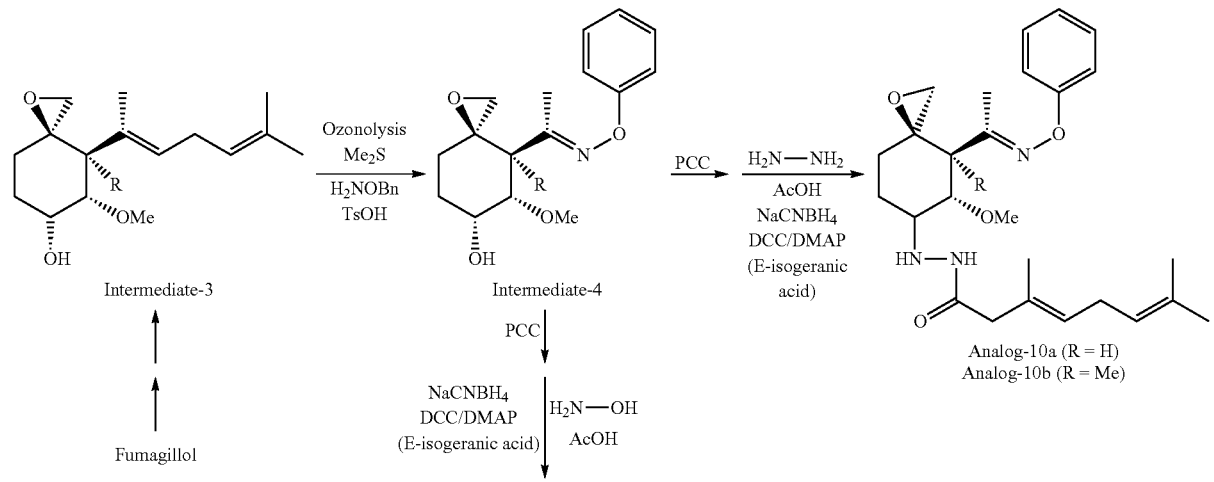

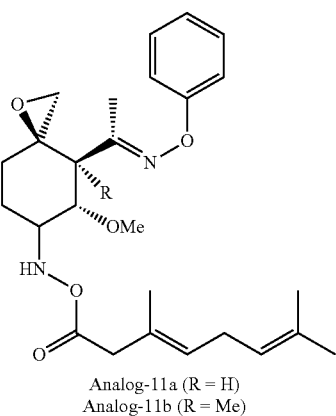

Analog-11a (R = H)
Analog-11b (R = Me)

Analogs 10-11

We will also replace the exocyclic side chain epoxide with an oxime functionality which may provide the desired geometry and substitution pattern. Previous report by Pyun et al[40m] showed that benzyloxime bearing analogues exhibited excellent activities (~1 nM in the MetAP-2 assay.[40m] A C4 oxime analog will be synthesized and evaluated. The intermediate 3 can be easily synthesized from fumagillol as reported previously by Fardis et al.[40b] The intermediate-3 will be subjected to ozonolysis at −78° C. followed by treatment with dimethyl sulphide to afford the corresponding keto derivative. The keto derivative will be treated with amino benzyl oxime ($H_2N$—OBn) in presence of TsOH and molecular sieves (4 Å) to produce a mixture of E and Z benzyl oxime (intermediate 4). Intermediate-4 will then be oxidized to the corresponding keto derivative. Treatment of intermediate-4 with hydrazine or hydroxyl amine will generate the corresponding oxime derivative which will then be reduced and activated with DCC/DMAP to react with E-isogeranic acid to produce analogs 10-11.

Diagram 4. Synthesis of analog 12-15 from ovalicin and fumaginone precursors.

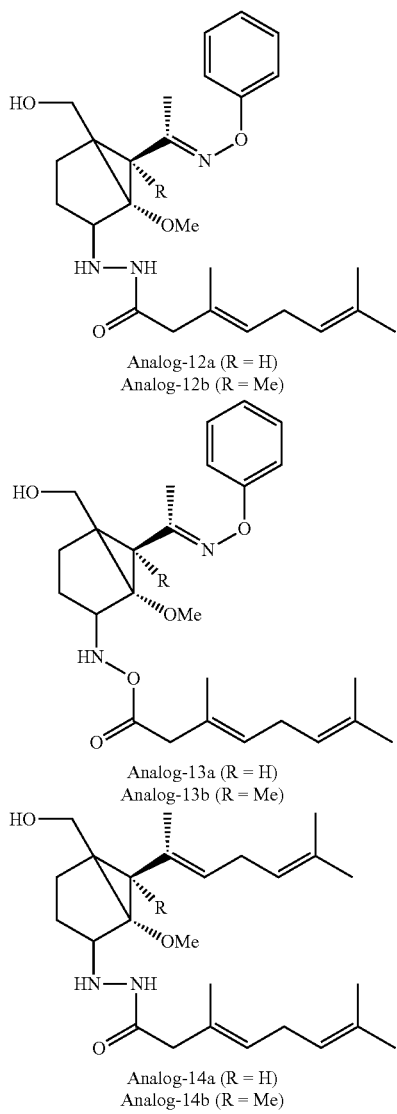

Analog-12a (R = H)
Analog-12b (R = Me)

Analog-13a (R = H)
Analog-13b (R = Me)

Analog-14a (R = H)
Analog-14b (R = Me)

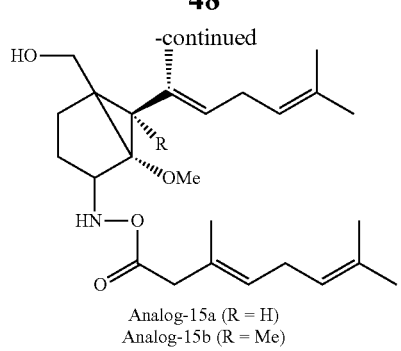

Analog-15a (R = H)
Analog-15b (R = Me)

Analogs 12-15

Fumarranol is a novel synthetic analog of fumagillin which has been shown to selectively inhibits MetAP2 and endothelial cell proliferation without covalently binding MetAP-2.[40g] Fumarranol consist of a bicyclic ring structure with an opened up spiro epoxy moiety. We decided to explore related fumarranol analogs along the strategy discussed above. Analog-10 will be reacted with KOH to form a carbanion at the R-position of the 6-ketone group which undergoes an intramolecular SN2 type reaction to open the spiro epoxide group (Diagram 4) to produce a bicyclic ring structure (analog 12). Similarly, analogs 13-15 will be synthesized from analog 7 and 8 respectively.

Diagram 5. Synthesis of analog 16-19 from ovalicin and fumaginone precursors

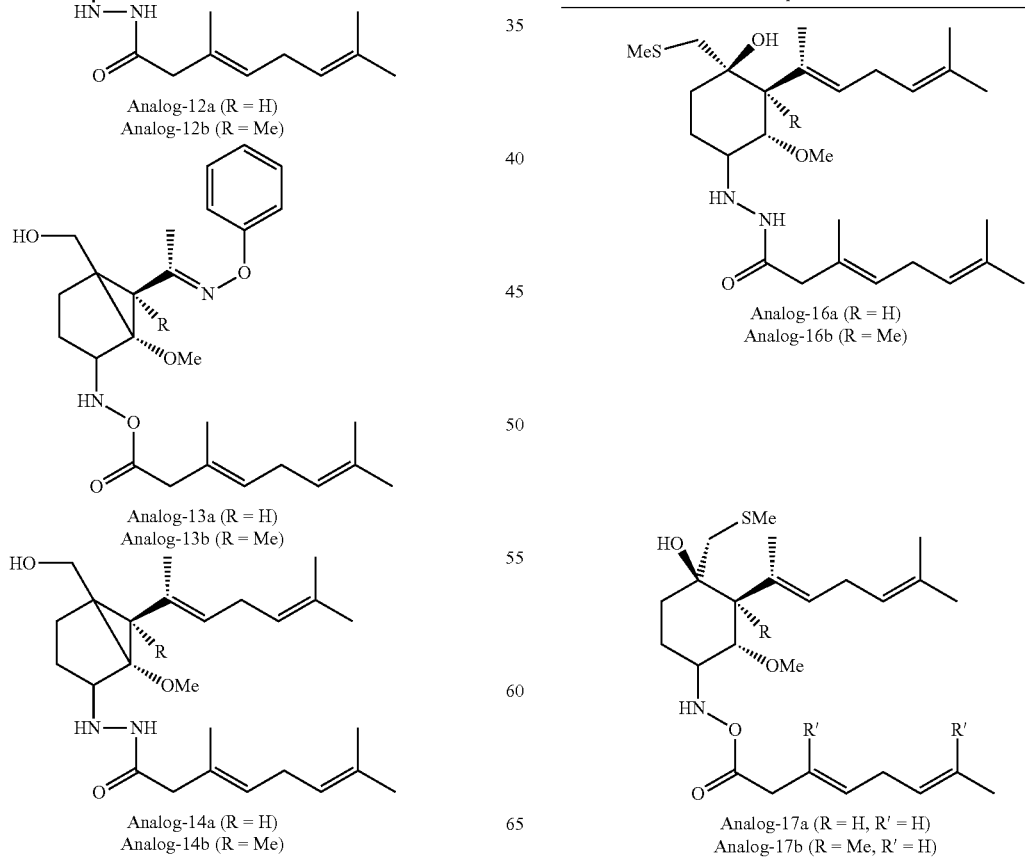

Analog-16a (R = H)
Analog-16b (R = Me)

Analog-17a (R = H, R' = H)
Analog-17b (R = Me, R' = H)

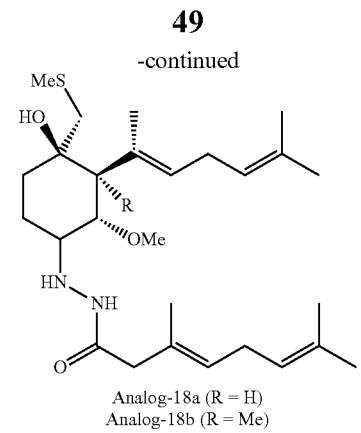

Analog-18a (R = H)
Analog-18b (R = Me)

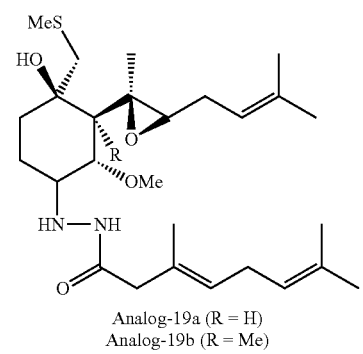

Analog-19a (R = H)
Analog-19b (R = Me)

Analogs 16-19

We will also undertake the synthesis of analogs in which the spiro (C-3) epoxide will be opened with thiomethoxide (Scheme 5) functionality. Briefly, to a stirred solution of analog-7 in anhydrous DMF will be added thiomethoxide at room temperature. The reaction mixture is stirred for 2 h, then diluted with ethyl acetate and washed with saturated aqueous $NaHCO_3$ and water. The organic phase is dried (anhydrous $Na_2SO_4$) and the residue is purified by column chromatography on silica gel (ethyl acetate:hexane) to produce analogs-16. Following a similar methodology, analogs 17-19 will be synthesized starting from analog 8-9 and 4 respectively.

Scheme 5. Synthesis of analog-20 from ovalicin and fumaginone precursors.

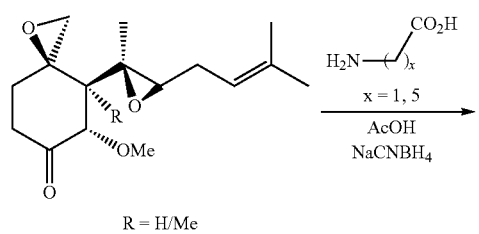

R = H/Me

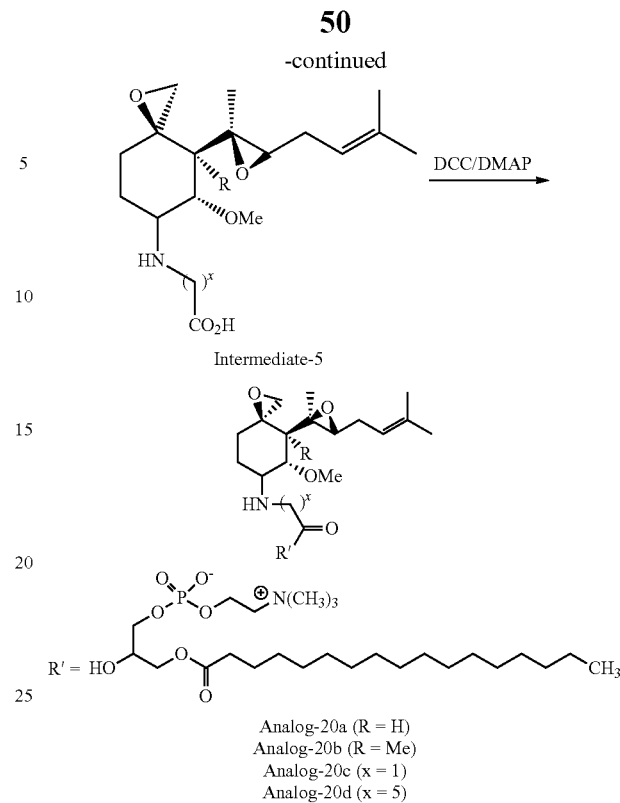

Intermediate-5

Analog-20a (R = H)
Analog-20b (R = Me)
Analog-20c (x = 1)
Analog-20d (x = 5)

Scheme 6. Synthesis of analog 21 from fumagillol.

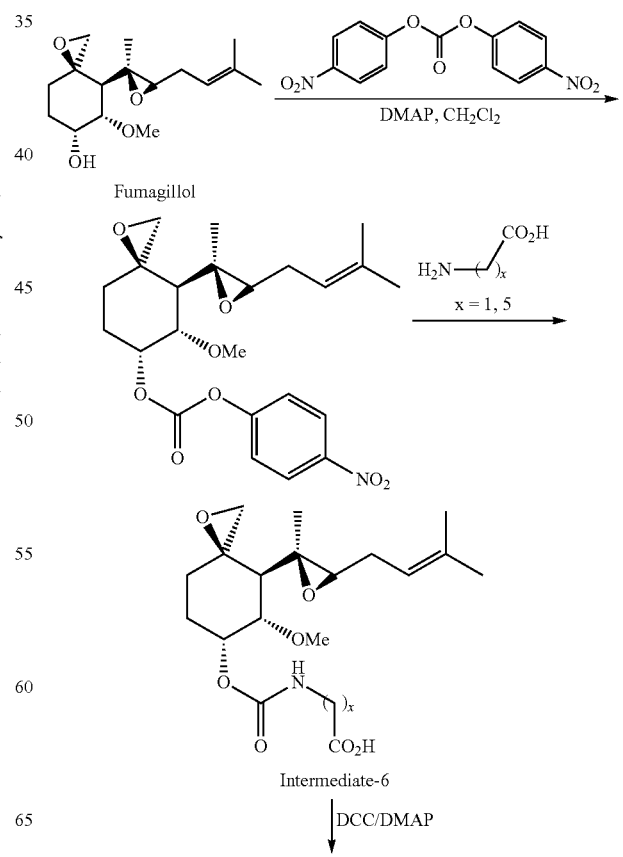

Fumagillol x = 1, 5

Intermediate-6

↓ DCC/DMAP

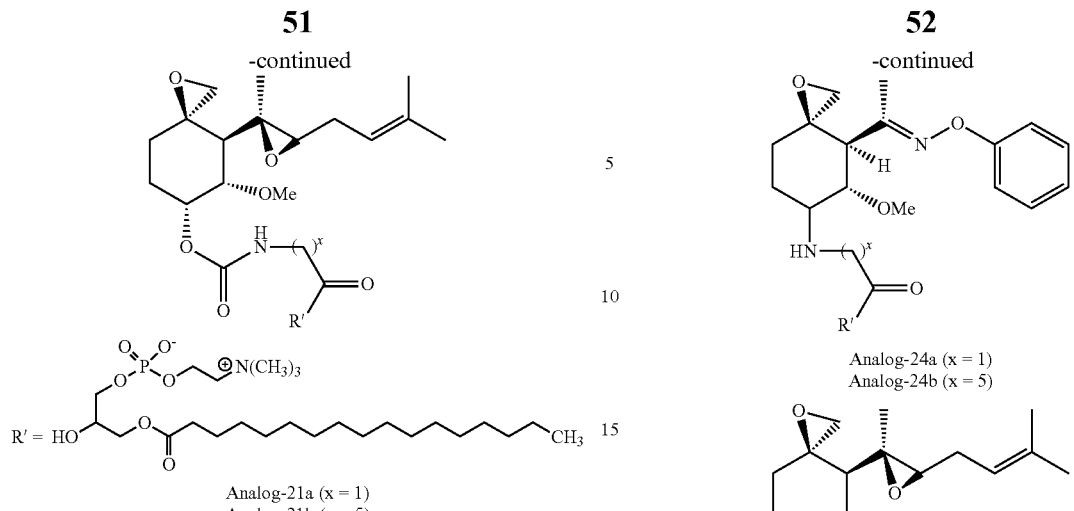

Analog-21a (x = 1)
Analog-21b (x = 5)

Synthetic Analogs 20-25 (Fumagillin-PAF Analogs

As described before, one of the challenges of this step will be to develop new fumagillin analogs with improved membrane adherence properties. Towards this aim, a series of Fumagillin-PAF analogues also targeted at understanding the tolerability of MetAP2 toward substitution at C4 and C6 will be synthesized. Initially, the C4 side chain will be maintained unaltered and C6 will be modified. Placement of a platelet activation factor (PAF)-lipid (16:0) at C6 is expected to improve the membrane adherence characteristics of these compounds. We plan to use a short (glycine) and a medium spacer (ε-amino caproic acid) as a flexible part of the analog providing a connection between the carbocyclic ring and the hydrophobic tail (Scheme 5 and 6). The linker molecule may play in important part in driving the enzymatic hydrolysis of the PAF conjugated fumagillin candidates. The impact of the linker length on the degradation of phospholipid-prodrug was previously investigated by Dahan et al.[28f] A shorter linker (2-carbon) was found to cause a 20-fold less release of the prodrug in comparison to a 5-carbon linker.[28f] Briefly, ovalicin (or fumaginone) will be treated with ε-amino caproic acid in presence of a mild acidic condition (acetic acid) to afford the corresponding hydrazone. The hydrazone will be selectively reduced with sodium cyano borohydride followed by DCC/DMAP mediated amidation in presence of PAF (16:0) resulted analogs-20.

Diagram 6. Structures of proposed fumagillin analog 22-27.

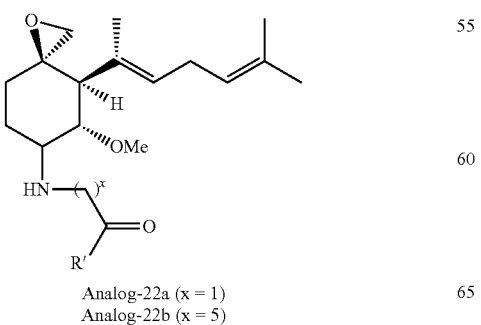

Analog-22a (x = 1)
Analog-22b (x = 5)

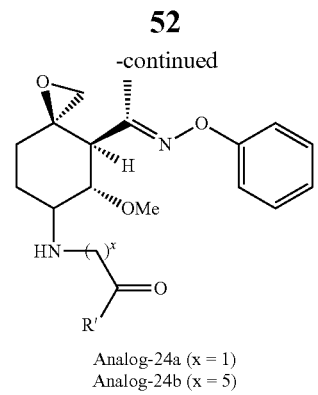

Analog-24a (x = 1)
Analog-24b (x = 5)

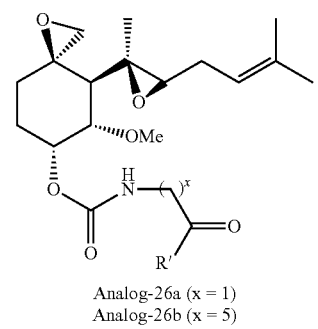

Analog-26a (x = 1)
Analog-26b (x = 5)

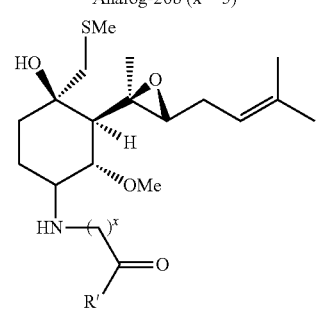

Analog-23a (x = 1)
Analog-23b (x = 5)

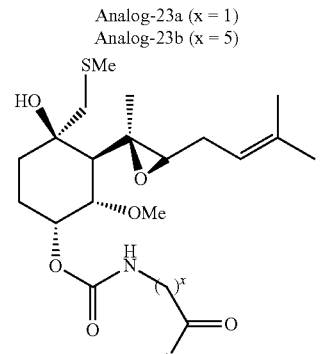

Analog-25a (x = 1)
Analog-25b (x = 5)

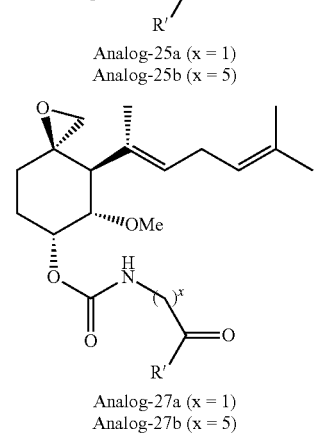

Analog-27a (x = 1)
Analog-27b (x = 5)

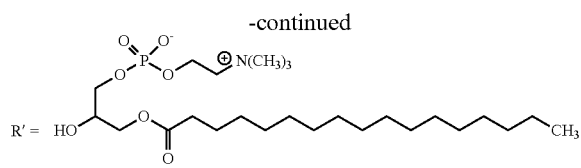

Alternatively, fumagillol will be activated with bis(4-nitrophenyl) carbonate followed by reacting with glycine. In a typical experimental procedure, under a $N_2$ atmosphere, a mixture of fumagillol, bis(4-nitrophenyl) carbonate and DMAP in dry $CH_2Cl_2$ is stirred for 7 h (scheme 6). The reaction mixture is diluted with $CH_2Cl_2$ and washed with $H_2O$. The organic layer is dried ($Na_2SO_4$) and concentrated. Flash chromatography (EtOAc-hexane) yielded the activated fumagillol. Glycine will then be coupled to prepare intermediate-6. Briefly, Under a $N_2$ atmosphere, a solution of activated fumagillol, glycine and DMAP in dry $CH_2Cl_2$ is stirred for 2 h. The completion of the reaction is monitored by thin layer chromatography. The reaction mixture is worked up by diluting with $CH_2Cl_2$ and washing the organic layer with $H_2O$. Removal of the solvent followed by flash chromatography (MeOH-EtOAc) resulted in intermediate-6. Finally a carbodiimide mediated esterification (DCC/DMAP) of intermediate-6 with PAF (16:0) agent will produce analog 21.

After placing the PAF agent at C6, the C4 side chain modification of fumagillin will be conducted to develop MetAP-2 inhibitors with desirable pharmacological properties. The spiro epoxide rings of analog 18 and 19 will be opened up with thiomethoxide to produce analogs 23 and 25. Replacement of the C4 side chain by benzyl oxime and diene side chains will be pursued to afford analogs 22, 24, 26-27 (Diagram 6).

Characterization of the Synthetic Fumagillin Analogs:

Detailed characterization of the synthetic Fumagillin analogs will be performed by NMR, FT-IR, mass spectrometry and elemental analyses. The $^1H$ and $^{13}C$ signal assignments and spatial proximity of protons will be based on COSY, NOE experiments. The $^1H$ and $^{13}C$ signal assignments will be made based on COSY, NOESY and selective 1DTOCSY13 measurements. The proton-proton coupling constants of the aliphatic moiety of the molecule will be determined by a first-order approximation from the 1H NMR spectrum after Gaussian apodization for resolution enhancement. The investigation of the cyclohexyl ring and the C-4 side chain will be done in a similar ways.

Example 13: Fumagillin Prodrug Efficacy

Figure 19A:
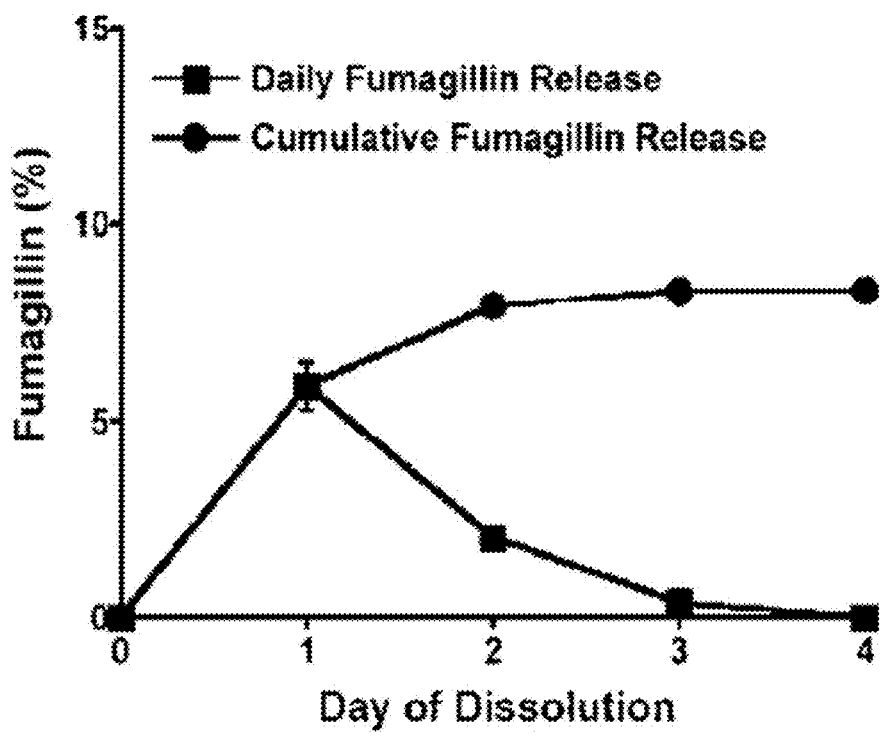
FIG. 19A-B depicts two graphs illustrating that fumagillin dissolved in a lipid membrane is stable in vitro but rapidly lost in vivo. (A) In vitro release of fumagillin is sustained over 4 days. (B) In vivo release of fumagillin occurs in a matter of minutes.
Figure 19B:
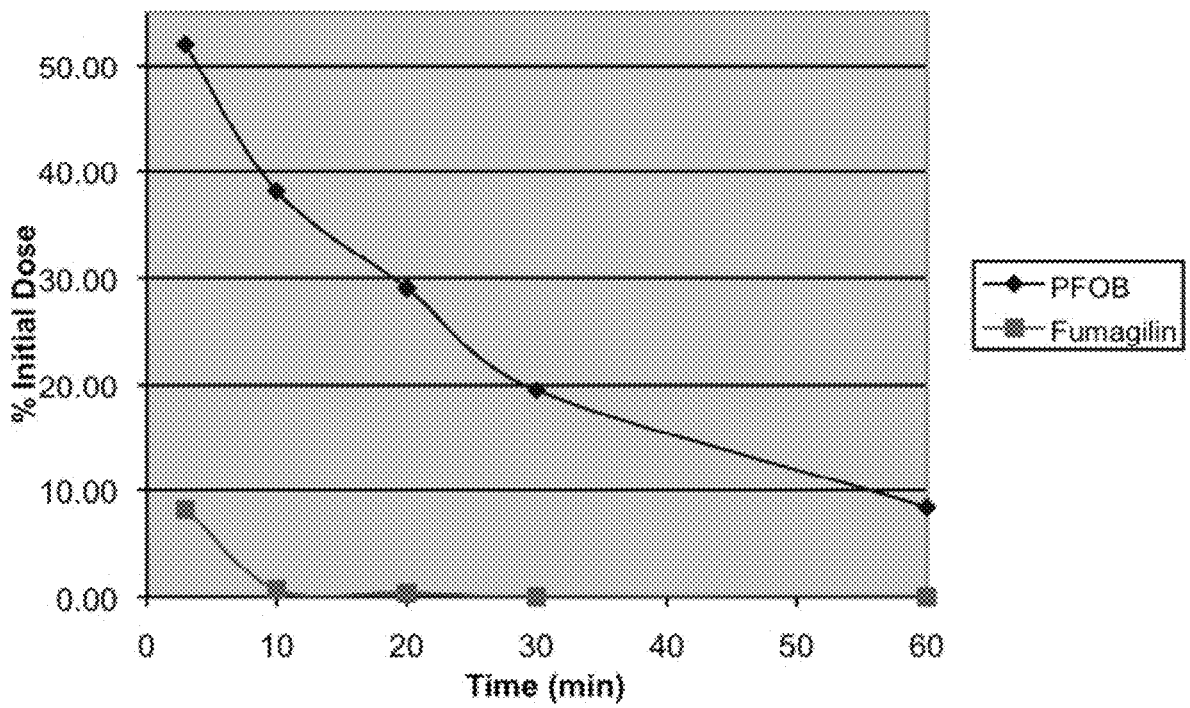
Figure 20:
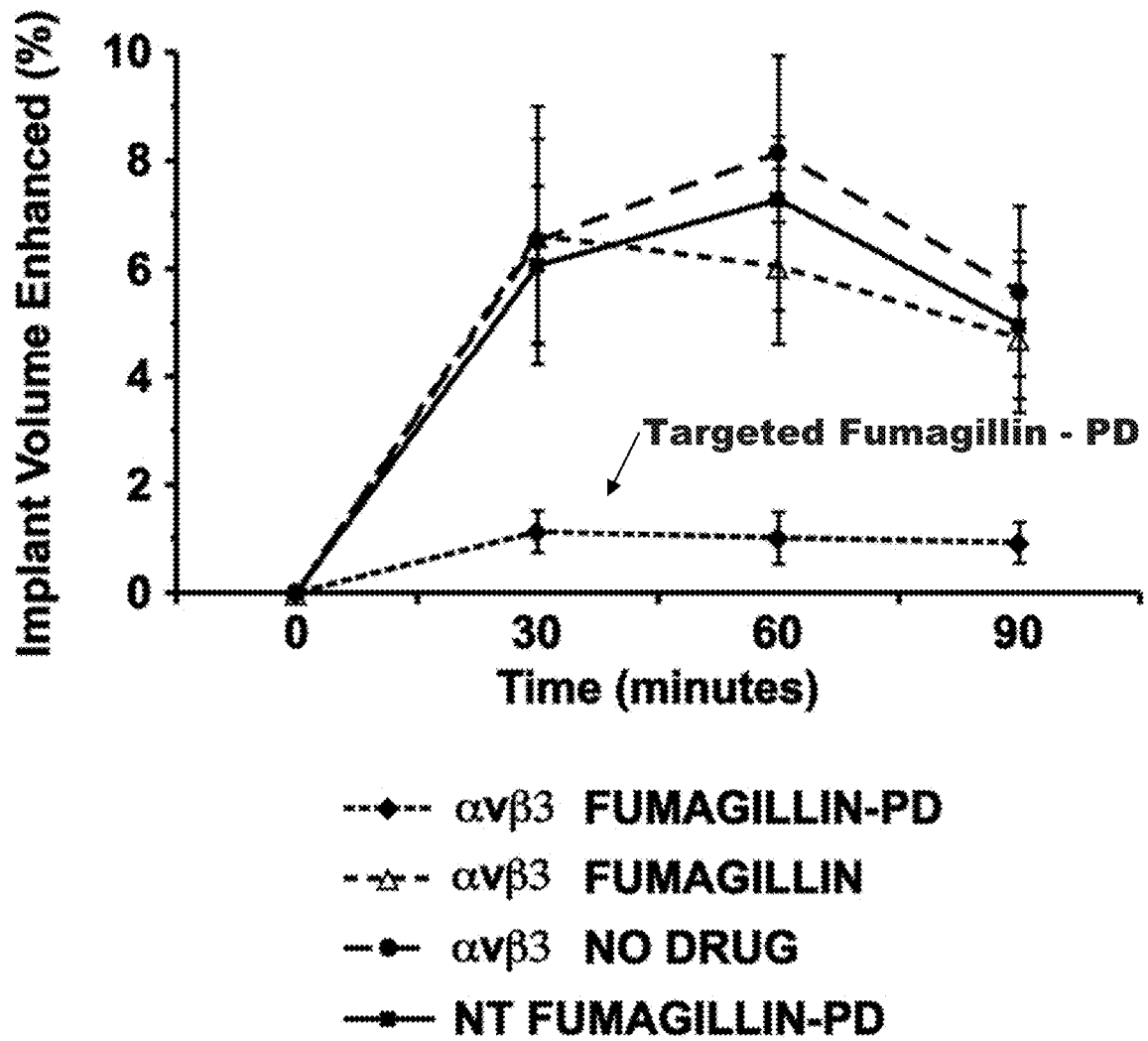
FIG. 20 depicts a graph showing that administration of a fumagillin prodrug targeted with $\alpha v\beta 3$ reduces implant volume enhancement.

As shown in FIG. 19, fumagillin dissolved in a lipid membrane rapidly releases in vivo, making it practically ineffective in vivo. FIG. 20 shows, however, the in vivo effectiveness of a fumagillin prodrug administered in a nanoparticle of the invention. In particular, the figure shows the in vivo MR signal enhancement post treatment with targeted fumagillin nanoparticles (a-b) and control (no drug, c-d); Reduced Matrigel implant volume (%) in rats treated with αvβ3-integrin-targeted nanoparticles with 2.28 mole % fumagillin-PD vs. αvβ3-integrin-targeted nanoparticles with 2.28% fumagillin, αvβ3-integrin-targeted nanoparticles without drug, nontargeted nanoparticles with 2.28 mole % fumagillin-PD.

Figure 21A:
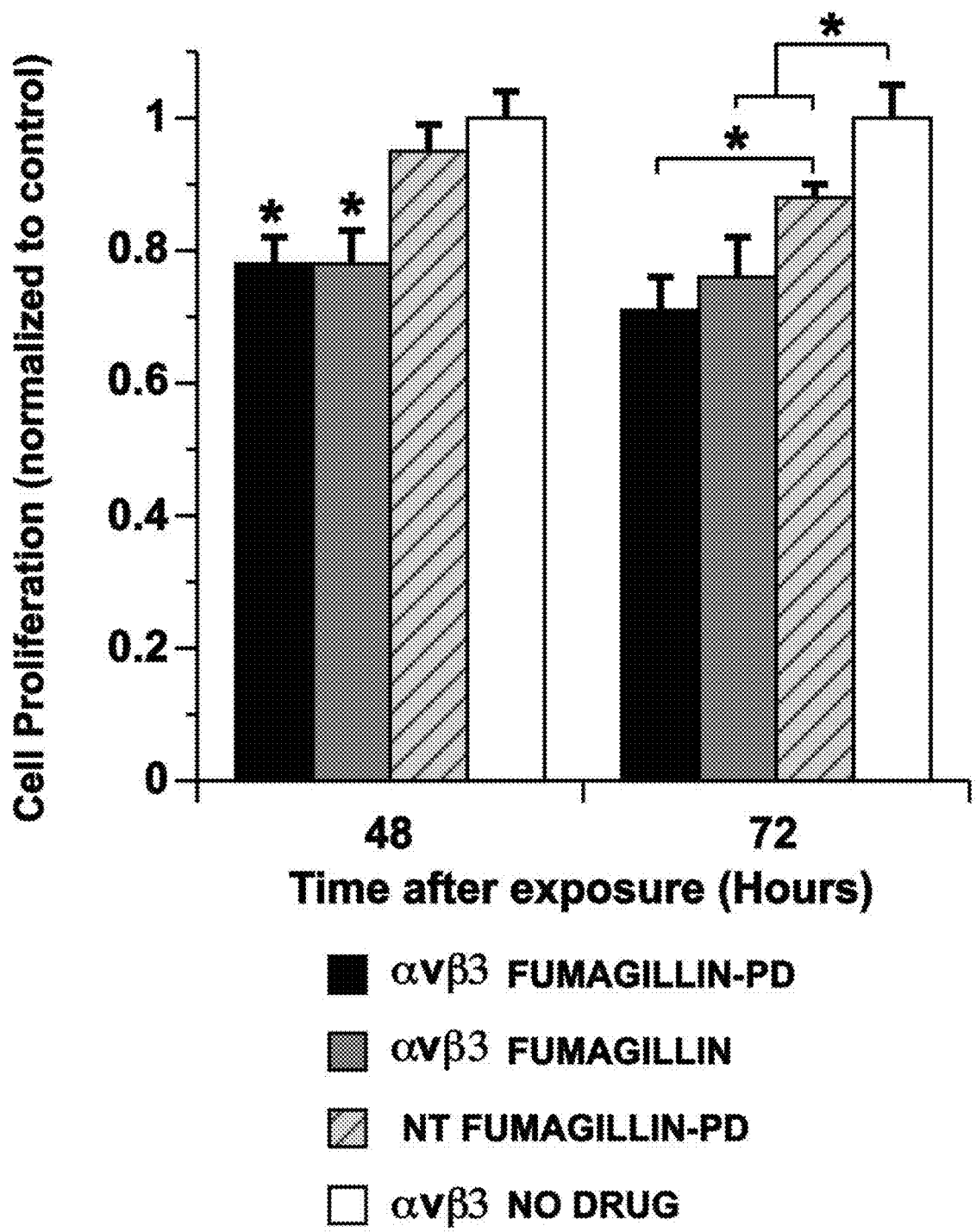
FIG. 21A-B depicts two graphs illustrating that an $\alpha v\beta 3$ targeted fumagillin prodrug reduces cellular proliferation. In (A) cellular proliferation is measured by a CyQuant Assay, and in (B) cellular metabolic activity is measured by an Alamar blue assay in HUVEC cells.
Figure 21B:
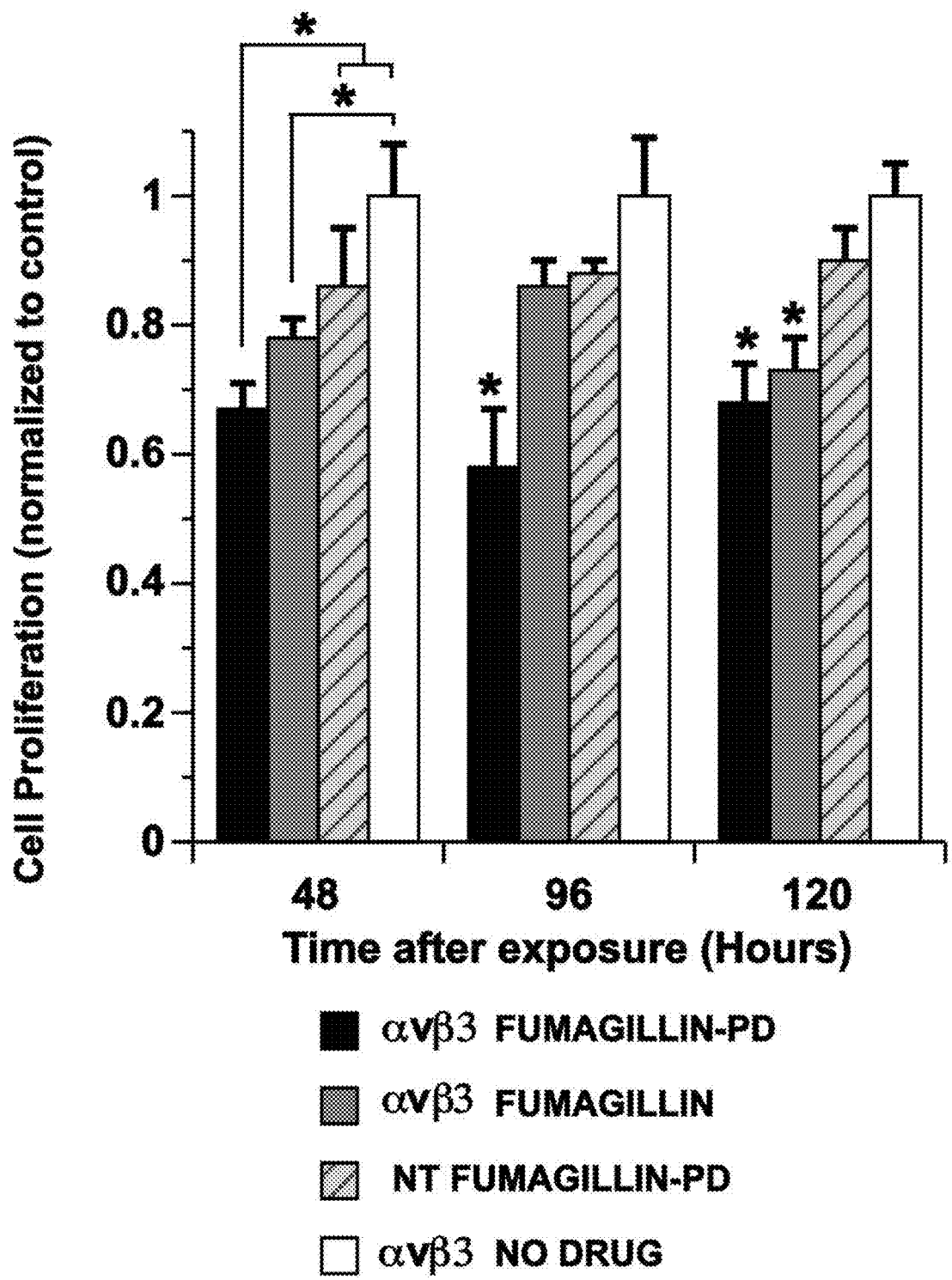

FIG. 21 shows the effect of the fumagillin prodrug in an in vitro cell proliferation assay. The left panel shows the effects of fumagillin prodrug incorporated nanoparticles and control nanoparticles (targeted no drug, non targeted and targeted fumagillin) on human umbilical vein endothelial cells (HUVEC) for cell proliferation by CyQuant NF assay and the right panel shows cell metabolic activity by Alamar Blue assay.

Example 14: Docetaxel Prodrug

Figure 18A:
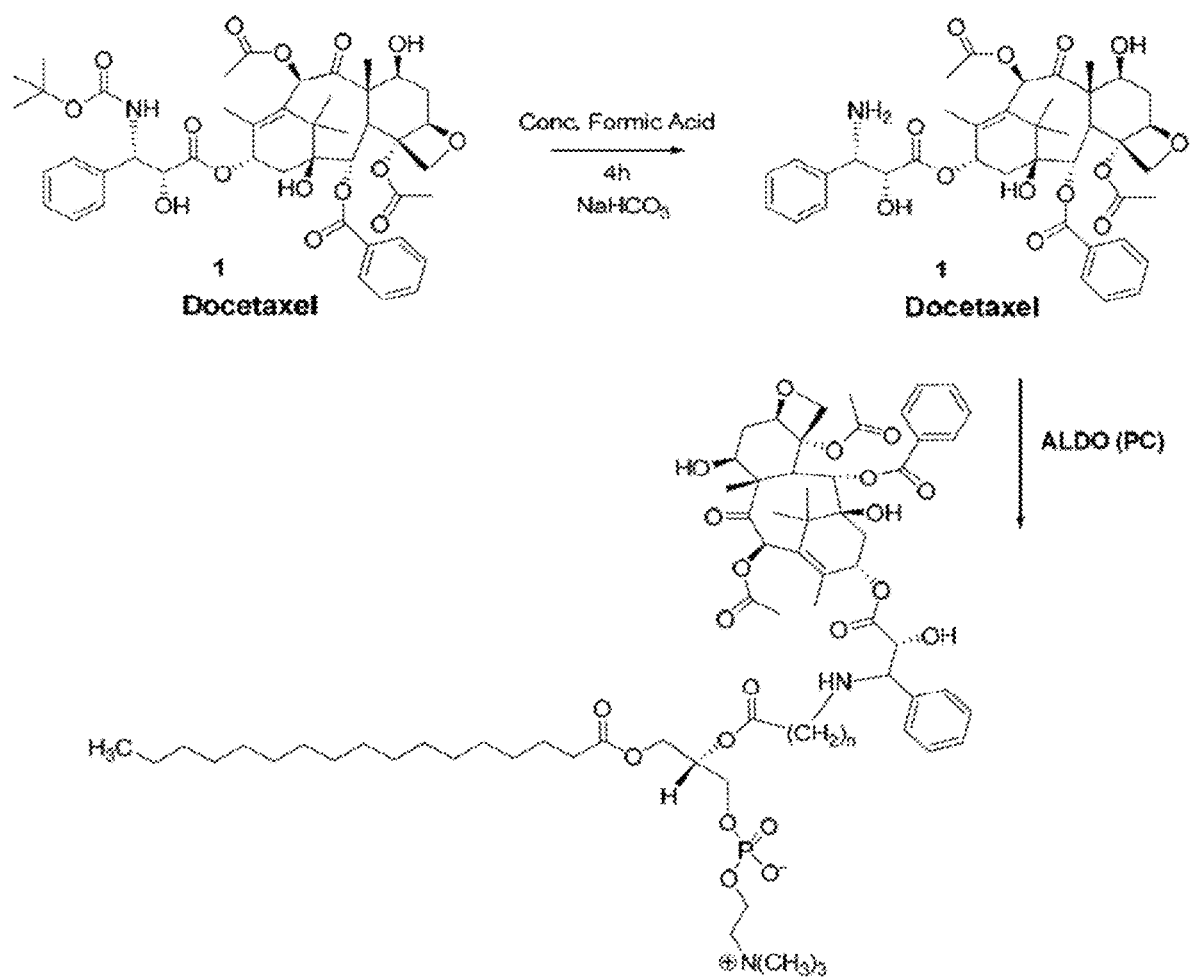
FIG. 18A-B depicts two synthesis schemes, specifically, the synthesis scheme for a docetaxel prodrug (A) and an alternative variant (B).
Figure 18B:
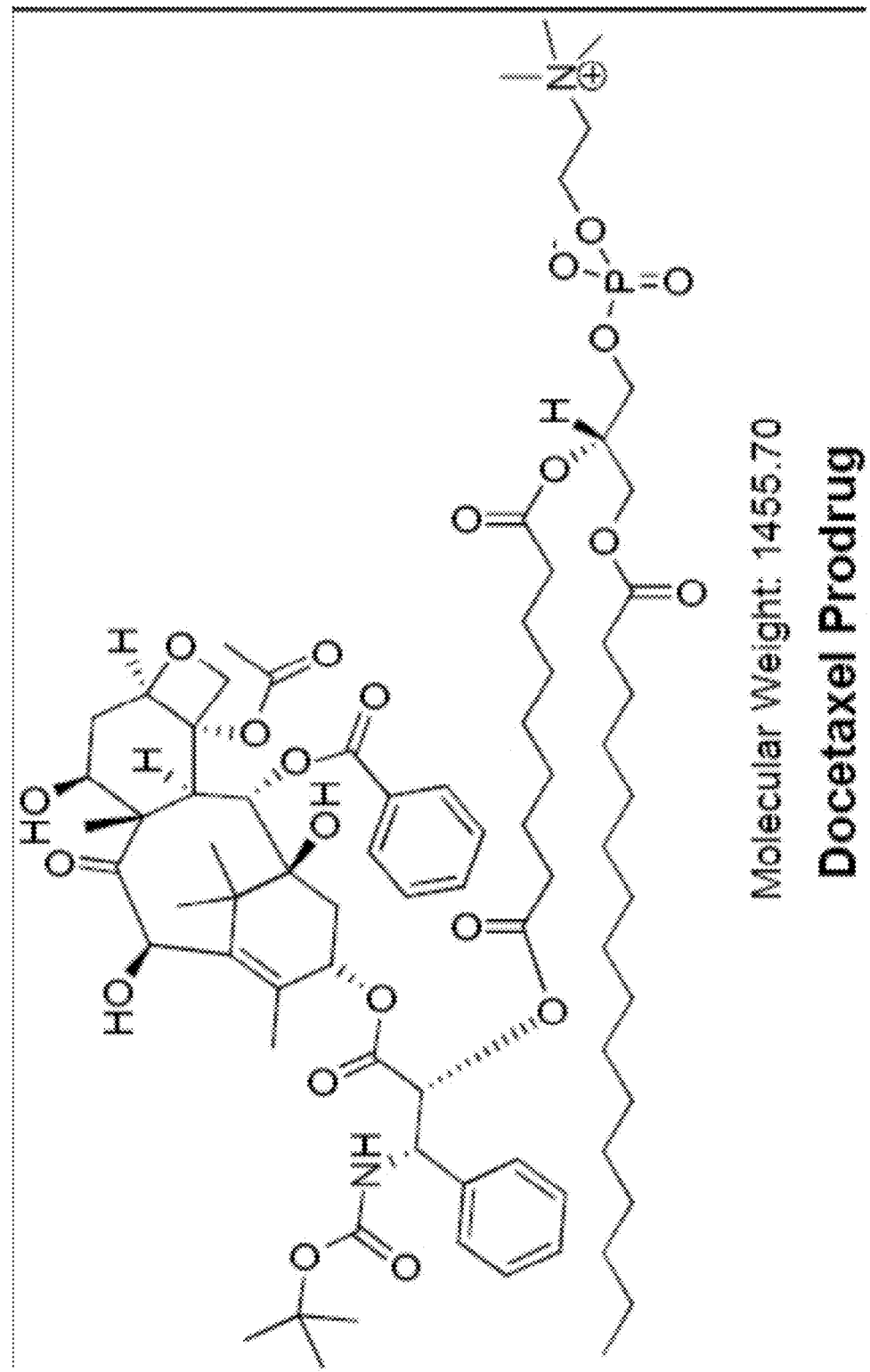
Figure 22:
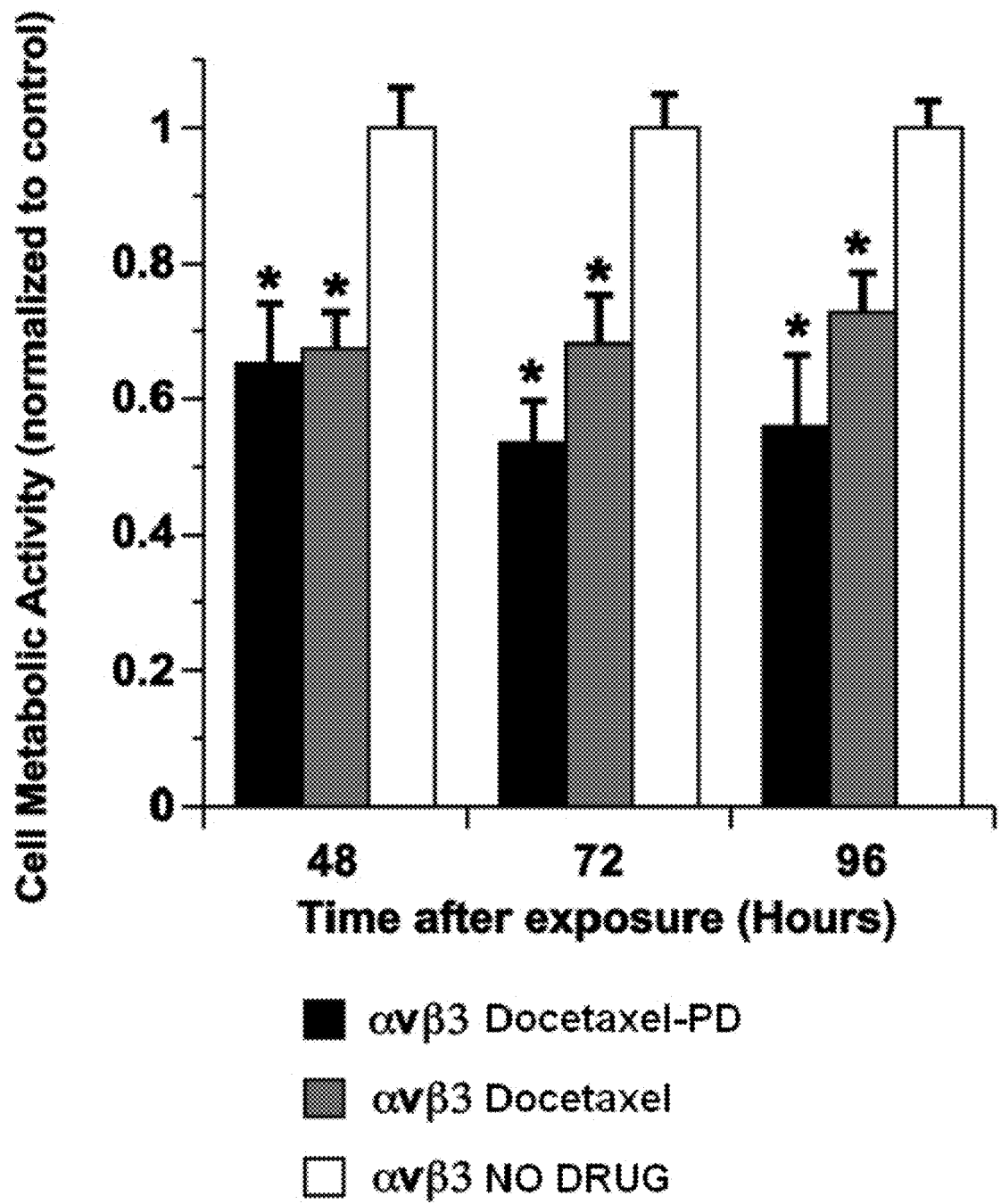
FIG. 22 depicts a graph illustrating the results of an alamar blue assay with a docetaxel prodrug. Seven thousand 2F2B cells/well were exposed to an $\alpha v\beta 3$ targeted particle comprising either no drug (control), docetaxel, or docetaxel prodrug.
Figure 23A:
FIG. 23A-C depicts micrographs and a graph demonstrating the effect of a docetaxel prodrug on tumor growth. (A) The four panels illustrate micrographs of tissue at baseline and at 3 hr postinjection exposed to either an $\alpha v\beta 3$ targeted particle comprising a docetaxel prodrug or an $\alpha v\beta 3$ targeted particle without docetaxel. (B) Tumor volume is decreased with the administration of a docetaxel prodrug. (C) Illustration of tumor volume with an $\alpha v\beta 3$ targeted particle comprising a docetaxel prodrug (left panel) or an $\alpha v\beta 3$ targeted particle without docetaxel (right panel).
Figure 23B:
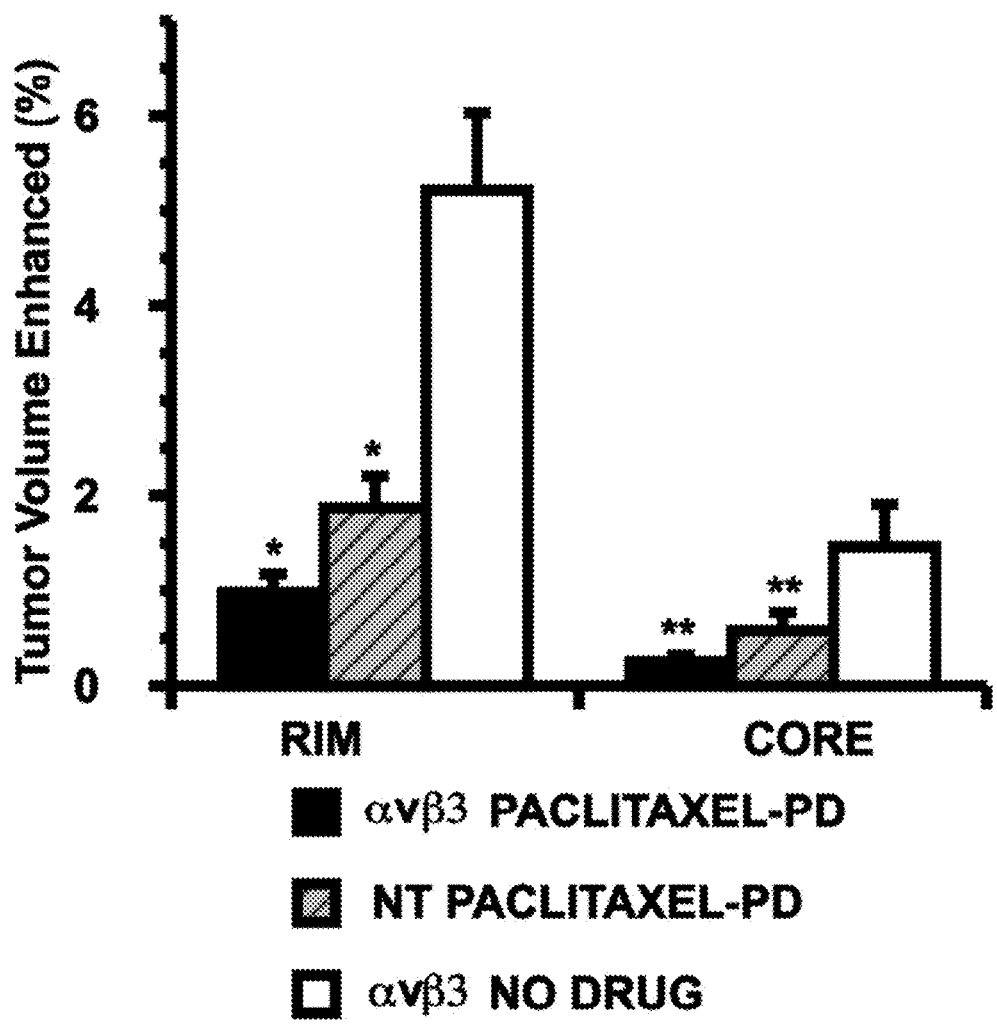
Figure 23C:
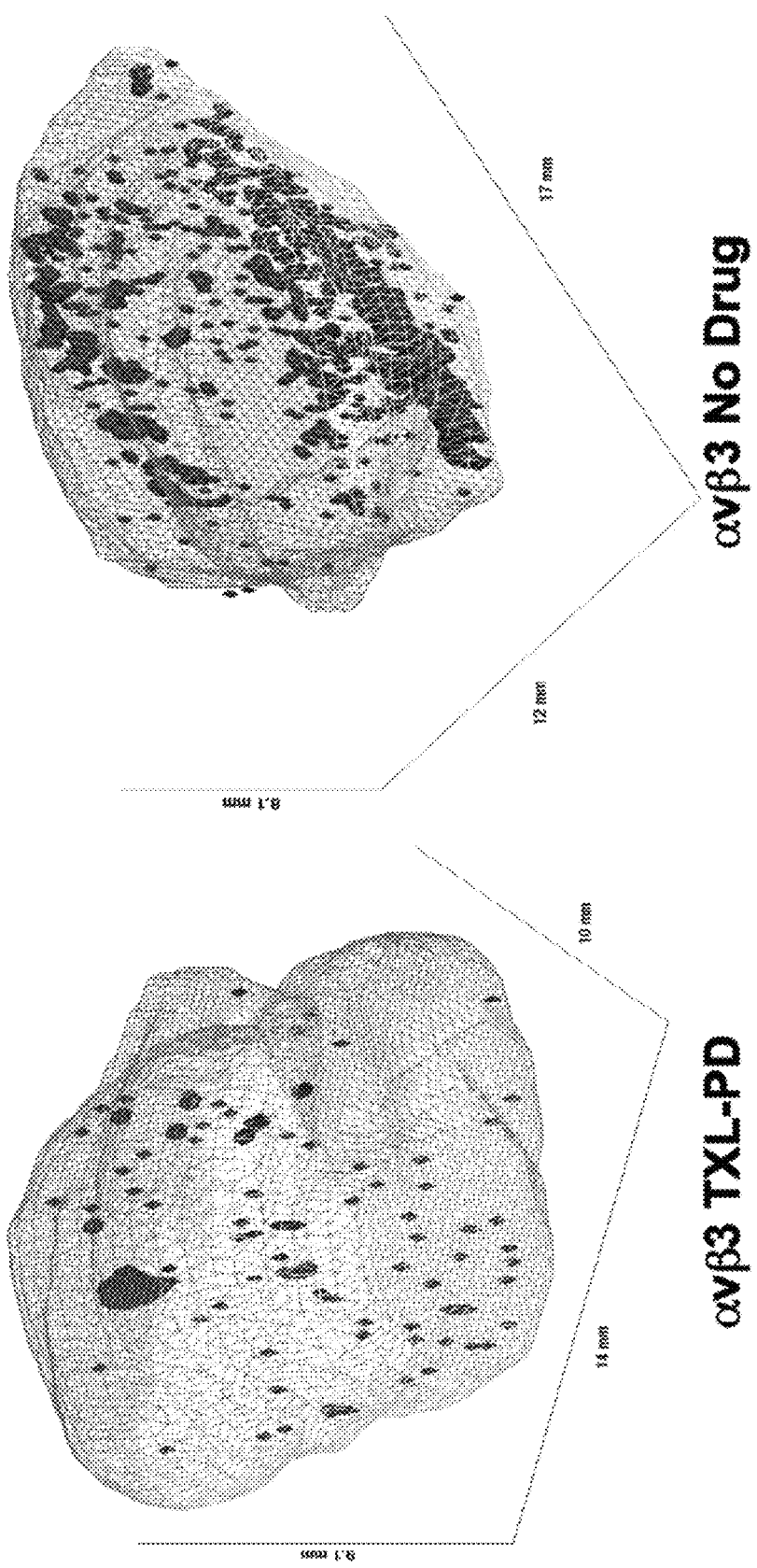
Figure 24A:
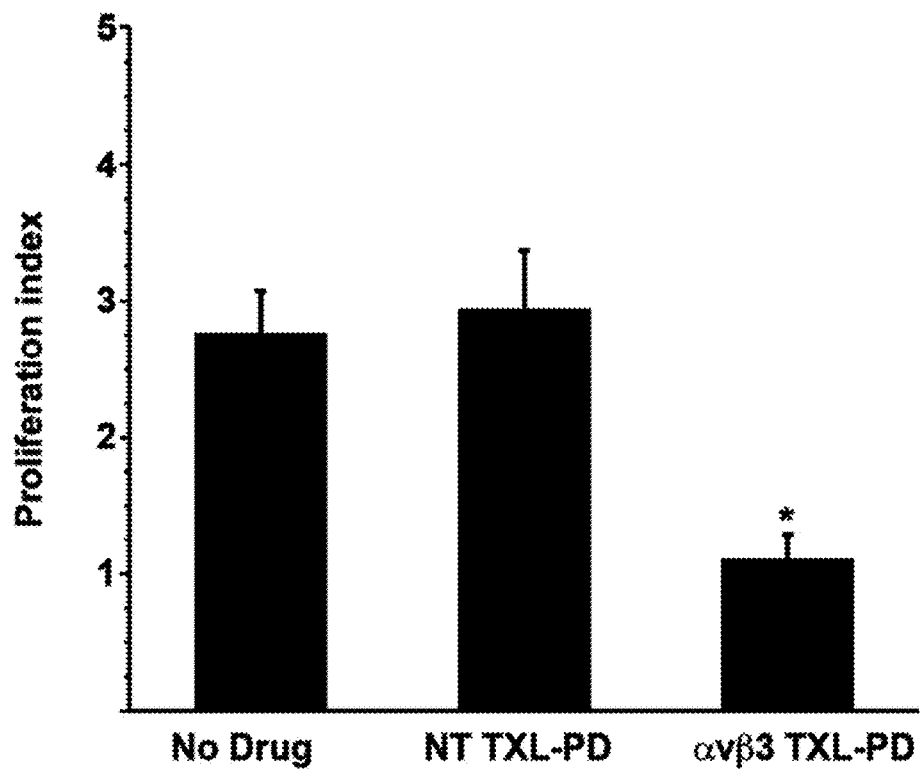
FIG. 24A-B depicts the effect of a docetaxel prodrug on the proliferation index. (A) Particles targeted with $\alpha v\beta 3$ and comprising a docetaxel prodrug reduce the proliferation index of tumor cells. (B) Micrographs demonstrate the reduced proliferation after exposure to an $\alpha v\beta 3$ targeted particle comprising docetaxel. Proliferation index equals the PCNA positive area divided by the methyl green nuclear positive only area.
Figure 24B:
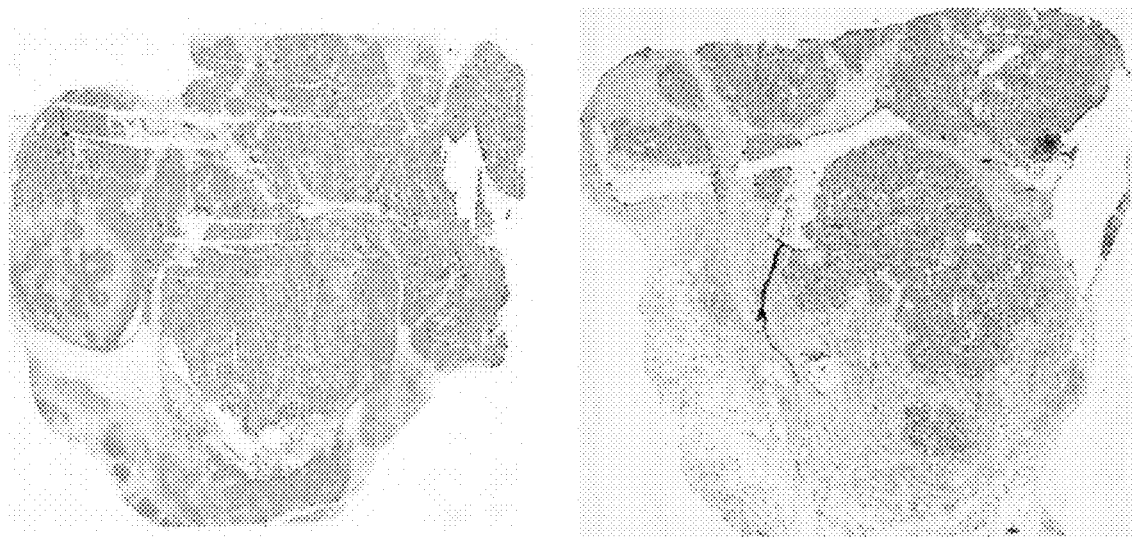
Figure 25A:
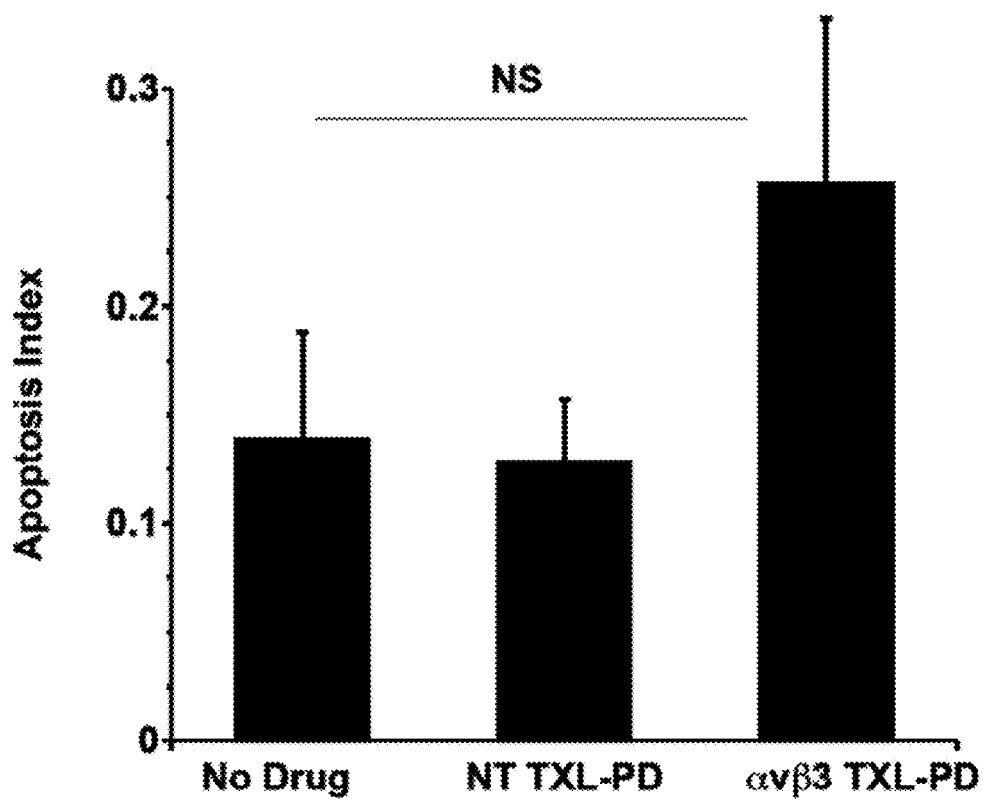
FIG. 25A-B depicts the effect of a docetaxel prodrug on the apoptotic index. (A) Particles targeted with $\alpha v\beta 3$ and comprising a docetaxel prodrug reduce the apoptosis index of tumor cells. (B) Micrographs demonstrate the reduced apoptosis after exposure to an $\alpha v\beta 3$ targeted particle comprising docetaxel. Apoptosis index equals the TUNEL positive area divided by the methyl green nuclear positive only area.
Figure 25B:
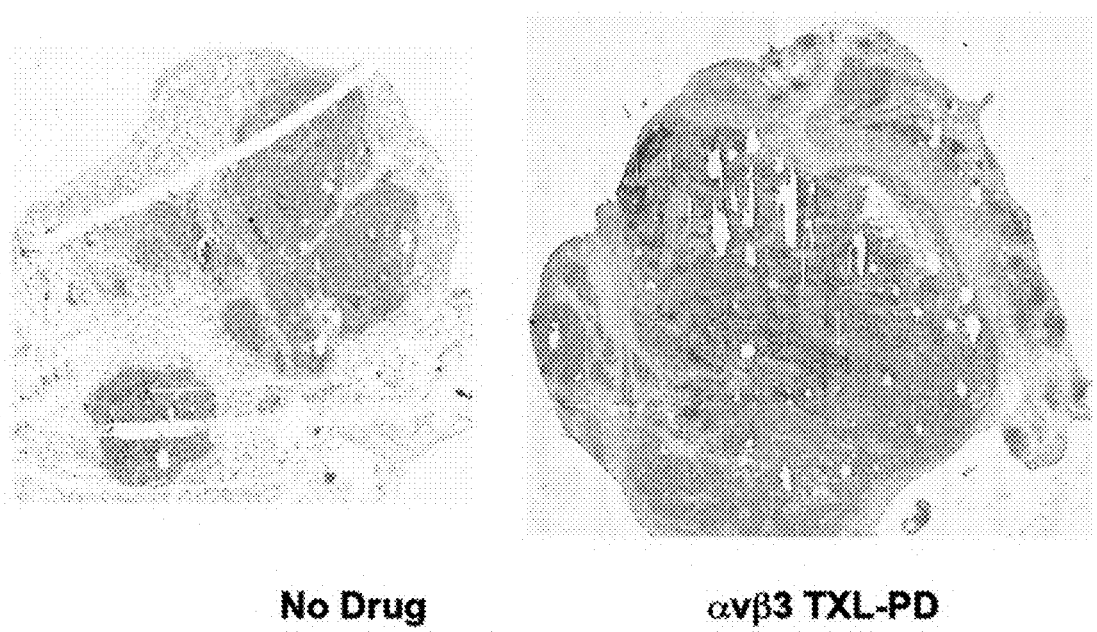
Figure 26A:
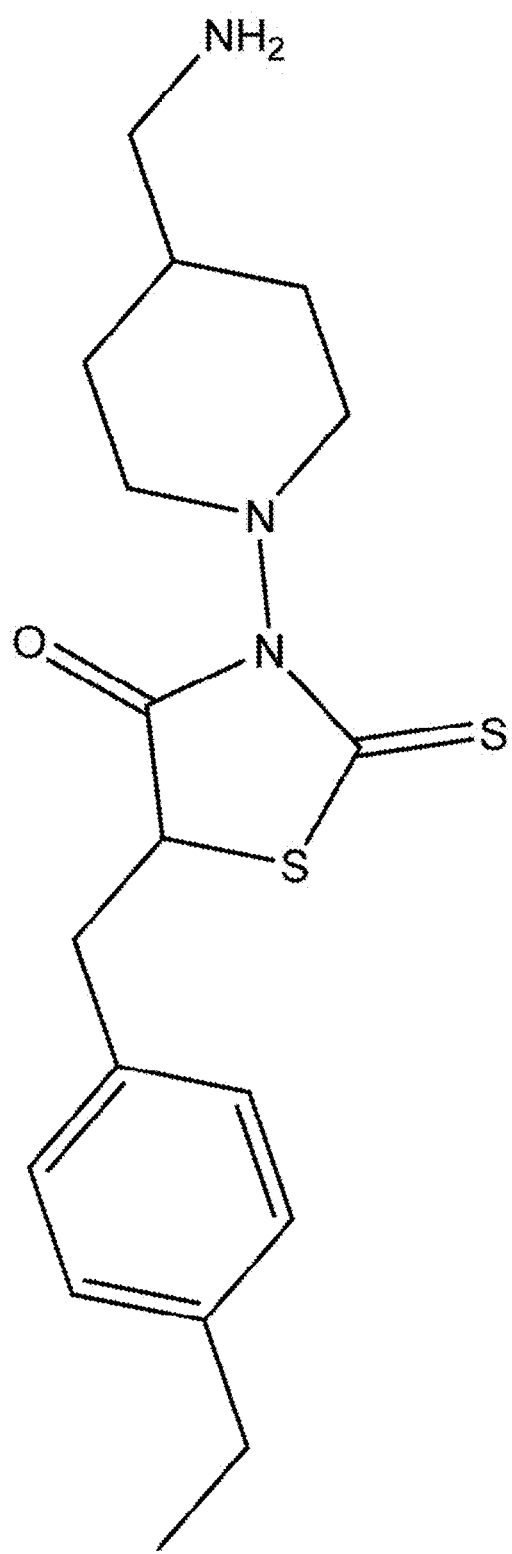
FIG. 26A-B depicts (A) the structure of the myc drug, and (B) graphs illustrating the effect of myc drug on the proliferation of Multiple Myeloma cell lines i. H-929 ii. LP-1 iii. KMS-11 iv. UTMC-2 incubated with different concentrations of the myc-drug compared to the control containing corresponding volumes of DMSO using Trypan Blue Exclusion.
Figure 26B:
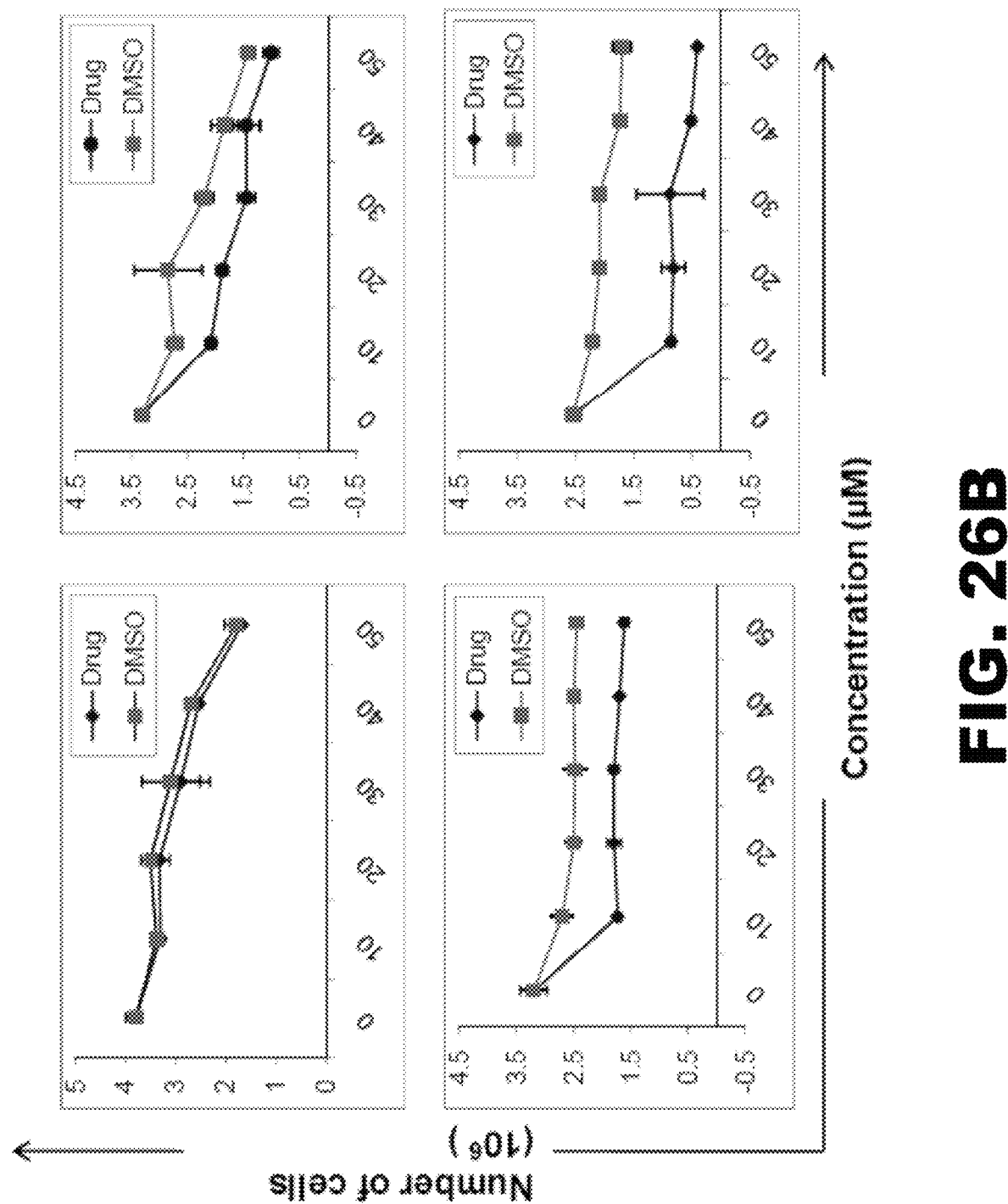

The docetaxel prodrug, synthesized as illustrated in FIG. 18A or B was administered to 2F2B cells in an alamar blue assay to measure metabolic activity. FIG. 22 shows a comparison between an αvβ3 targeted particle without docetaxel, an αvβ3 targeted particle with docetaxel, and an αvβ3 targeted particle with a docetaxel prodrug. As the assay progressed, the particle comprising the prodrug demonstrated a sustained suppression of cell metabolic activity, as compared to the targeted control without docetaxel.

Example 15. Synthesis of Photodynamic Therapy (PDT) Prodrugs

In a typical procedure zinc chelated porphyrin based PDT prodrug will be synthesized in straight forward manner. Amine terminated Zinc-porphyrin PDT prodrug is then subjected to reductive amination with ALDO PC in presence of $NaBH_4$ and catalytic amount of trifluoroacetic acid.

Example 16: Polysorbate Micelles

The present application encompasses the design, synthesis, physico-chemical characterization and use of novel nano-particulate systems for theranostic application and gene delivery system. Multifunctional nanoparticles play a very significant role in cancer drug delivery. The potential for nanoparticles in cancer drug delivery is infinite with novel new applications constantly being explored. Cancer has a physiological barrier like vascular endothelial pores, heterogeneous blood supply, heterogeneous architecture etc. For a therapy to be successful, it is very important to overcome these physiological barriers. For detection and treatment of cancer using targeted molecular imaging and drug delivery, nanoparticulate agents are the latest achievements in the medical field and form the basis of nanomedicine research. Various nanodevices has been explored inlcuding Nanopores, Nanotubes, Quantum Dots (QDs), Nanoshells, Dendrimers and shell crosslinked nanoparticles, PFC nanoparticles, biodegradable hydrogels etc.

Nanoscale devices are 100 times smaller than human cells but are similar in size to large biomolecules such as enzymes and receptors. In terms of the size and shape, nanoparticles smaller than 50 nm can easily enter most cells and those smaller than 20 nm can leave the blood vessels as they circulate through the body. Nanoparticles are designed as vectors to carry high payload of contrast agents for efficient detection in vivo and also are suitable to serve as customized, targeted drug delivery vehicles to carry large doses of chemotherapeutic agents or therapeutic genes into malignant cells while sparing healthy cells. In this approach, nanoparticles greatly reduce or eliminate the often unacceptable side effects that accompany many current cancer therapies. The type of nanoparticles is also very important and can be categorized into two main classes—inorganic and organic. Liposomes, dendrimers, carbon nanotubes, emulsions, and other polymeric nanoparticles are examples of widely studied group of organic particles. Most inorganic nanoparticles share the same basic structure of a central core that defines the fluorescence, optical, magnetic, and electronic properties of the particle, with a protective organic coating on the surface. This outside layer protects the core from degradation in a physiologically aggressive environment and can form electrostatic or covalent bonds, or both, with positively charged agents and biomolecules that have basic functional groups such as amines and thiols. In terms of the sizes, inorganic nanoparticles can be produced in a very small sizes ranging from 2-50 nm (Gold to iron oxide particles), however it is challenging to achieve such a small size range with organic precursors. Bigger nanoparticles in cancer are can make it difficult for them to evade organs such as the liver, spleen, and lungs, which are constantly clearing foreign materials from the body. In addition, they must be able to take advantage of subtle differences in cells to distinguish between normal and cancerous tissues. Indeed, it is only recently that researchers have begun to successfully engineer nanoparticles that can effectively evade the immune system and actively target tumors.

So, despite the recent advances in developing nanoparticles for targeted therapeutic imaging, there still exists a long standing need in the art for extravascular particles (<20 nm) water soluble, stable systems. Requisite features include biocompatibility, easily bio-metabolizable, internal sequestration of therapeutic agents, with adjustable release characteristics and tolerance to hostile in vivo environments. Based on these requirements we developed ultra small "soft" nanocelle nanoparticles for theranostic application. The nanoparticles are made specific to targeted cells or tissues by conjugating to a ligand (integrins $\alpha v\beta 3$, $\alpha 5\beta\square$, ICAM-1, VCAM-1, VLA-4 etc.) specific for the target cells or tissues. The nanoparticles may further include biologically active agents, prodrugs (fumagillin, myc-max inhibitor, camptothecin, cis platin, steroids, methotrexate, paclitaxel/docetaxel etc.) radionuclide etc. for their application in imaging and therapy. Particles are incorporated with contrast agents for MR, CT, optical, photoacoustic, PET, SPECT and US.

Preparation of Nanocelle Nanoparticles

We have prepared water soluble nanocelle nanoparticle with a nominal hydrodynamic diameter between 16-20 nm. The core of these particles is composed of biologically relevant surfactants (i.e. Tween80, span 80, sorbitan sesquioleate, sorbitan monolaurate) with phospholipids coating around it. The particles are thoroughly characterized by physico-chemical ways.

Figure 30:
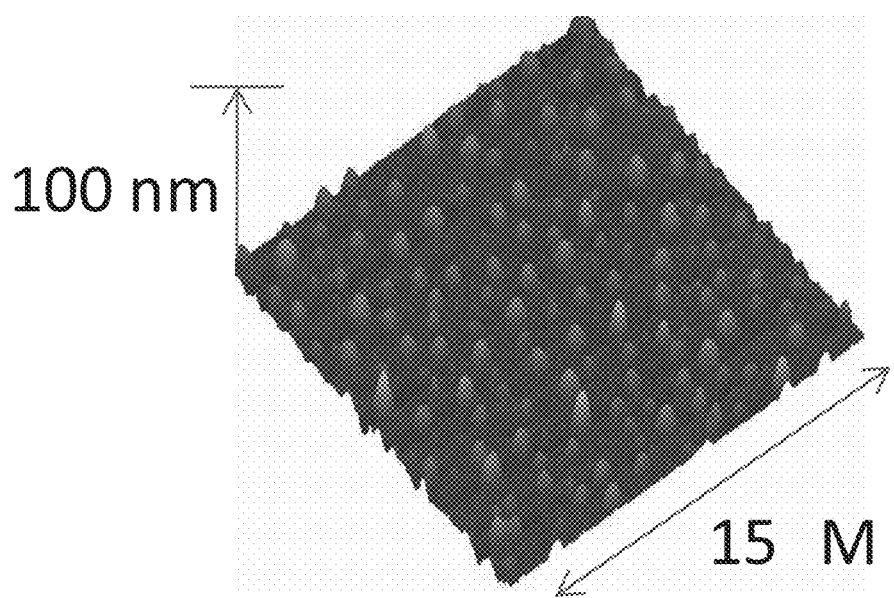
FIG. 30 depicts an illustration of a tapping mode AFM image of aqueous dispersion of nanocelle drop deposited over a glass surface.
Figure 32A:
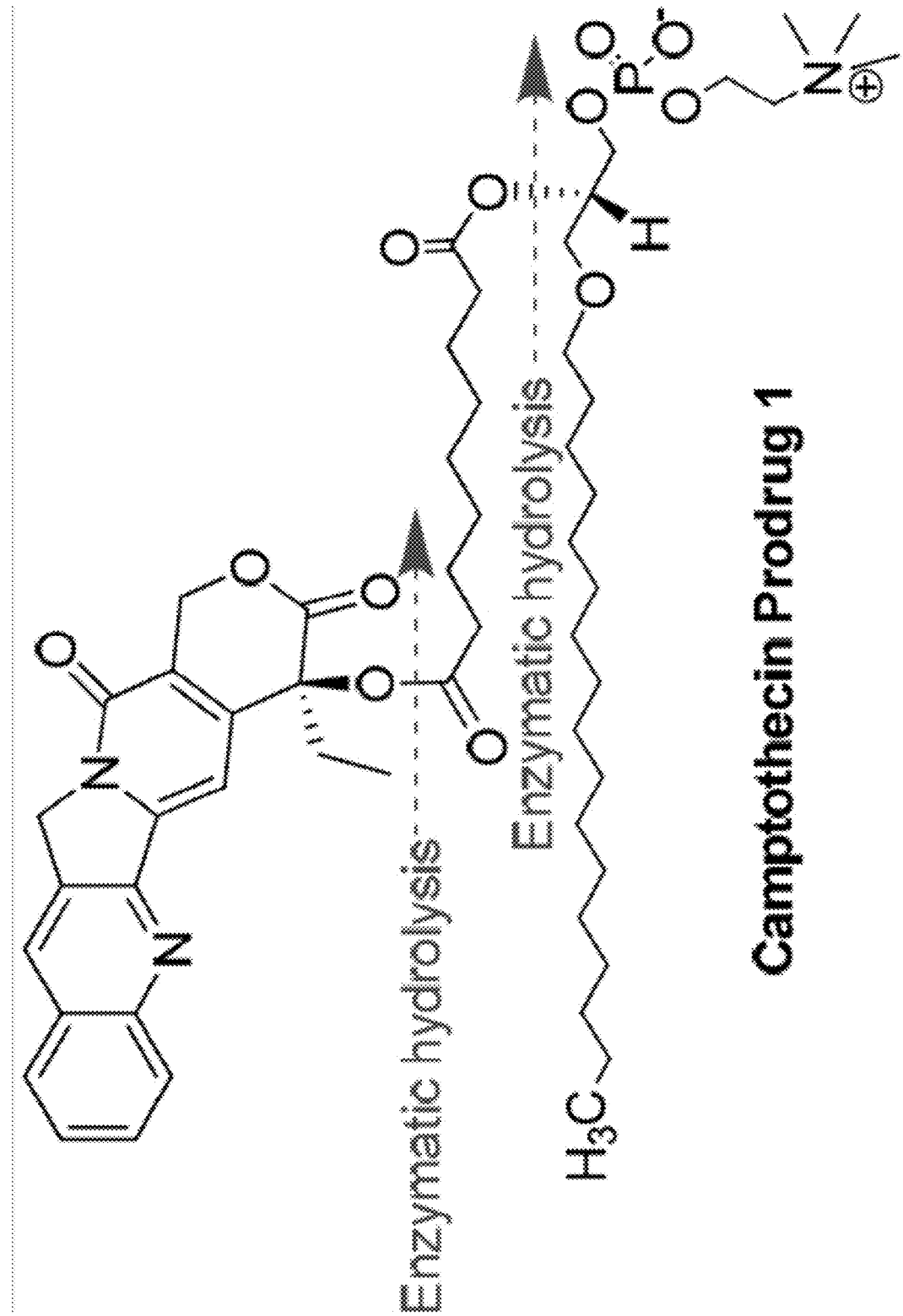
Figure 33A:
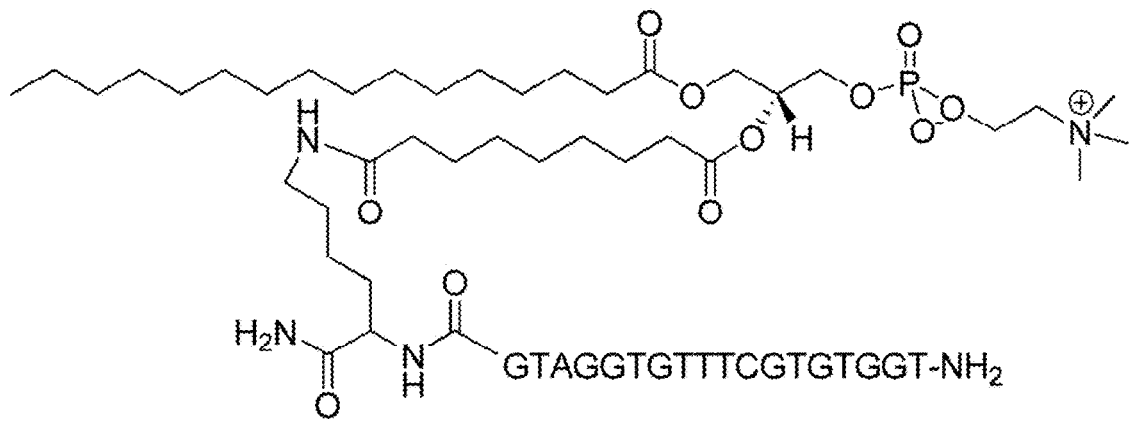
FIG. 33A-B depicts two prodrugs comprising PNA.
Figure 33B:
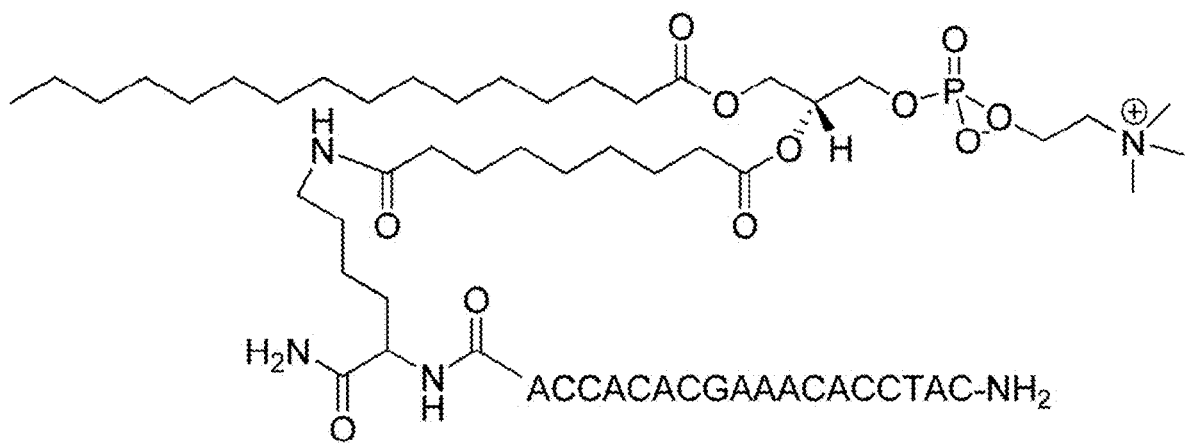

Typical Procedure for Preparation of avb3-Targeted Myc-Max Inhibitor Loaded Nanocelle Particle:

In a typical experimental procedure, the surfactant co-mixture included high purity egg yolk phosphatidylcholine (99 mole %, 395.5 mg), $\alpha_v\beta_3$-peptidomimetic antagonist conjugated to PEG2000-phosphatidylethanolamine (0.1 mole %, Kereos, Inc, St. Louis, Mo., USA). (1 mole %, 6.0 mg) and 2 mole % of myc-max prodrug. The surfactant co-mixture was dissolved in anhydrous chloroform, evaporated under reduced pressure to form a thin film, dried in a 50° C. vacuum oven overnight, and dispersed into water (5 mL) by probe sonication. This suspension was combined with the polysorbate mixture (20% v/v, 4 ml), distilled, de-ionized water (77.3% w/v, total 15.23 ml) and glycerin (1.7%, w/v, 0.37 ml). The mixture was continuously processed thereafter at 20,000 PSI for 4 minutes with an S110 Microfluidics emulsifier (Microfluidics) 0° C. The nanocelle particles were dialyzed against nanopure (0.2 µm) water using a 20,000 Da MWCO cellulose membrane for prolonged period of time and then passed through a 0.45 µm Acrodisc Syringe filter. The nanoparticles were stored under argon atmosphere typically at 4° C. in order to prevent any bacterial growth. Hydrated state hydrodynamic diameters (16±4 nm) of the particles are measured by Brookhaven dynamic light scattering experiments operating the laser at 90°. The de-hydrated state diameter and particle height are measured using TEM (negatively stained with 1% uranyl acetate and dried over nickel surface) and AFM (FIG. 30) (tapping mode, drop deposited and dried over glass cover slips) respectively.

Prodrug Testing In Vitro: Cytotoxicity Assays

Figure 27A:
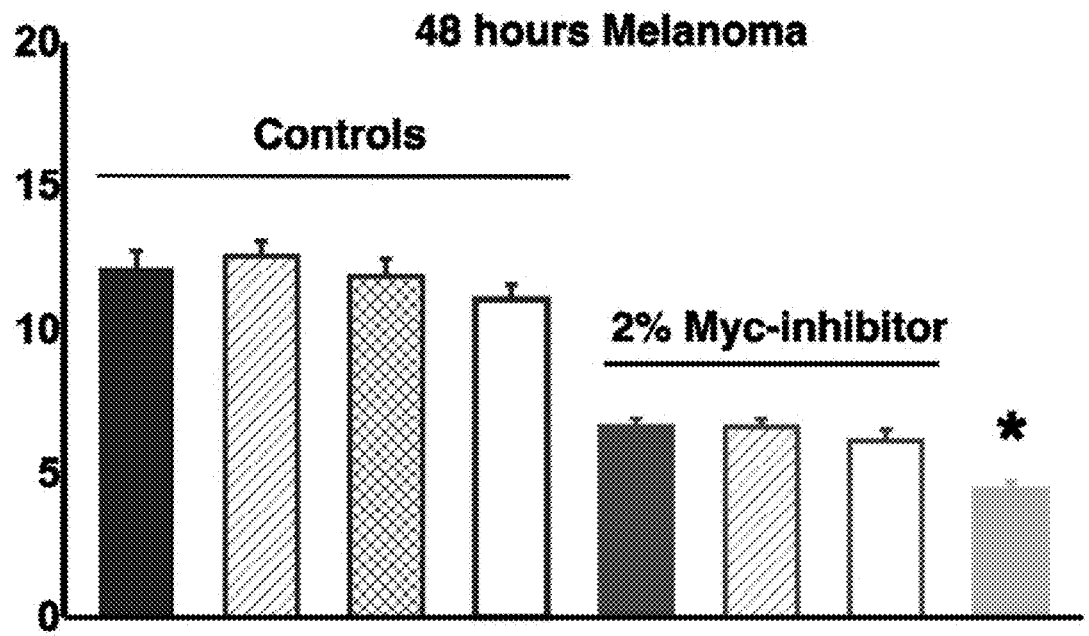
FIG. 27A-B depicts graphs illustrating that a myc-max antagonist prodrug inhibits melanoma proliferation in vitro at (A) 48 hrs and (B) 72 hrs. Tg: targeted; PFC: perfluorocarbon particles; tween: polysorbate micelles.
Figure 27B:
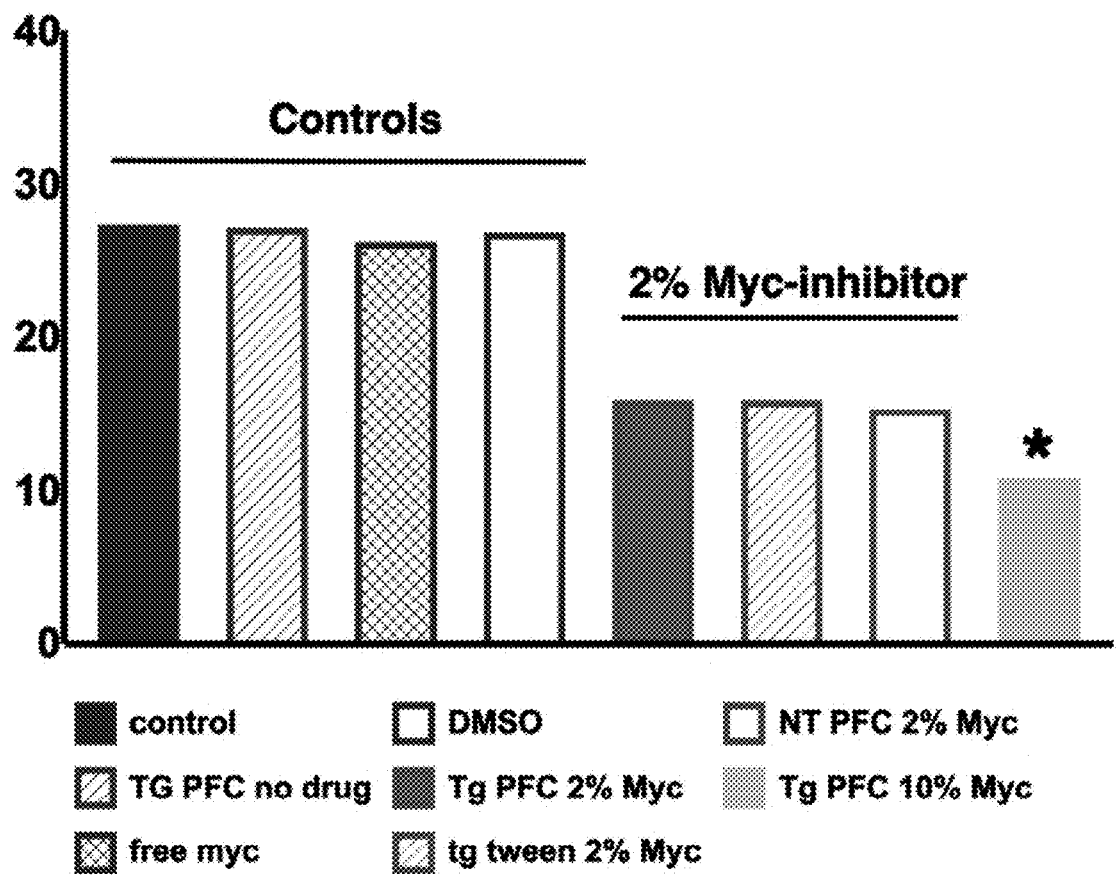

Human B16 melanoma cells were seeded on a 96 well plate (5000 cells/well). After 24 hours, cells were incubated with avb3-integrin targeted nanocelle myc prodrug (~0.5 uM myc-PD), free myc, targeted no drug, or nontargeted myc prodrug nanocelles for one hour (6 replicates per sample per plate). Wells were washed three times with PBS, and plates were returned to the incubator. From two to four days after drug exposure, Cell metabolic activity was measured using an Alamar Blue (Invitrogen). This assay is based on the reduction of nonfluorescent dye to fluorescent substrate in metabolically active cells. This reduction is typically attributed to different oxidoreductase enzyme systems that use NAD(P)H as the primary electron donor. This redox reaction was monitored using a fluorescence plate reader (Ex 570 nm, Em 587 nm) where the resulting signal is proportional to the number of viable cells present. Signal intensity from each sample was normalized to signal from the positive control ($\alpha v\beta 3$-integrin targeted no drug nanoparticles) (n=3-6 plates per time point) (FIG. 27).

Example 17: Prodrug Comprising PNA

PNAs and conjugates are synthesized on an automated peptide synthesizer on 2 µmol Fmo'c-PAL-PEG-PS according to the standard automated Fmoc PNA synthesis procedure utilizing commercial monomers (Panagene Inc., Korea). Following the final step of automated synthesis the resin is washed with dry DMF (2×3 mL) and dry $CH_2Cl_2$ (2×3 mL), followed by drying under a stream of $N_2$. The resin will then be shaken in a vial with trifluoroacetic acid (300 µL) and m-cresol (100 µL) at room temperature for 2 h to release and deprotect the PNA. The solution is filtered from the resin, and added into ice-cold $Et_2O$ (5 mL) and kept at 4° C. for 1 h. The resulting precipitate is collected by centrifugation and purified by reverse-phase HPLC. PNA-lysine conjugates are synthesized (2 µmol) on an automated peptide synthesizer using standard Fmoc chemistry. PNA-lysine conjugates in DMSO (0.19 µmol, determined spectrophotometrically) are added to a solution of PAzPC and allowed to stir for 30 min prior to the addition of 1-[3-(dimethylamino)propyl]-3-ethylcarbodiimide methiodide. The resulting solution was allowed to stir for 16 h and purified by reverse phase HPLC technique.

Example 18: Synthesis of Camptothecin Prodrug

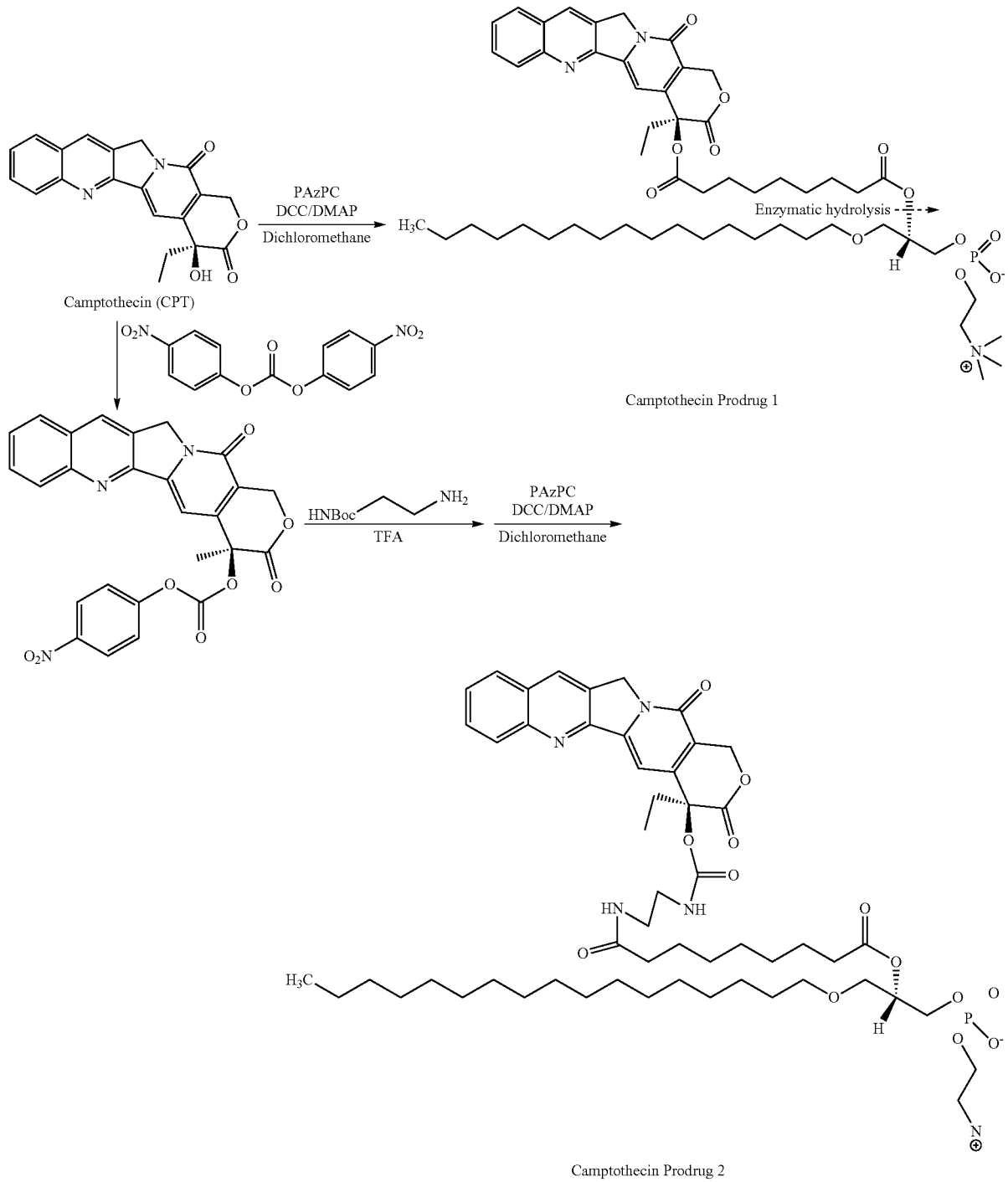

Diagram 7. Synthesis pathway for Campothecin prodrug 1 (top) and prodrugs 2. (bottom).

a.1) Synthesis of Camptothecin Prodrug 1

Camptothecin prodrug (1) will be produced by the direct coupling of the compound with PAzPC (fatty acid modified oxidized lipid16:0-9:0 COOH PC) in presence of DCC/DMAP mediated coupling protocol.

a.2) Synthesis of Camptothecin Prodrug 2

Camptothecin will be activated with bis(4-nitrophenyl) carbonate followed by reacting with monoboc-ethylend-imine to produce 6. In a typical experimental procedure, under a $N_2$ atmosphere, a mixture of camptothecin, bis(4-nitrophenyl) carbonate and DMAP in dry $CH_2Cl_2$ will be stirred for 7 h. The reaction mixture will be diluted with CH₂Cl₂ and washed with H₂O. The organic layer will be dried (Na₂SO₄) and concentrated. Flash chromatography (EtOAc-hexane) will be used to yield the activated fumagillol. Monoboc-protected ethylendiamine will then be coupled to prepare intermediate-6. The product will be recovered and immediately be subjected to DCC/DMAP mediated coupling with PAzPC. The chemical identity of both analogues will be confirmed by NMR and mass-spectrometric analyses.

Example 19: Methyl Prednisolone Prodrug

Methylprednisolone prodrug is produced by the direct coupling of the compound with PAzPC (fatty acid modified oxidized lipid16:0-9:0 COOH PC) in presence of DCC/DMAP mediated coupling protocol.

Example 20: Method of Coupling Ligands to the Nanoparticles

Coupling of the ligand to the nanoparticle may be achieved uniquely by following an inclusion compound protocol with β-cyclodextrin (β-CD) on the particle spontaneously interacting with adamantane on the peptide or small molecule ligand to form an inclusion complex. Briefly, cyclodextrin-PEG-DSPE derivative will be synthesized via mono-6-deoxy-6-amino-β-cyclodextrin. One of the seven primary hydroxyl groups of β-cyclodextrin will be tosylated using p-toluenesulfonyl chloride. Substitution of the tosyl group by azide and subsequent reduction with triphenylphosphine will yield mono-6-deoxy-6-amino-β-cyclodextrin. Carboxyl-activated PEG-DSPE will be conjugated to mono-6-deoxy-6-amino-β-cyclodextrin to produce cyclodextrin-PEG-DSPE. Adamantane-amine will be directly conjugated through a short spacer in the solid phase peptide synthesis to the carboxyl end of the peptide to produce adamantane-peptide/ligand. The simple room temperature mixing of adamantane-amine and β-cyclodextrin bearing nanoparticle will produce peptide coupled targeted nanoparticle.

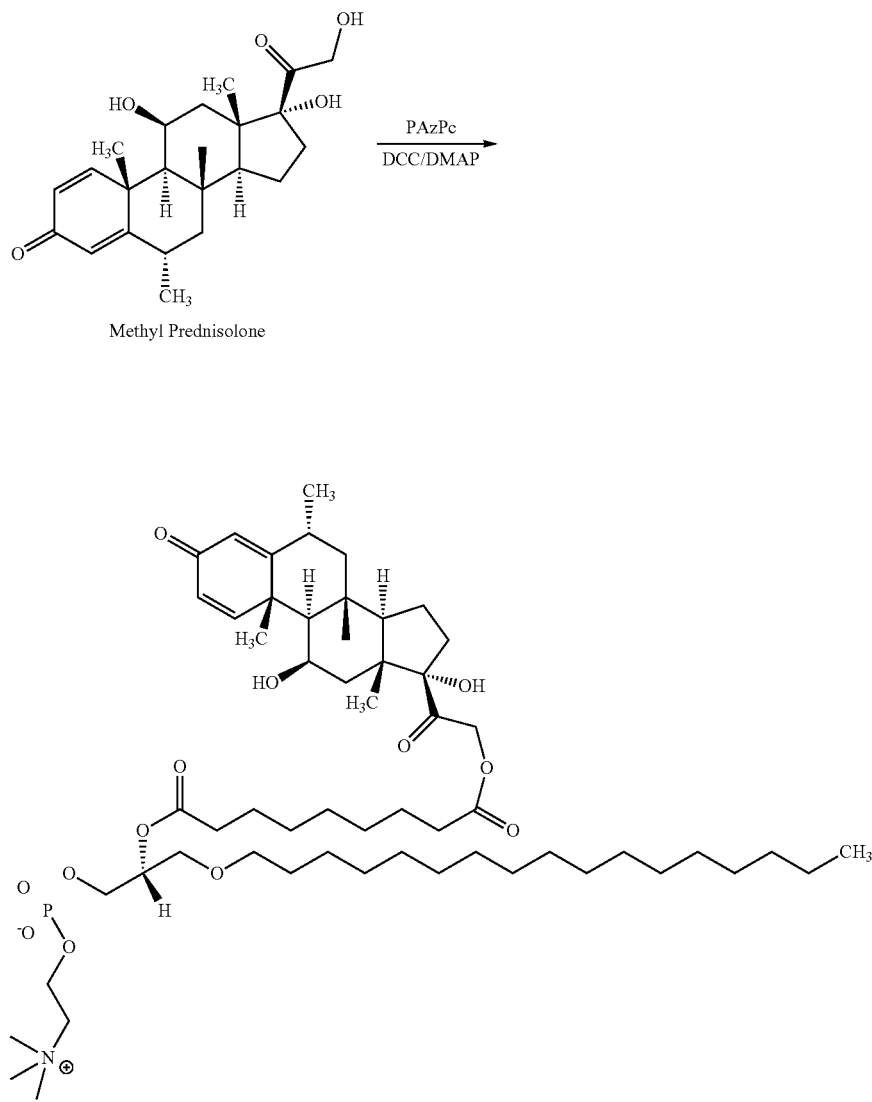

What is claimed is:

1. A composition for in vivo delivery of a compound to a target cell, the composition comprising a non-liposomal particle and at least one prodrug, wherein:
(a) the particle has an outer surface that is a membrane comprised of the at least one prodrug, about 100 mol % to about 60 mol % phospholipid, and a homing ligand, and an inner core comprising a surfactant;
(b) the particle has a hydrodynamic diameter that is about 10 to about 20 nm, as measured by dynamic light scattering;
(c) the prodrug comprises a compound of less than about 3000 da linked to an acyl moiety of a phosphoglyceride, wherein the compound may be released from the phosphoglyceride backbone via enzyme cleavage; and
(d) the particle can leave blood vessels while circulating through the body.

2. The composition of claim 1, wherein the surfactant is selected from the group consisting of polysorbate 80, sorbitan monooleate, sorbitan sesquioleate, and sorbitan monolaurate.

3. The composition of claim 1, wherein the outer surface of the particle is comprised of not more than 3 mol % of a prodrug.

4. The composition of claim 1, wherein the outer surface of the particle is comprised of about 0.1 mol % of a prodrug to about 9% of a prodrug.

5. The composition of claim 1, wherein the non-liposomal particle is a micelle.

6. The composition of claim 1, wherein less than about 10% of the outer surface of the particle is cross-linked.

7. The composition of claim 1, wherein the outer surface is not pegylated except for the homing ligand.

8. The composition of claim 1, wherein the homing ligand is selected from the group consisting of antibodies, antibody fragments, peptides, asialoglycoproteins, polysaccharides, nucleic acids, small molecules, and peptidomimetics.

9. The composition of claim 1, wherein the homing ligand is selected from the group consisting of integrins αvβ3, α5β1, ICAM-1, VCAM-1 and VLA-4.

10. The composition of claim 1, wherein the compound is linked to the sn-2 acyl moiety of the phosphoglyceride.

11. The composition of claim 10, wherein the acyl moiety of the prodrug is at least 4 carbon atoms in length from the glycerol backbone sn-2 ester bond.

12. The composition of claim 1, wherein the compound is docetaxel or paclitaxel.

13. The composition of claim 1, wherein the prodrug is a compound selected from the group consisting of

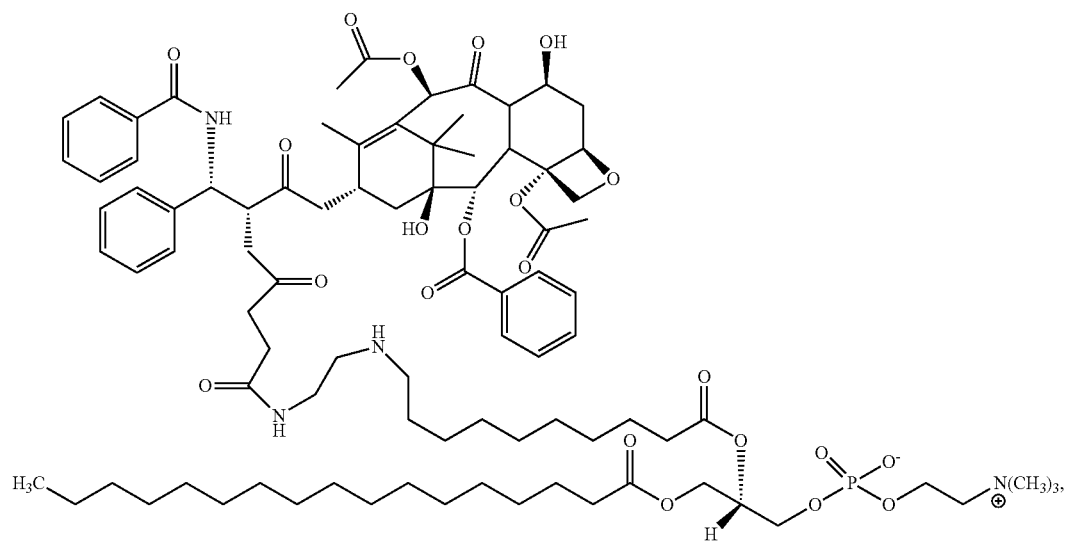
(compound II)
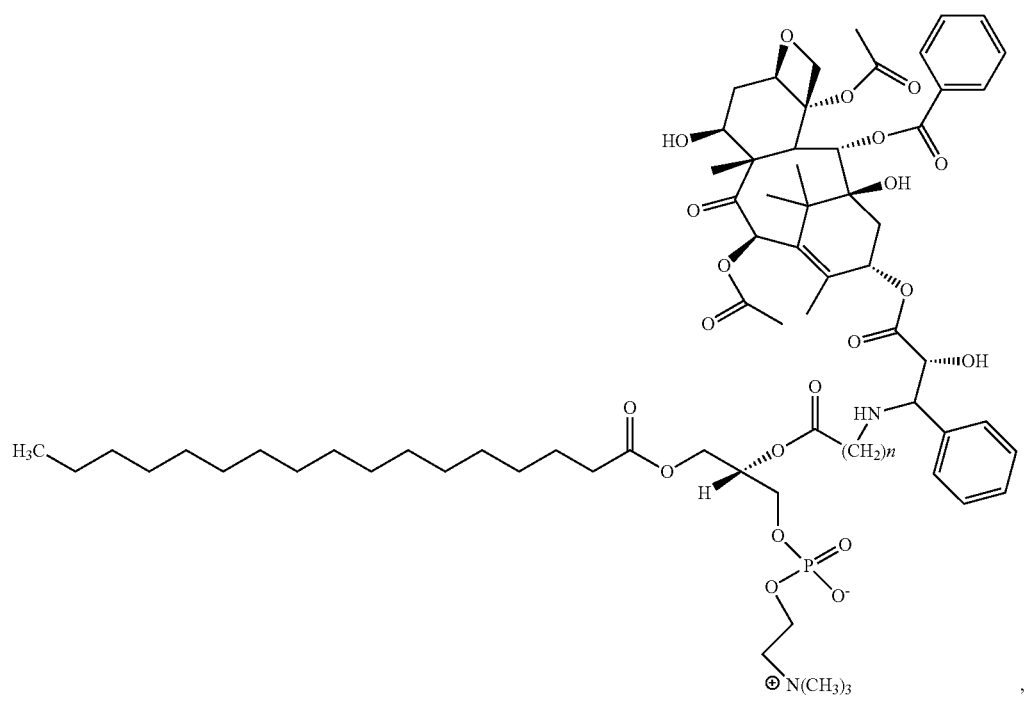
(compound XII)
, and

-continued (compound XIII)

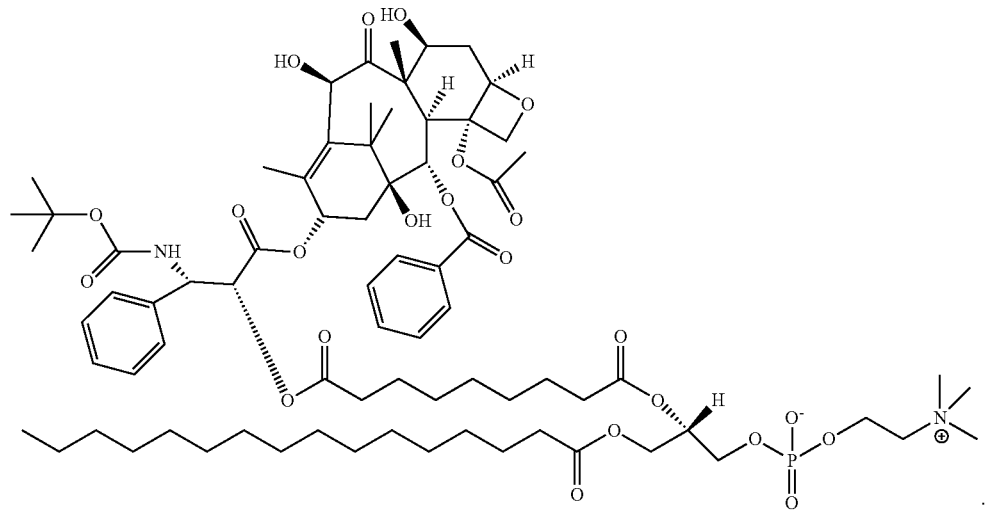

14. The composition of claim 1, wherein the compound is camptothecin.

15. The composition of claim 14, wherein the prodrug is (compound XV)

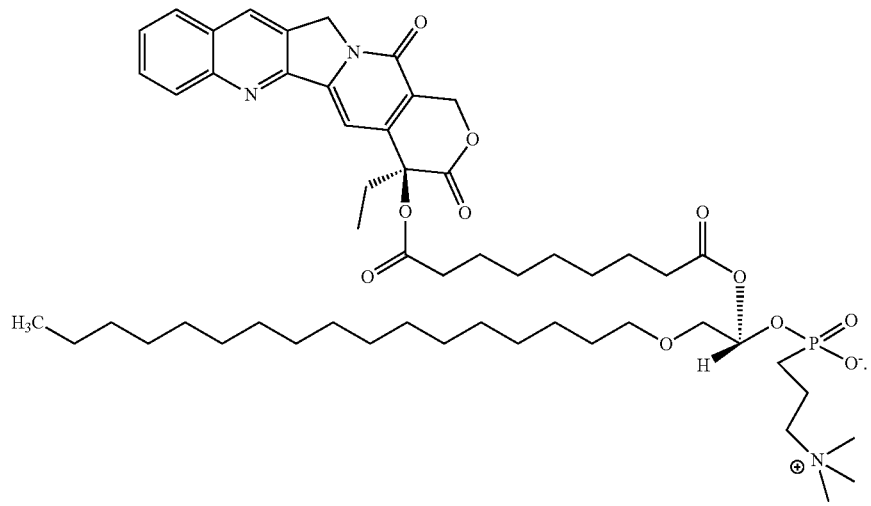

16. The composition of claim 1, wherein the phosphoglyceride of the prodrug comprises a phosphoglyceride selected from the group consisting of phosphatidyl choline, phosphatidyl ethanolamine, phosphatidyl inositol, and phosphatidyl serine.

17. A method for in vivo delivery of a compound to a target cell, the method comprising administering a composition of claim 1 to a subject.

18. The method of claim 17, wherein the composition is administered intravenously.

* * * * *

SEQUENCE LISTING

<160> NUMBER OF SEQ ID NOS: 2

<210> SEQ ID NO 1
<211> LENGTH: 18
<212> TYPE: DNA
<213> ORGANISM: Artificial Sequence
<220> FEATURE:
<223> OTHER INFORMATION: SYNTHESIZED
<220> FEATURE:
<221> NAME/KEY: misc_feature
<222> LOCATION: (1)..(18)
<223> OTHER INFORMATION: Peptide Nucleic Acid

<400> SEQUENCE: 1
gtaggtgttt cgtgtggt                                                 18

<210> SEQ ID NO 2
<211> LENGTH: 18
<212> TYPE: DNA
<213> ORGANISM: Artificial Sequence
<220> FEATURE:
<223> OTHER INFORMATION: SYNTHESIZED
<220> FEATURE:
<221> NAME/KEY: misc_feature
<222> LOCATION: (1)..(18)
<223> OTHER INFORMATION: Peptide Nucleic Acid

<400> SEQUENCE: 2
accacacgaa acacctac                                                 18